(12) United States Patent
Tomasselli et al.

(10) Patent No.: US 7,732,183 B2
(45) Date of Patent: *Jun. 8, 2010

(54) METHOD FOR REFOLDING ENZYMES

(75) Inventors: Alfredo Tomasselli, Kalamazoo, MI (US); Robert Heinrikson, Plainwell, MI (US); Donna Paddock, Kalamazoo, MI (US); Ana Mildner, Kalamazoo, MI (US); Thomas Emmons, Portage, MI (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 547 days.

This patent is subject to a terminal disclaimer.

(21) Appl. No.: 11/703,493

(22) Filed: Feb. 7, 2007

(65) Prior Publication Data

US 2009/0053787 A1    Feb. 26, 2009

Related U.S. Application Data

(63) Continuation of application No. 10/230,677, filed on Aug. 29, 2002, now Pat. No. 7,186,539.

(60) Provisional application No. 60/316,934, filed on Aug. 31, 2001.

(51) Int. Cl.
*C12N 9/50* (2006.01)
(52) U.S. Cl. ........................ 435/219; 435/226
(58) Field of Classification Search ........................ None
See application file for complete search history.

(56) References Cited

U.S. PATENT DOCUMENTS

| | | | |
|---|---|---|---|
| 5,744,346 | A | 4/1998 | Chrysler et al. |
| 6,319,689 | B1 | 11/2001 | Powell et al. |
| 6,323,326 | B1 | 11/2001 | Dorin et al. |
| 6,545,127 | B1 | 4/2003 | Tang et al. |
| 6,583,268 | B2 | 6/2003 | Lin |

FOREIGN PATENT DOCUMENTS

| | | |
|---|---|---|
| WO | 9822597 | 5/1998 |
| WO | 0017369 | 3/2000 |
| WO | 0047617 | 8/2000 |
| WO | 0100663 | 1/2001 |
| WO | 0123533 | 4/2001 |

OTHER PUBLICATIONS

Yan, Riqiang, et al; *Membrane-anchored aspartyl protease with Alzheimer's disease β secretase activity*; Nature, vol. 402, Dec. 2, 1999.
Vassar, Robert, et al; *β-Secretase Cleavage of Alzheimer's Amyloid Precursor Protein by the Transmembrane Aspartic Protease BACE*; Science, vol. 286, Oct. 22, 1999.
Sinha, Sukanto, et al; *Purification and cloning of amyloid precursor protein β—secretase from human brain*; Nature, vol. 402, (6761):537-540.
Mallender, William; *Characterization of Recombinant, Soluble β-Secretase from an Insect Cell Expression System*; Molecular Pharmacology; 59: 619-626, 2001.
Benjannet, Suzanne, et al; *Post-translational Processing of β—Secretase (β-Amyloid-converting Enzyme) and its Ectodomain Shedding*; The Journal of Biological Chemistry, vol. 276, No. 14, Apr. 6, 2001; 10879-10887.
Capell, Anja, et al; *Maturation of Pro-peptide Cleavage of β-Secretase;* The Journal of Biological Chemistry, vol. 275, No. 40, Oct. 6, 2000; pp. 30849-30854.
Charlwood, Joanne, et al; Characterization of the Blycosylation Profiles of Alzheimer's β—Secretase Protein Asp-2 Expressed in a Variety of Cell Lines; The Journal of Bioological Chemistry, vol. 276, No. 20, May 18, 2001; p. 16739-16748.
Ermolieff, Jacques, et al; *Proteolytic Activation of Recombinant Pro-memapsin 2 (Pro-β-secretase) Studied with New Fluorogenic Substrates*; Biochemistry 2000, 39, 12450-12456.
Haniu, Mitsuru, et al; *Chracterization of Alzheimer's β—Secretase Protein BACE;* The Journal of Biological Chemistry; vol. 275, No. 28, Jul. 14, 2000; pp. 21099-21106.
Hussain, Ishrut, et al; *Identification of a Novel Aspartic Protease (Asp 2) as β—Secretase;* Molecular and Cellular Neuroscience; 14, 419-427 (1999).
Khan, Amir, et al; *Molecular mechanisms for the convesion of zymogens to active proteolytic enzymes;* Protein Science (1998) 7:815-836.
Lin, Xinli, et al; *Rearranging the domains of pepsinogen;* (1995), 4:159-166.
Lin, Xin-Li, et al; *Synthesis, Purification, and Active Site Mutagenesis of Recombinant Procine Pepsinogen;* The Journal of Biological Chemistry; vol. 264, No. 8, Mar. 15, 1989; pp. 4482-4489.
Lin, Xinli, et al; *Human aspartic proteas emeapsin 2 cleaves the β—amyloid precursor protein;* PNAS, Feb. 15, 2000; vol. 97, pp. 1456-1460.
Mildner, Ana, et al; *Production of Chemokines CTAPIII and NAP/2 by Digestion of Recombinant Ubiquitin-CTAPIII with Yeast Ubiquitin C-Terminal Hydrolase and Human Immunodeficiency Virus Protease;* Protein Expression and Purification vol. 16, 347-354 (1999).
Selkoe, D.J.; *Cell Biology of the β—Amyloid Precursor Protein and the Genetics of alzheimer's Disease;* Cold Spring Harbor Symposia on Quantatative Biology, vol. LXI, 1996, pp. 587-596.
Selkoe, Dennis J.,; *translating cell biology into therapeutic advances in Alzheimer's disease;* Nature, vol. 399, Jun. 24, 199 pp. A23-A31.

(Continued)

*Primary Examiner*—Nashaat T Nashed
(74) *Attorney, Agent, or Firm*—McDonnell Boehnen Hulbert & Berghoff LLP

(57) ABSTRACT

The invention provides methods for efficient recombinant expression, refolding, and purification of Beta-site APP cleaving enzyme (BACE) polypeptides. In various aspects, the method includes the steps of expressing a recombinant construct in bacteria, dissolving inclusion bodies with a denaturant at high pH in the presence of a reducing agent, diluting the solubilized BACE polypeptide in an aqueous solution at a temperature of about 1° C. to 15° C., and incubating the diluted sample at a temperature of about 4° C. to 15° C. until the recombinant BACE polypeptide folds into an active enzyme.

24 Claims, 15 Drawing Sheets

OTHER PUBLICATIONS

Thinakaran, Gopal, et al; *Metabolis of the "Swedish" Amyloid Precursor Protein Variant in Neuro2a (N2a) Cells;* the Journal of Biological Chemistry; vol. 271, No. 16, Apr. 19, 1996; pp. 9390-9397.

Hong, L. et al; Structure of the protease domain of memapsin 2 (beta-secretase) complexed with inhibitor; Science 2000; 290(5489), 150-3.

Heinrikson, R.L., et al; The Biochemistry and molecular biology of recombinant rennin and proorenin; Hypertension: Pathophysiology, Diagnosis and management 1990; chapter 74:1179-1196.

Shi, X-P, et al ; The pro domain of -secretase does not confer strict zymogen-like properties but assist proper refolding of the protease domain; J. Biol. Chem 2001; 267:10366-10373.

Inagami, T., et al; Biomed Res. 1980; 1:456-475.

Schechter, Israel, et al; *On the Size of the Active Site in Proteases. I Papain,* Biochemical and Biophysical Research Communications, vol. 27, No. 2, 1967; pp. 157-162.

Shi, Xiao-Ping, et al; *The Pro Domain of B-Secretase does not Confer Strict Zymogen-like Properties but Does Assit Proper Folding of the Protease Domain;* vol. 276, No. 13, 2001; pp. 10366-10373.

Heinrikson, Robert L, et al; *The Biochemistry and Molecular Biology of Recombinant Human Renin and Prorenin;* Hypertension: Pathophysiology, Diagnosis and Management; 1990; pp. 1179-1196.

Hong, Lin, et al; *Structure of the Protease Domain of Memapsin2 (B-Secretase) Complexed with Inhibitor,* Science Magazine, vol. 290, Oct. 6, 2000; pp. 150-153.

Selkoe, Dennis, J.; *Alzheimer's Disease: Genes, Proteins and Therapy,* Physiological Review, vol. 81, No. 2, Apr. 2001, pp. 741-766.

FIG. 1

Amino Acid Sequence of Human BACE

MAQALPWLLLLWMGAGVLPAHG T$^1$QHGIRLPLR SGLGGAPLGL RLPRETDEEP
EEPGRRGSFV EMVDNLRGKS GQGYYVEMTV GSPPQTLNIL VDTGSSNFAV
GAAPHPFLHR YYQRQLSSTY RDLRKGVYVP YTQGKWEGEL GTDLVSIPHG
PNVTVRANIA AITESDKFFI NGSNWEGILG LAYAEIARPD DSLEPFFDSL
VKQTHVPNLF SLQLCGAGFP LNQSEVLASV GGSMIIGGID HSLYTGSLWY
TPIRREWYYE VIIVRVEING QDLKMDCKEY NYDKSIVDSG TTNLRLPKKV
FEAAVKSIKA ASSTEKFPDG FWLGEQLVCW QAGTTPWNIF PVISLYLMGE
VTNQSFRITI LPQQYLRPVE DVATSQDDCY KFAISQSSTG TVMGAVIMEG
FYVVFDRARK RIGFAVSACH VHDEFRTAAV EGPFVTLDME DCGYNIPQTD
ES$^{432}$ TLMTIAYV MAAICALFML PLCLMVCQWR CLRCLRQQHD DFADDISLLK

[SEQ ID NO: 1]

FIG. 2A

DNA [SEQ ID NO: 4] and predicted amino acid [SEQ ID NO: 5] sequences of pET11a-BACE

```
                                                    -8
Met Ala Ser Met Thr Gly Gly Gln Gln Met Gly Arg Gly Ser Met Ala Gly Val Leu Pro    -4
atg gct agc atg act ggt gga cag caa atg ggt cgc gga tcc atg gct ggt gtt ctg cca
                                              1

Ala His Gly Thr Gln His Gly Ile Arg Leu Pro Leu Arg Ser Gly Leu Gly Ala Pro         17
gct cac ggt acc caa cat ggt att cgt ctg cca ctg cgt agc ggt ctg ggt gct cca Leu Gly Leu Arg Leu Pro Arg Glu Thr Asp Glu Glu Pro Gly Glu Pro Gly Arg Arg Gly     37
ctg ggt ctg cgt ctg ccc cgc gag acc gac gag gag ccc gga gag ccc ggc agg agg ggc Ser Phe Val Glu Met Val Asp Asn Leu Arg Gly Lys Ser Gly Gln Gly Tyr Tyr Val Glu     57
agc ttt gtg gag atg gtg gac aac ctg agg ggc aag tcg ggg cag ggc tac tac gtg gag Met Thr Val Gly Ser Pro Pro Gln Thr Leu Asn Ile Leu Val Asp Thr Gly Ser Ser Asn     77
atg acc gtg ggc agc ccc ccg cag acg ctc aac atc ctg gtg gat aca ggc agc agt aac Phe Ala Val Gly Ala Ala Pro His Pro Phe Leu His Arg Tyr Tyr Gln Arg Gln Leu Ser     97
ttt gca gtg ggt gct gcc ccc cac ccc ttc ctg cat cgc tac tac cag agg cag ctg tcc Ser Thr Tyr Arg Asp Leu Arg Lys Gly Val Tyr Val Pro Tyr Thr Gln Gly Lys Trp Glu    117
agc aca tac cgg gac ctc cgg aag ggc gtg tat gtg ccc tac acc cag ggc aag tgg gaa Gly Glu Leu Gly Thr Asp Leu Val Ser Ile Pro His Gly Pro Asn Val Thr Val Arg Ala    137
ggg gag ctg ggc acc gac ctg gta agc atc ccc cat ggc ccc aac gtc act gtg cgt gcc Asn Ile Ala Ala Ile Thr Glu Ser Asp Lys Phe Phe Ile Asn Gly Ser Asn Trp Glu Gly    157
aac att gct gcc atc act gaa tca gac aag ttc ttc atc aac ggc tcc aac tgg gaa ggc
```

FIG. 2B

```
Ile Leu Gly Leu Ala Tyr Ala Glu Ile Ala Arg Pro Asp Asp Ser Leu Glu Pro Phe Phe    177
atc ctg ggg ctg gcc tat gct gag att gcc agg cct gac gac tcc ctg gag cct ttc ttt Asp Ser Leu Val Lys Gln Thr His Val Pro Asn Leu Phe Ser Leu Gln Leu Cys Gly Ala    197
gac tct ctg gta aag cag acc cac gtt ccc aac ctc ttc tcc ctg cag ctt tgt ggt gct Gly Phe Pro Leu Asn Gln Ser Glu Val Leu Ala Ser Val Gly Gly Ser Met Ile Ile Gly    217
ggc ttc ccc ctc aac cag tct gaa gtg ctg gcc tct gtc gga ggg agc atg atc att gga Gly Ile Asp His Ser Leu Tyr Thr Gly Ser Leu Trp Tyr Thr Pro Ile Arg Arg Glu Trp    237
ggt atc gac cac tcg ctg tac aca ggc agt ctc tgg tat acc ccc atc cgg gag tgg Tyr Tyr Glu Val Ile Ile Val Arg Val Glu Ile Asn Gly Gln Asp Leu Lys Met Asp Cys    257
tat tat gag gtc atc att gtg cgg gtg gag atc aat gga cag gat ctg aaa atg gac tgc Lys Glu Tyr Asn Tyr Asp Ser Ile Val Asp Ser Gly Thr Thr Asn Leu Arg Leu Pro    277
aag gag tac aac tat gac agc agt gtg gac agt ggc acc aac ctt cgt ttg ccc Lys Lys Val Phe Glu Ala Ala Val Lys Ser Ile Lys Ala Ala Ser Ser Thr Glu Lys Phe    297
aag aaa gtg ttt gaa gct gca gtc aaa tcc atc aag gcc tcc acg gag aag ttc Pro Asp Gly Phe Trp Leu Gly Glu Gln Leu Val Cys Trp Gln Ala Gly Thr Thr Pro Trp    317
cct gat ggt ttc tgg cta gga gag cag ctg gtg tgc tgg caa gca ggc acc acc cct tgg Asn Ile Phe Pro Val Ile Ser Leu Tyr Leu Met Gly Glu Val Thr Asn Gln Ser Phe Arg    337
aac atc ttc cca gtc atc tca ctc tac cta atg ggt gag gtt acc aac cag tcc ttc cgc Ile Thr Ile Leu Pro Gln Gln Tyr Leu Arg Pro Val Glu Asp Val Ala Thr Ser Gln Asp    357
atc acc atc ctt ccg caa cag tac ctg cgg cca gtg gaa gat gtg gcc acg tcc caa gac
```

FIG. 2C

```
Asp Cys Tyr Lys Phe Ala Ile Ser Gln Ser Ser Thr Gly Thr Val Met Gly Ala Val Ile    377
gac tgt tac aag ttt gcc atc tca cag tca tcc acg ggc act gtt atg gga gct gtt atc Met Glu Gly Phe Tyr Val Val Phe Asp Arg Ala Arg Lys Arg Ile Gly Phe Ala Val Ser    397
atg gag ggc ttc tac gtt gtc ttt gat cgg gcc cga aaa cga att ggc ttt gct gtc agc Ala Cys His Val His Asp Glu Phe Arg Thr Ala Ala Val Glu Gly Pro Phe Val Thr Leu    417
gct tgc cat gtg cat gat gag ttc agg acg gca gcg gtg gaa ggc cct ttt gtc acc ttg Asp Met Glu Asp Cys Gly Tyr Asn Ile Pro Gln Thr Asp Glu Ser End   432    [SEQ ID NO:5]
gac atg gaa gac tgt ggc tac aac att cca cag aca gat gag tca tag          [SEQ ID NO:4]
```

FIG. 3A

DNA [SEQ ID NO: 6] and predicted amino acid [SEQ ID NO: 7] sequences of pQE80L-BACE

```
                                                                                           1
Met Arg Gly Ser His His His His His His Gly Ser Ile Glu Thr Asp Thr Gln His Gly            4
atg aga gga tcg cat cac cat cac cat cac gga tcc atc gag acc gac acc caa cat ggt Ile Arg Leu Pro Leu Arg Ser Gly Leu Gly Gly Ala Pro Leu Gly Leu Arg Leu Pro Arg            24
att cgt ctg cca ctg cgt agc ggt ctg ggt gct cca ctg ggt cgt ctg cct cgg Glu Thr Asp Glu Glu Pro Glu Glu Pro Gly Arg Arg Gly Ser Phe Val Glu Met Val Asp            44
gag acc gac gaa gag ccc gag gag ccc ggc cgg agg ggc agc ttt gtg gag atg gtg gac Asn Leu Arg Gly Lys Ser Gly Gln Gly Tyr Tyr Val Glu Met Thr Val Gly Ser Pro Pro            64
aac ctg agg ggc aag tcg ggg cag ggc tac tac gtg gag atg acc gtg ggc agc ccc ccg Gln Thr Leu Asn Ile Leu Val Asp Thr Gly Ser Ser Asn Phe Ala Val Gly Ala Ala Pro            84
cag acg ctc aac atc ctg gtg gat aca ggc agc agt aac ttt gca gtg ggt gct gcc ccc His Pro Phe Leu His Arg Tyr Tyr Gln Arg Gln Leu Ser Ser Thr Tyr Arg Asp Leu Arg            104
cac ccc ttc ctg cat cgc tac tac cag agg cag ctg agc tcc acc tac cgg gac ctc cgg Lys Gly Val Tyr Val Pro Tyr Thr Gln Gly Lys Trp Glu Gly Glu Leu Gly Thr Asp Leu            124
aag ggc gtg tat gtg ccc tac acc cag ggc aag tgg gaa ggg gag ctg ggc acc gac ctg Val Ser Ile Pro His Gly Pro Asn Val Thr Val Arg Ala Asn Ile Ala Ala Ile Thr Glu            144
gta agc atc ccc cat ggc ccc aac gtc cgt act gtc gcc aac att gct gcc atc act gaa Ser Asp Lys Phe Phe Ile Asn Gly Ser Asn Trp Glu Gly Ile Leu Gly Leu Ala Tyr Ala            164
tca gac aag ttc ttc atc aac ggc tcc aac tgg gaa ggc atc ctg ggg ctg gcc tat gct
```

FIG. 3B

| Glu | Ile | Ala | Arg | Pro | Asp | Asp | Ser | Leu | Glu | Pro | Phe | Phe | Asp | Ser | Leu | Val | Lys | Gln | Thr | 184 |
| gag | att | gcc | agg | cct | gac | gac | tcc | ctg | gag | cct | ttc | ttt | gac | tct | ctg | gta | aag | cag | acc | |
| His | Val | Pro | Asn | Leu | Phe | Ser | Leu | Gln | Leu | Cys | Gly | Ala | Gly | Phe | Pro | Leu | Asn | Gln | Ser | 204 |
| cac | gtt | ccc | aac | ctc | ttc | tcc | ctg | cag | ctt | tgt | ggt | gct | ggc | ttc | ccc | ctc | aac | cag | tct | |
| Glu | Val | Leu | Ala | Ser | Val | Gly | Gly | Ser | Met | Ile | Ile | Gly | Gly | Ile | Asp | His | Ser | Leu | Tyr | 224 |
| gaa | gtg | ctg | gcc | tct | gtc | gga | ggg | agc | atg | atc | att | gga | ggt | atc | gac | cac | tcg | ctg | tac | |
| Thr | Gly | Ser | Leu | Trp | Tyr | Thr | Pro | Ile | Arg | Glu | Trp | Tyr | Tyr | Glu | Val | Ile | Ile | Val | 244 |
| aca | ggc | agt | ctc | tgg | tat | aca | ccc | atc | cgg | gag | tgg | tat | tat | gag | gtc | atc | att | gtg | |
| Arg | Val | Asp | Ile | Asn | Gly | Gln | Asp | Leu | Lys | Met | Asp | Cys | Lys | Glu | Tyr | Asn | Tyr | Asp | Lys | 264 |
| cgg | gtg | gag | atc | aat | gga | cag | gat | ctg | aaa | atg | gac | tgc | aag | gag | tac | aac | tat | gac | aag | |
| Ser | Ile | Val | Asp | Ser | Gly | Thr | Thr | Asn | Leu | Arg | Leu | Pro | Lys | Val | Phe | Glu | Ala | Ala | 284 |
| agc | att | gtg | gac | agt | ggc | acc | acc | aac | ctt | cgt | ttg | ccc | aag | gtg | ttt | gaa | gct | gca | |
| Val | Lys | Ser | Ile | Ala | Ala | Ser | Gly | Thr | Glu | Lys | Phe | Pro | Asp | Gly | Phe | Trp | Leu | Gly | 304 |
| gtc | aaa | tcc | atc | gca | gcc | tcc | gga | acg | gag | aag | ttc | cct | gat | ggt | ttc | tgg | cta | gga | |
| Glu | Gln | Leu | Val | Cys | Trp | Gln | Ala | Gly | Thr | Thr | Pro | Trp | Asn | Ile | Phe | Pro | Val | Ile | Ser | 324 |
| gag | cag | ctg | gtg | tgc | tgg | caa | gca | ggc | acc | acc | cct | tgg | aac | att | ttc | cca | gtc | atc | tca | |
| Leu | Tyr | Leu | Met | Gly | Glu | Val | Thr | Asn | Gln | Ser | Phe | Arg | Ile | Thr | Ile | Leu | Pro | Gln | Gln | 344 |
| ctc | tac | cta | atg | ggt | gag | gtt | acc | aac | cag | tcc | ttc | cgc | atc | acc | atc | ctt | ccg | cag | caa | |
| Tyr | Leu | Arg | Pro | Val | Glu | Asp | Val | Ala | Thr | Ser | Gln | Asp | Asp | Cys | Tyr | Lys | Phe | Ala | Ile | 364 |
| tac | ctg | cgg | cca | gtg | gaa | gat | gtg | gcc | acg | tcc | caa | gac | gac | tgt | tac | aag | ttt | gcc | atc | |

FIG. 3C

```
Ser Gln Ser Ser Thr Gly Thr Val Met Gly Ala Val Ile Met Glu Gly Phe Tyr Val Val    384
tca cag tca tcc acg ggc act gtt atg gga gct gtt atc atg gag ggc ttc tac gtt gtc Phe Asp Arg Ala Arg Ile Gly Phe Ala Val Ser Ala Cys His Val Asp Glu              404
ttt gat cgg gcc cga aaa cga att ggc ttt gct gtc agc gct tgc cat gtg cac gat gag Phe Arg Thr Ala Ala Val Glu Gly Pro Phe Val Thr Leu Asp Met Glu Asp Cys Gly Tyr  424
ttc agg acg gca gcg gtg gaa ggc cct ttt gtc acc ttg gac atg gaa gac tgt ggc tac Asn Ile Pro Gln Thr Asp Glu Ser End      [SEQ ID NO:7]
aac att cca cag aca gat gag tca tga      [SEQ ID NO:6]
```

FIG. 4A

DNA [SEQ ID NO: 2] and predicted amino acid [SEQ ID NO: 3] sequences of pQE70(Arg$^{36}$ - Ser$^{432}$)

```
36
Met Arg Gly Ser Phe Val Glu Met Val Asp Asn Leu Arg Gly Lys Ser Gly Gln Gly Tyr    54
ATG CGT GGC AGC TTT GTG GAG ATG GTG GAC AAC CTG AGG GGC AAG TCG GGG CAG GGC TAC

Tyr Val Glu Met Thr Val Gly Ser Pro Pro Gln Thr Leu Asn Ile Leu Val Asp Thr Gly    74
TAC GTG GAG ATG ACC GTG GGC AGC CCG CCG CAG ACG CTC AAC ATC CTG GTG GAT ACA GGC

Ser Ser Asn Phe Ala Val Gly Ala Ala Pro His Pro Phe Leu His Arg Tyr Tyr Gln Arg    94
AGC AGT AAC TTT GCA GTG GGT GCT CCC CAC CCC TTC CTG CAT CGN TAC TAC CAG AGG

Gln Leu Ser Ser Thr Tyr Arg Asp Leu Arg Lys Gly Val Tyr Val Pro Tyr Thr Gln Gly   114
CAG CTG TCC AGC ACA TAC CGG GAC CTC CGG AAG GGC GTG TAT GTG CCC TAC ACC CAG GGC

Lys Trp Glu Gly Glu Leu Gly Thr Asp Leu Val Ser Ile Pro His Gly Pro Asn Val Thr   134
AAG TGG GAA GGG GAG CTG GGC ACC GAC CTG GTA AGC ATC CCC CAT GGC CCC AAC GTC ACT

Val Arg Ala Asn Ile Ala Ile Thr Glu Ser Asp Lys Phe Phe Ile Asn Gly Ser Asn       154
GTG CGT GCC AAC ATT GCT GCC ATC ACT GAA TCA GAC AAG TTC TTC ATC AAC GGC TCC AAC

Trp Glu Gly Ile Leu Gly Leu Ala Tyr Ala Glu Ile Ala Arg Pro Asp Asp Ser Leu Glu   174
TGG GAA GGC ATC CTG GGG CTG GCC TAT GCT GAG ATT GCC AGG CCT GAC GAC TCC CTG GAG

Pro Phe Phe Asp Ser Leu Val Lys Gln Thr His Val Pro Asn Leu Phe Ser Leu Gln Leu   194
CCT TTC TTT GAC TCT CTG GTA AAG CAG ACC CAC GTT CCC AAC CTC TTC TCC CTG CAG CTT

Cys Gly Ala Gly Phe Pro Leu Asn Gln Ser Glu Val Leu Ala Ser Val Gly Gly Ser Met   214
TGT GGT GCT GGC TTC CCC CTC AAC CAG TCT GAA GTG CTG GCC TCT GTC GGA GGG AGC ATG

Ile Ile Gly Gly Ile Asp His Ser Leu Tyr Thr Gly Ser Leu Trp Tyr Thr Pro Ile Arg   234
ATC ATT GGA GGT ATC GAC CAC TCG CTG TAC ACA GGC AGT CTC TGG TAT ACA CCC ATC CGG
```

FIG. 4B

```
Arg Glu Trp Tyr Tyr Glu Val Ile Val Arg Val Glu Ile Asn Gly Gln Asp Leu Lys   254
CGG GAG TGG TAT TAT GAG GTC ATT GTG CGG GTG GAG ATC AAT GGA CAG GAT CTG AAA

Met Asp Cys Lys Glu Tyr Asn Tyr Asp Lys Ser Ile Val Asp Ser Gly Thr Thr Asn Leu   274
ATG GAC TGC AAG GAG TAC AAC TAT GAC AAG AGC ATT GTG GAC AGT GGC ACC ACC AAC CTT

Arg Leu Pro Lys Lys Val Phe Glu Ala Ala Val Lys Ser Ile Lys Ala Ala Ser Ser Thr   294
CGT TTG CCC AAG AAA GTG TTT GAA GCT GCA GTC AAA TCC ATC AAG GCA GCC TCC TCC ACG

Glu Lys Phe Pro Asp Gly Phe Trp Leu Gly Glu Gln Leu Val Cys Trp Gln Ala Gly Thr   314
GAG AAG TTC CCT GAT GGT TTC TGG CTA GGA GAG CTG GTG TGC TGG CAA GCA GGC ACC

Thr Pro Trp Asn Ile Phe Pro Val Ile Ser Leu Tyr Leu Met Gly Glu Val Thr Asn Gln   334
ACC CCT TGG AAC ATT TTC CCA GTC ATC TCA CTC TAC CTA ATG GGT GAG GTT ACC AAC CAG

Ser Phe Arg Ile Thr Ile Leu Pro Gln Gln Tyr Leu Arg Pro Val Glu Asp Val Ala Thr   354
TCC TTC CGC ATC ACC ATC CTT CCG CAG CAA TAC CTG CGG CCA GTG GAA GAT GTG GCC ACG

Ser Gln Asp Asp Cys Tyr Lys Phe Ala Ile Ser Thr Gly Thr Val Met Gly   374
TCC CAA GAC GAC TGT TAC AAG TTT GCC ATC TCA CAG TCC ACG GGC ACT GTT ATG GGA

Ala Val Ile Met Glu Gly Phe Tyr Val Phe Asp Arg Ala Arg Lys Arg Ile Gly Phe   394
GCT GTT ATC ATG GAG GGC TTC TAC GTT TTT GAT CGG GCC CGA AAA CGA ATT GGC TTT

Ala Val Ser Ala Cys His Val Asp Phe Arg Thr Ala Ala Val Glu Gly Pro Phe   414
GCT GTC AGC GCT TGC CAT GTG CAC GAT TTC AGG ACG GCA GCG GTG GAA GGC CCT TTT

Val Thr Leu Asp Met Glu Asp Cys Gly Tyr Asn Ile Pro Gln Thr Asp Glu Ser Arg Ser   434
GTC ACC TTG GAC ATG GAA GAC TGT GGC TAC AAC ATT CCA CAG ACA GAT GAG TCA AGA TCT

His His His His His His End   [SEQ ID NO. 3]
CAT CAC CAT CAC CAT CAC TAA   [SEQ ID NO. 2]
```

BACE Refolding and Optimization.

FIG. 6
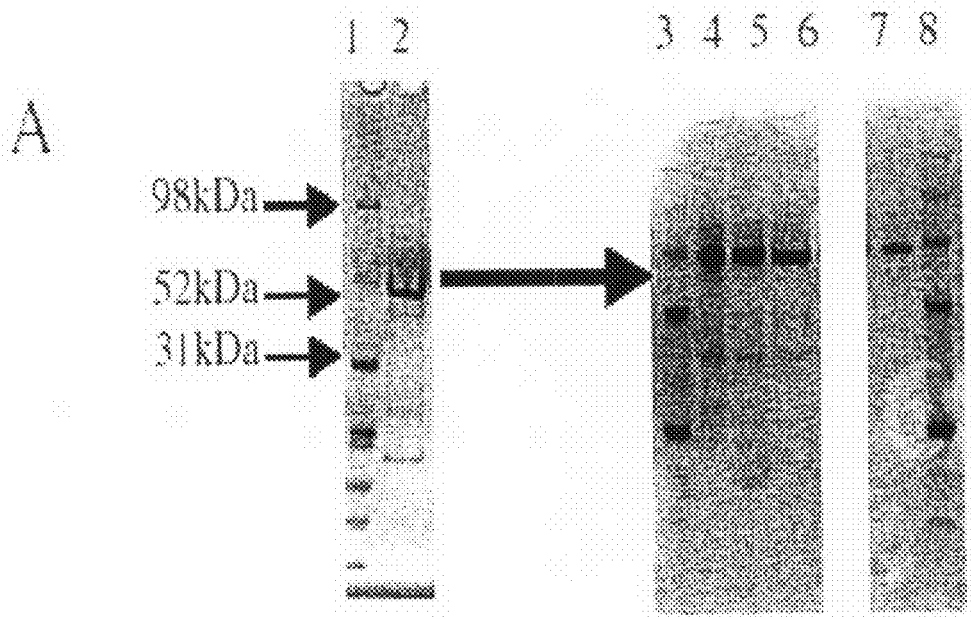
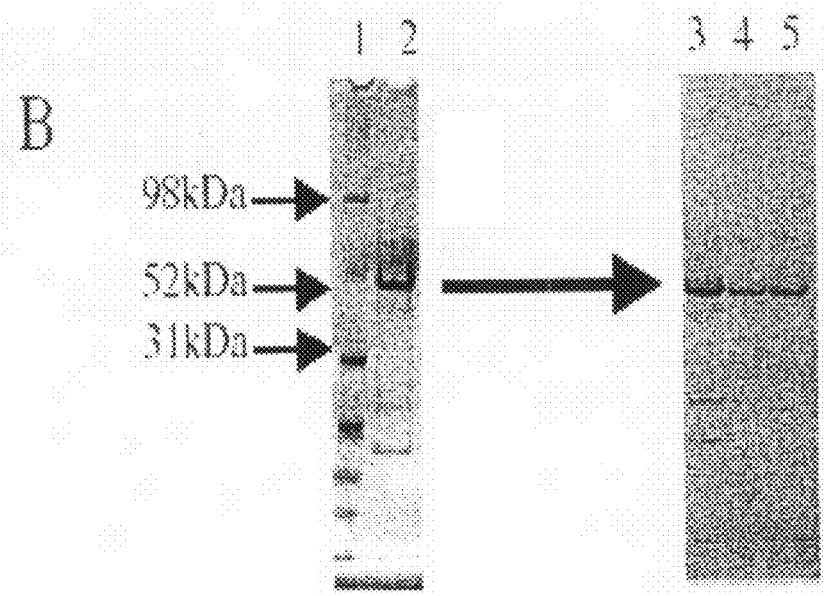
Two methods of purification of PET11a-BACE.

SDS-PAGE of Fractions from
pQE70-BACE ($R^{36}...S^{432}$) Purification Steps.

Recombinant BACE.

FIG. 9

BACE Construct Asp2-2L–TM-His$_6$

```
  1  MAQALPWLLL  WMGAGVLPAH  GT¹QHGIRLPL  RSGLGGAPLG  LRLPRE²⁵TDEE
 51  PEEPGRRGSF  VEMVDNLRGK  SGQGYYVEMT  VGSPPQTLNI  LVDTGSSNFA
101  VGAAPHPFLH  RYYQRQLSST  YRDLRKGVYV  PYTQGKWEGE  LGTDLVSIPH
151  GPNVTVRANI  AAITESDKFF  INGSNWEGIL  GLAYAEIARP  DDSLEPFFDS
201  LVKQTHVPNL  FSLQLCGAGF  PLNQSEVLAS  VGGSMIIGGI  DHSLYTGSLW
251  YTPIRREWYY  EVIIVRVEIN  GQDLKMDCKE  YNYDKSIVDS  GTTNLRLPKK
301  VFEAAVKSIK  AASSTEKFPD  GFWLGEQLVC  WQAGTTPWNI  FPVISLYLMG
351  EVTNQSFRIT  ILPQQYLRPV  EDVATSQDDC  YKFAISQSST  GTVMGAVIME
401  GFYVVFDRAR  KRIGFAVSAC  HVHDEFRTAA  VEGPFVTLDM  EDCGYNIPQT
451  DESHHHHHH     [SEQ ID NO:23]
```

Polypeptides expressed from the construct
pQE80L- BACE, including treatments with HIV-protease.

SEQUENCE LISTING

<160> NUMBER OF SEQ ID NOS: 33

<210> SEQ ID NO 1
<211> LENGTH: 501
<212> TYPE: PRT
<213> ORGANISM: Homo sapiens

<400> SEQUENCE: 1

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
            290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
            370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
            450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 2
<211> LENGTH: 1221
<212> TYPE: DNA
<213> ORGANISM: Homo sapiens
<220> FEATURE:
<221> NAME/KEY: CDS
<222> LOCATION: (1)..(1221)
<220> FEATURE:
<221> NAME/KEY: misc_feature
<222> LOCATION: (168)..(168)
<223> OTHER INFORMATION: N is A, T, G, or C

<400> SEQUENCE: 2 atg cgt ggc agc ttt gtg gag atg gtg gac aac ctg agg ggc aag tcg      48
Met Arg Gly Ser Phe Val Glu Met Val Asp Asn Leu Arg Gly Lys Ser
1               5                   10                  15 ggg cag ggc tac tac gtg gag atg acc gtg ggc agc ccc ccg cag acg      96
Gly Gln Gly Tyr Tyr Val Glu Met Thr Val Gly Ser Pro Pro Gln Thr
                20                  25                  30 ctc aac atc ctg gtg gat aca ggc agc agt aac ttt gca gtg ggt gct     144
Leu Asn Ile Leu Val Asp Thr Gly Ser Ser Asn Phe Ala Val Gly Ala
            35                  40                  45 gcc ccc cac ccc ttc ctg cat cgn tac tac cag agg cag ctg tcc agc     192
Ala Pro His Pro Phe Leu His Arg Tyr Tyr Gln Arg Gln Leu Ser Ser
        50                  55                  60 aca tac cgg gac ctc cgg aag ggc gtg tat gtg ccc tac acc cag ggc     240
Thr Tyr Arg Asp Leu Arg Lys Gly Val Tyr Val Pro Tyr Thr Gln Gly
65                  70                  75                  80

| | | |
|---|---|---|
| aag tgg gaa ggg gag ctg ggc acc gac ctg gta agc atc ccc cat ggc<br>Lys Trp Glu Gly Glu Leu Gly Thr Asp Leu Val Ser Ile Pro His Gly<br>                        85                             90                            95 | 288 |
| ccc aac gtc act gtg cgt gcc aac att gct gcc atc act gaa tca gac<br>Pro Asn Val Thr Val Arg Ala Asn Ile Ala Ala Ile Thr Glu Ser Asp<br>               100                           105                       110 | 336 |
| aag ttc ttc atc aac ggc tcc aac tgg gaa ggc atc ctg ggg ctg gcc<br>Lys Phe Phe Ile Asn Gly Ser Asn Trp Glu Gly Ile Leu Gly Leu Ala<br>        115                           120                       125 | 384 |
| tat gct gag att gcc agg cct gac gac tcc ctg gag cct ttc ttt gac<br>Tyr Ala Glu Ile Ala Arg Pro Asp Asp Ser Leu Glu Pro Phe Phe Asp<br>        130                           135                       140 | 432 |
| tct ctg gta aag cag acc cac gtt ccc aac ctc ttc tcc ctg cag ctt<br>Ser Leu Val Lys Gln Thr His Val Pro Asn Leu Phe Ser Leu Gln Leu<br>145                       150                       155                       160 | 480 |
| tgt ggt gct ggc ttc ccc ctc aac cag tct gaa gtg ctg gcc tct gtc<br>Cys Gly Ala Gly Phe Pro Leu Asn Gln Ser Glu Val Leu Ala Ser Val<br>                      165                       170                       175 | 528 |
| gga ggg agc atg atc att gga ggt atc gac cac tcg ctg tac aca ggc<br>Gly Gly Ser Met Ile Ile Gly Gly Ile Asp His Ser Leu Tyr Thr Gly<br>        180                           185                       190 | 576 |
| agt ctc tgg tat aca ccc atc cgg cgg gag tgg tat tat gag gtc atc<br>Ser Leu Trp Tyr Thr Pro Ile Arg Arg Glu Trp Tyr Tyr Glu Val Ile<br>               195                           200                       205 | 624 |
| att gtg cgg gtg gag atc aat gga cag gat ctg aaa atg gac tgc aag<br>Ile Val Arg Val Glu Ile Asn Gly Gln Asp Leu Lys Met Asp Cys Lys<br>        210                           215                       220 | 672 |
| gag tac aac tat gac aag agc att gtg gac agt ggc acc acc aac ctt<br>Glu Tyr Asn Tyr Asp Lys Ser Ile Val Asp Ser Gly Thr Thr Asn Leu<br>225                       230                       235                       240 | 720 |
| cgt ttg ccc aag aaa gtg ttt gaa gct gca gtc aaa tcc atc aag gca<br>Arg Leu Pro Lys Lys Val Phe Glu Ala Ala Val Lys Ser Ile Lys Ala<br>                      245                       250                       255 | 768 |
| gcc tcc tcc acg gag aag ttc cct gat ggt ttc tgg cta gga gag cag<br>Ala Ser Ser Thr Glu Lys Phe Pro Asp Gly Phe Trp Leu Gly Glu Gln<br>                 260                           265                       270 | 816 |
| ctg gtg tgc tgg caa gca ggc acc acc cct tgg aac att ttc cca gtc<br>Leu Val Cys Trp Gln Ala Gly Thr Thr Pro Trp Asn Ile Phe Pro Val<br>        275                           280                       285 | 864 |
| atc tca ctc tac cta atg ggt gag gtt acc aac cag tcc ttc cgc atc<br>Ile Ser Leu Tyr Leu Met Gly Glu Val Thr Asn Gln Ser Phe Arg Ile<br>        290                           295                       300 | 912 |
| acc atc ctt ccg cag caa tac ctg cgg cca gtg gaa gat gtg gcc acg<br>Thr Ile Leu Pro Gln Gln Tyr Leu Arg Pro Val Glu Asp Val Ala Thr<br>305                       310                       315                       320 | 960 |
| tcc caa gac gac tgt tac aag ttt gcc atc tca cag tca tcc acg ggc<br>Ser Gln Asp Asp Cys Tyr Lys Phe Ala Ile Ser Gln Ser Ser Thr Gly<br>                      325                       330                       335 | 1008 |
| act gtt atg gga gct gtt atc atg gag ggc ttc tac gtt gtc ttt gat<br>Thr Val Met Gly Ala Val Ile Met Glu Gly Phe Tyr Val Val Phe Asp<br>               340                           345                       350 | 1056 |
| cgg gcc cga aaa cga att ggc ttt gct gtc agc gct tgc cat gtg cac<br>Arg Ala Arg Lys Arg Ile Gly Phe Ala Val Ser Ala Cys His Val His<br>        355                           360                       365 | 1104 |
| gat gag ttc agg acg gca gcg gtg gaa ggc cct ttt gtc acc ttg gac<br>Asp Glu Phe Arg Thr Ala Ala Val Glu Gly Pro Phe Val Thr Leu Asp<br>        370                           375                       380 | 1152 |
| atg gaa gac tgt ggc tac aac att cca cag aca gat gag tca aga tct<br>Met Glu Asp Cys Gly Tyr Asn Ile Pro Gln Thr Asp Glu Ser Arg Ser | 1200 |

```
                385                 390                 395                 400
cat cac cat cac cat cac taa                                                       1221
His His His His His His
                405

<210> SEQ ID NO 3
<211> LENGTH: 406
<212> TYPE: PRT
<213> ORGANISM: Homo sapiens

<400> SEQUENCE: 3

Met Arg Gly Ser Phe Val Glu Met Val Asp Asn Leu Arg Gly Lys Ser
1               5                   10                  15

Gly Gln Gly Tyr Tyr Val Glu Met Thr Val Gly Ser Pro Pro Gln Thr
            20                  25                  30

Leu Asn Ile Leu Val Asp Thr Gly Ser Ser Asn Phe Ala Val Gly Ala
        35                  40                  45

Ala Pro His Pro Phe Leu His Arg Tyr Tyr Gln Arg Gln Leu Ser Ser
    50                  55                  60

Thr Tyr Arg Asp Leu Arg Lys Gly Val Tyr Val Pro Tyr Thr Gln Gly
65                  70                  75                  80

Lys Trp Glu Gly Glu Leu Gly Thr Asp Leu Val Ser Ile Pro His Gly
                85                  90                  95

Pro Asn Val Thr Val Arg Ala Asn Ile Ala Ala Ile Thr Glu Ser Asp
            100                 105                 110

Lys Phe Phe Ile Asn Gly Ser Asn Trp Glu Gly Ile Leu Gly Leu Ala
        115                 120                 125

Tyr Ala Glu Ile Ala Arg Pro Asp Asp Ser Leu Glu Pro Phe Phe Asp
    130                 135                 140

Ser Leu Val Lys Gln Thr His Val Pro Asn Leu Phe Ser Leu Gln Leu
145                 150                 155                 160

Cys Gly Ala Gly Phe Pro Leu Asn Gln Ser Glu Val Leu Ala Ser Val
                165                 170                 175

Gly Gly Ser Met Ile Ile Gly Gly Ile Asp His Ser Leu Tyr Thr Gly
            180                 185                 190

Ser Leu Trp Tyr Thr Pro Ile Arg Arg Glu Trp Tyr Tyr Glu Val Ile
        195                 200                 205

Ile Val Arg Val Glu Ile Asn Gly Gln Asp Leu Lys Met Asp Cys Lys
    210                 215                 220

Glu Tyr Asn Tyr Asp Lys Ser Ile Val Asp Ser Gly Thr Thr Asn Leu
225                 230                 235                 240

Arg Leu Pro Lys Lys Val Phe Glu Ala Ala Val Lys Ser Ile Lys Ala
                245                 250                 255

Ala Ser Ser Thr Glu Lys Phe Pro Asp Gly Phe Trp Leu Gly Glu Gln
            260                 265                 270

Leu Val Cys Trp Gln Ala Gly Thr Thr Pro Trp Asn Ile Phe Pro Val
        275                 280                 285

Ile Ser Leu Tyr Leu Met Gly Glu Val Thr Asn Gln Ser Phe Arg Ile
    290                 295                 300

Thr Ile Leu Pro Gln Gln Tyr Leu Arg Pro Val Glu Asp Val Ala Thr
305                 310                 315                 320

Ser Gln Asp Asp Cys Tyr Lys Phe Ala Ile Ser Gln Ser Ser Thr Gly
                325                 330                 335

Thr Val Met Gly Ala Val Ile Met Glu Gly Phe Tyr Val Val Phe Asp
            340                 345                 350
```

```
Arg Ala Arg Lys Arg Ile Gly Phe Ala Val Ser Ala Cys His Val His
            355                 360                 365

Asp Glu Phe Arg Thr Ala Ala Val Glu Gly Pro Phe Val Thr Leu Asp
        370                 375                 380

Met Glu Asp Cys Gly Tyr Asn Ile Pro Gln Thr Asp Glu Ser Arg Ser
385                 390                 395                 400

His His His His His His
            405

<210> SEQ ID NO 4
<211> LENGTH: 1368
<212> TYPE: DNA
<213> ORGANISM: Homo sapiens
<220> FEATURE:
<221> NAME/KEY: CDS
<222> LOCATION: (1)..(1368)

<400> SEQUENCE: 4 atg gct agc atg act ggt gga cag caa atg ggt cgc gga tcc atg gct      48
Met Ala Ser Met Thr Gly Gly Gln Gln Met Gly Arg Gly Ser Met Ala
1               5                   10                  15 ggt gtt ctg cca gct cac ggt acc caa cat ggt att cgt ctg cca ctg      96
Gly Val Leu Pro Ala His Gly Thr Gln His Gly Ile Arg Leu Pro Leu
            20                  25                  30 cgt agc ggt ctg ggt ggt gct cca ctg ggt ctg cgt ctg ccc cgg gag     144
Arg Ser Gly Leu Gly Gly Ala Pro Leu Gly Leu Arg Leu Pro Arg Glu
        35                  40                  45 acc gac gaa gag ccc gag gag ccc ggc cgg agg ggc agc ttt gtg gag     192
Thr Asp Glu Glu Pro Glu Glu Pro Gly Arg Arg Gly Ser Phe Val Glu
    50                  55                  60 atg gtg gac aac ctg agg ggc aag tcg ggg cag ggc tac tac gtg gag     240
Met Val Asp Asn Leu Arg Gly Lys Ser Gly Gln Gly Tyr Tyr Val Glu
65                  70                  75                  80 atg acc gtg ggc agc ccc ccg cag acg ctc aac atc ctg gtg gat aca     288
Met Thr Val Gly Ser Pro Pro Gln Thr Leu Asn Ile Leu Val Asp Thr
                85                  90                  95 ggc agc agt aac ttt gca gtg ggt gct gcc ccc cac ccc ttc ctg cat     336
Gly Ser Ser Asn Phe Ala Val Gly Ala Ala Pro His Pro Phe Leu His
            100                 105                 110 cgc tac tac cag agg cag ctg tcc agc aca tac cgg gac ctc cgg aag     384
Arg Tyr Tyr Gln Arg Gln Leu Ser Ser Thr Tyr Arg Asp Leu Arg Lys
        115                 120                 125 ggc gtg tat gtg ccc tac acc cag ggc aag tgg gaa ggg gag ctg ggc     432
Gly Val Tyr Val Pro Tyr Thr Gln Gly Lys Trp Glu Gly Glu Leu Gly
    130                 135                 140 acc gac ctg gta agc atc ccc cat ggc ccc aac gtc act gtg cgt gcc     480
Thr Asp Leu Val Ser Ile Pro His Gly Pro Asn Val Thr Val Arg Ala
145                 150                 155                 160 aac att gct gcc atc act gaa tca gac aag ttc ttc atc aac ggc tcc     528
Asn Ile Ala Ala Ile Thr Glu Ser Asp Lys Phe Phe Ile Asn Gly Ser
                165                 170                 175 aac tgg gaa ggc atc ctg ggg ctg gcc tat gct gag att gcc agg cct     576
Asn Trp Glu Gly Ile Leu Gly Leu Ala Tyr Ala Glu Ile Ala Arg Pro
            180                 185                 190 gac gac tcc ctg gag cct ttc ttt gac tct ctg gta aag cag acc cac     624
Asp Asp Ser Leu Glu Pro Phe Phe Asp Ser Leu Val Lys Gln Thr His
        195                 200                 205 gtt ccc aac ctc ttc tcc ctg cag ctt tgt ggt gct ggc ttc ccc ctc     672
Val Pro Asn Leu Phe Ser Leu Gln Leu Cys Gly Ala Gly Phe Pro Leu
    210                 215                 220
```

```
aac cag tct gaa gtg ctg gcc tct gtc gga ggg agc atg atc att gga        720
Asn Gln Ser Glu Val Leu Ala Ser Val Gly Gly Ser Met Ile Ile Gly
225                 230                 235                 240 ggt atc gac cac tcg ctg tac aca ggc agt ctc tgg tat aca ccc atc        768
Gly Ile Asp His Ser Leu Tyr Thr Gly Ser Leu Trp Tyr Thr Pro Ile
                245                 250                 255 cgg cgg gag tgg tat tat gag gtc atc att gtg cgg gtg gag atc aat        816
Arg Arg Glu Trp Tyr Tyr Glu Val Ile Ile Val Arg Val Glu Ile Asn
        260                 265                 270 gga cag gat ctg aaa atg gac tgc aag gag tac aac tat gac aag agc        864
Gly Gln Asp Leu Lys Met Asp Cys Lys Glu Tyr Asn Tyr Asp Lys Ser
    275                 280                 285 att gtg gac agt ggc acc acc aac ctt cgt ttg ccc aag aaa gtg ttt        912
Ile Val Asp Ser Gly Thr Thr Asn Leu Arg Leu Pro Lys Lys Val Phe
290                 295                 300 gaa gct gca gtc aaa tcc atc aag gca gcc tcc tcc acg gag aag ttc        960
Glu Ala Ala Val Lys Ser Ile Lys Ala Ala Ser Ser Thr Glu Lys Phe
305                 310                 315                 320 cct gat ggt ttc tgg cta gga gag cag ctg gtg tgc tgg caa gca ggc       1008
Pro Asp Gly Phe Trp Leu Gly Glu Gln Leu Val Cys Trp Gln Ala Gly
                325                 330                 335 acc acc cct tgg aac att ttc cca gtc atc tca ctc tac cta atg ggt       1056
Thr Thr Pro Trp Asn Ile Phe Pro Val Ile Ser Leu Tyr Leu Met Gly
        340                 345                 350 gag gtt acc aac cag tcc ttc cgc atc acc atc ctt ccg cag caa tac       1104
Glu Val Thr Asn Gln Ser Phe Arg Ile Thr Ile Leu Pro Gln Gln Tyr
    355                 360                 365 ctg cgg cca gtg gaa gat gtg gcc acg tcc caa gac gac tgt tac aag       1152
Leu Arg Pro Val Glu Asp Val Ala Thr Ser Gln Asp Asp Cys Tyr Lys
370                 375                 380 ttt gcc atc tca cag tca tcc acg ggc act gtt atg gga gct gtt atc       1200
Phe Ala Ile Ser Gln Ser Ser Thr Gly Thr Val Met Gly Ala Val Ile
385                 390                 395                 400 atg gag ggc ttc tac gtt gtc ttt gat cgg gcc cga aaa cga att ggc       1248
Met Glu Gly Phe Tyr Val Val Phe Asp Arg Ala Arg Lys Arg Ile Gly
                405                 410                 415 ttt gct gtc agc gct tgc cat gtg cac gat gag ttc agg acg gca gcg       1296
Phe Ala Val Ser Ala Cys His Val His Asp Glu Phe Arg Thr Ala Ala
        420                 425                 430 gtg gaa ggc cct ttt gtc acc ttg gac atg gaa gac tgt ggc tac aac       1344
Val Glu Gly Pro Phe Val Thr Leu Asp Met Glu Asp Cys Gly Tyr Asn
    435                 440                 445 att cca cag aca gat gag tca tag                                       1368
Ile Pro Gln Thr Asp Glu Ser
    450                 455

<210> SEQ ID NO 5
<211> LENGTH: 455
<212> TYPE: PRT
<213> ORGANISM: Homo sapiens

<400> SEQUENCE: 5

Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Pro Gly Arg Arg Gly Ser Phe Val Glu
```

```
            50                  55                  60
Met Val Asp Asn Leu Arg Gly Lys Ser Gly Gln Gly Tyr Tyr Val Glu
 65                  70                  75                  80

Met Thr Val Gly Ser Pro Pro Gln Thr Leu Asn Ile Leu Val Asp Thr
                 85                  90                  95

Gly Ser Ser Asn Phe Ala Val Gly Ala Ala Pro His Pro Phe Leu His
                100                 105                 110

Arg Tyr Tyr Gln Arg Gln Leu Ser Ser Thr Tyr Arg Asp Leu Arg Lys
                115                 120                 125

Gly Val Tyr Val Pro Tyr Thr Gln Gly Lys Trp Glu Gly Glu Leu Gly
130                 135                 140

Thr Asp Leu Val Ser Ile Pro His Gly Pro Asn Val Thr Val Arg Ala
145                 150                 155                 160

Asn Ile Ala Ala Ile Thr Glu Ser Asp Lys Phe Phe Ile Asn Gly Ser
                165                 170                 175

Asn Trp Glu Gly Ile Leu Gly Leu Ala Tyr Ala Glu Ile Ala Arg Pro
                180                 185                 190

Asp Asp Ser Leu Glu Pro Phe Phe Asp Ser Leu Val Lys Gln Thr His
                195                 200                 205

Val Pro Asn Leu Phe Ser Leu Gln Leu Cys Gly Ala Gly Phe Pro Leu
210                 215                 220

Asn Gln Ser Glu Val Leu Ala Ser Val Gly Gly Ser Met Ile Ile Gly
225                 230                 235                 240

Gly Ile Asp His Ser Leu Tyr Thr Gly Ser Leu Trp Tyr Thr Pro Ile
                245                 250                 255

Arg Arg Glu Trp Tyr Tyr Glu Val Ile Ile Val Arg Val Glu Ile Asn
                260                 265                 270

Gly Gln Asp Leu Lys Met Asp Cys Lys Glu Tyr Asn Tyr Asp Lys Ser
                275                 280                 285

Ile Val Asp Ser Gly Thr Thr Asn Leu Arg Leu Pro Lys Lys Val Phe
                290                 295                 300

Glu Ala Ala Val Lys Ser Ile Lys Ala Ala Ser Ser Thr Glu Lys Phe
305                 310                 315                 320

Pro Asp Gly Phe Trp Leu Gly Glu Gln Leu Val Cys Trp Gln Ala Gly
                325                 330                 335

Thr Thr Pro Trp Asn Ile Phe Pro Val Ile Ser Leu Tyr Leu Met Gly
                340                 345                 350

Glu Val Thr Asn Gln Ser Phe Arg Ile Thr Ile Leu Pro Gln Gln Tyr
                355                 360                 365

Leu Arg Pro Val Glu Asp Val Ala Thr Ser Gln Asp Asp Cys Tyr Lys
370                 375                 380

Phe Ala Ile Ser Gln Ser Ser Thr Gly Thr Val Met Gly Ala Val Ile
385                 390                 395                 400

Met Glu Gly Phe Tyr Val Val Phe Asp Arg Ala Arg Lys Arg Ile Gly
                405                 410                 415

Phe Ala Val Ser Ala Cys His Val His Asp Glu Phe Arg Thr Ala Ala
                420                 425                 430

Val Glu Gly Pro Phe Val Thr Leu Asp Met Glu Asp Cys Gly Tyr Asn
                435                 440                 445

Ile Pro Gln Thr Asp Glu Ser
                450                 455

<210> SEQ ID NO 6
```

```
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 6 atg aga gga tcg cat cac cat cac cat cac gga tcc atc gag acc gac      48
Met Arg Gly Ser His His His His His His Gly Ser Ile Glu Thr Asp
1               5                   10                  15 acc caa cat ggt att cgt ctg cca ctg cgt agc ggt ctg ggt ggt gct      96
Thr Gln His Gly Ile Arg Leu Pro Leu Arg Ser Gly Leu Gly Gly Ala
                20                  25                  30 cca ctg ggt ctg cgt ctg ccc cgg gag acc gac gaa gag ccc gag gag     144
Pro Leu Gly Leu Arg Leu Pro Arg Glu Thr Asp Glu Glu Pro Glu Glu
            35                  40                  45 ccc ggc cgg agg ggc agc ttt gtg gag atg gtg gac aac ctg agg ggc     192
Pro Gly Arg Arg Gly Ser Phe Val Glu Met Val Asp Asn Leu Arg Gly
        50                  55                  60 aag tcg ggg cag ggc tac tac gtg gag atg acc gtg ggc agc ccc ccg     240
Lys Ser Gly Gln Gly Tyr Tyr Val Glu Met Thr Val Gly Ser Pro Pro
65                  70                  75                  80 cag acg ctc aac atc ctg gtg gat aca ggc agc agt aac ttt gca gtg     288
Gln Thr Leu Asn Ile Leu Val Asp Thr Gly Ser Ser Asn Phe Ala Val
                85                  90                  95 ggt gct gcc ccc cac ccc ttc ctg cat cgc tac tac cag agg cag ctg     336
Gly Ala Ala Pro His Pro Phe Leu His Arg Tyr Tyr Gln Arg Gln Leu
                100                 105                 110 tcc agc aca tac cgg gac ctc cgg aag ggc gtg tat gtg ccc tac acc     384
Ser Ser Thr Tyr Arg Asp Leu Arg Lys Gly Val Tyr Val Pro Tyr Thr
            115                 120                 125 cag ggc aag tgg gaa ggg gag ctg ggc acc gac ctg gta agc atc ccc     432
Gln Gly Lys Trp Glu Gly Glu Leu Gly Thr Asp Leu Val Ser Ile Pro
        130                 135                 140 cat ggc ccc aac gtc act gtg cgt gcc aac att gct gcc atc act gaa     480
His Gly Pro Asn Val Thr Val Arg Ala Asn Ile Ala Ala Ile Thr Glu
145                 150                 155                 160 tca gac aag ttc ttc atc aac ggc tcc aac tgg gaa ggc atc ctg ggg     528
Ser Asp Lys Phe Phe Ile Asn Gly Ser Asn Trp Glu Gly Ile Leu Gly
                165                 170                 175 ctg gcc tat gct gag att gcc agg cct gac gac tcc ctg gag cct ttc     576
Leu Ala Tyr Ala Glu Ile Ala Arg Pro Asp Asp Ser Leu Glu Pro Phe
                180                 185                 190 ttt gac tct ctg gta aag cag acc cac gtt ccc aac ctc ttc tcc ctg     624
Phe Asp Ser Leu Val Lys Gln Thr His Val Pro Asn Leu Phe Ser Leu
            195                 200                 205 cag ctt tgt ggt gct ggc ttc ccc ctc aac cag tct gaa gtg ctg gcc     672
Gln Leu Cys Gly Ala Gly Phe Pro Leu Asn Gln Ser Glu Val Leu Ala
        210                 215                 220 tct gtc gga ggg agc atg atc att gga ggt atc gac cac tcg ctg tac     720
Ser Val Gly Gly Ser Met Ile Ile Gly Gly Ile Asp His Ser Leu Tyr
225                 230                 235                 240 aca ggc agt ctc tgg tat aca ccc atc cgg cgg gag tgg tat tat gag     768
Thr Gly Ser Leu Trp Tyr Thr Pro Ile Arg Arg Glu Trp Tyr Tyr Glu
                245                 250                 255 gtc atc att gtg cgg gtg gag atc aat gga cag gat ctg aaa atg gac     816
Val Ile Ile Val Arg Val Glu Ile Asn Gly Gln Asp Leu Lys Met Asp
                260                 265                 270 tgc aag gag tac aac tat gac aag agc att gtg gac agt ggc acc acc     864
Cys Lys Glu Tyr Asn Tyr Asp Lys Ser Ile Val Asp Ser Gly Thr Thr
```

-continued

```
                 275                 280                 285
aac ctt cgt ttg ccc aag aaa gtg ttt gaa gct gca gtc aaa tcc atc       912
Asn Leu Arg Leu Pro Lys Lys Val Phe Glu Ala Ala Val Lys Ser Ile
    290                 295                 300 aag gca gcc tcc tcc acg gag aag ttc cct gat ggt ttc tgg cta gga       960
Lys Ala Ala Ser Ser Thr Glu Lys Phe Pro Asp Gly Phe Trp Leu Gly
305                 310                 315                 320 gag cag ctg gtg tgc tgg caa gca ggc acc acc cct tgg aac att ttc      1008
Glu Gln Leu Val Cys Trp Gln Ala Gly Thr Thr Pro Trp Asn Ile Phe
                325                 330                 335 cca gtc atc tca ctc tac cta atg ggt gag gtt acc aac cag tcc ttc      1056
Pro Val Ile Ser Leu Tyr Leu Met Gly Glu Val Thr Asn Gln Ser Phe
            340                 345                 350 cgc atc acc atc ctt ccg cag caa tac ctg cgg cca gtg gaa gat gtg      1104
Arg Ile Thr Ile Leu Pro Gln Gln Tyr Leu Arg Pro Val Glu Asp Val
        355                 360                 365 gcc acg tcc caa gac gac tgt tac aag ttt gcc atc tca cag tca tcc      1152
Ala Thr Ser Gln Asp Asp Cys Tyr Lys Phe Ala Ile Ser Gln Ser Ser
    370                 375                 380 acg ggc act gtt atg gga gct gtt atc atg gag ggc ttc tac gtt gtc      1200
Thr Gly Thr Val Met Gly Ala Val Ile Met Glu Gly Phe Tyr Val Val
385                 390                 395                 400 ttt gat cgg gcc cga aaa cga att ggc ttt gct gtc agc gct tgc cat      1248
Phe Asp Arg Ala Arg Lys Arg Ile Gly Phe Ala Val Ser Ala Cys His
                405                 410                 415 gtg cac gat gag ttc agg acg gca gcg gtg gaa ggc cct ttt gtc acc      1296
Val His Asp Glu Phe Arg Thr Ala Ala Val Glu Gly Pro Phe Val Thr
            420                 425                 430 ttg gac atg gaa gac tgt ggc tac aac att cca cag aca gat gag tca      1344
Leu Asp Met Glu Asp Cys Gly Tyr Asn Ile Pro Gln Thr Asp Glu Ser
        435                 440                 445 tga                                                                   1347

<210> SEQ ID NO 7
<211> LENGTH: 448
<212> TYPE: PRT
<213> ORGANISM: Homo sapiens

<400> SEQUENCE: 7

Met Arg Gly Ser His His His His His His Gly Ser Ile Glu Thr Asp
1               5                   10                  15

Thr Gln His Gly Ile Arg Leu Pro Leu Arg Ser Gly Leu Gly Gly Ala
            20                  25                  30

Pro Leu Gly Leu Arg Leu Pro Arg Glu Thr Asp Glu Glu Pro Glu Glu
        35                  40                  45

Pro Gly Arg Arg Gly Ser Phe Val Glu Met Val Asp Asn Leu Arg Gly
    50                  55                  60

Lys Ser Gly Gln Gly Tyr Tyr Val Glu Met Thr Val Gly Ser Pro Pro
65                  70                  75                  80

Gln Thr Leu Asn Ile Leu Val Asp Thr Gly Ser Ser Asn Phe Ala Val
                85                  90                  95

Gly Ala Ala Pro His Pro Phe Leu His Arg Tyr Tyr Gln Arg Gln Leu
            100                 105                 110

Ser Ser Thr Tyr Arg Asp Leu Arg Lys Gly Val Tyr Val Pro Tyr Thr
        115                 120                 125

Gln Gly Lys Trp Glu Gly Glu Leu Gly Thr Asp Leu Val Ser Ile Pro
    130                 135                 140
```

His Gly Pro Asn Val Thr Val Arg Ala Asn Ile Ala Ala Ile Thr Glu
145                 150                 155                 160

Ser Asp Lys Phe Phe Ile Asn Gly Ser Asn Trp Glu Gly Ile Leu Gly
            165                 170                 175

Leu Ala Tyr Ala Glu Ile Ala Arg Pro Asp Ser Leu Glu Pro Phe
        180                 185                 190

Phe Asp Ser Leu Val Lys Gln Thr His Val Pro Asn Leu Phe Ser Leu
        195                 200                 205

Gln Leu Cys Gly Ala Gly Phe Pro Leu Asn Gln Ser Glu Val Leu Ala
        210                 215                 220

Ser Val Gly Gly Ser Met Ile Ile Gly Gly Ile Asp His Ser Leu Tyr
225                 230                 235                 240

Thr Gly Ser Leu Trp Tyr Thr Pro Ile Arg Arg Glu Trp Tyr Tyr Glu
                245                 250                 255

Val Ile Ile Val Arg Val Glu Ile Asn Gly Gln Asp Leu Lys Met Asp
            260                 265                 270

Cys Lys Glu Tyr Asn Tyr Asp Lys Ser Ile Val Asp Ser Gly Thr Thr
        275                 280                 285

Asn Leu Arg Leu Pro Lys Lys Val Phe Glu Ala Ala Val Lys Ser Ile
        290                 295                 300

Lys Ala Ala Ser Ser Thr Glu Lys Phe Pro Asp Gly Phe Trp Leu Gly
305                 310                 315                 320

Glu Gln Leu Val Cys Trp Gln Ala Gly Thr Thr Pro Trp Asn Ile Phe
                325                 330                 335

Pro Val Ile Ser Leu Tyr Leu Met Gly Glu Val Thr Asn Gln Ser Phe
            340                 345                 350

Arg Ile Thr Ile Leu Pro Gln Gln Tyr Leu Arg Pro Val Glu Asp Val
        355                 360                 365

Ala Thr Ser Gln Asp Asp Cys Tyr Lys Phe Ala Ile Ser Gln Ser Ser
        370                 375                 380

Thr Gly Thr Val Met Gly Ala Val Ile Met Glu Gly Phe Tyr Val Val
385                 390                 395                 400

Phe Asp Arg Ala Arg Lys Arg Ile Gly Phe Ala Val Ser Ala Cys His
                405                 410                 415

Val His Asp Glu Phe Arg Thr Ala Ala Val Glu Gly Pro Phe Val Thr
            420                 425                 430

Leu Asp Met Glu Asp Cys Gly Tyr Asn Ile Pro Gln Thr Asp Glu Ser
        435                 440                 445

<210> SEQ ID NO 8
<211> LENGTH: 12
<212> TYPE: PRT
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: T7- Tag

<400> SEQUENCE: 8

Met Ala Ser Met Thr Gly Gly Gln Gln Met Gly Arg
1               5                   10

<210> SEQ ID NO 9
<211> LENGTH: 13
<212> TYPE: PRT
<213> ORGANISM: Artificial
<220> FEATURE:

-continued

```
<223> OTHER INFORMATION: Artificial Sequence
<220> FEATURE:
<221> NAME/KEY: misc_feature
<223> OTHER INFORMATION: Synthetic Peptide Substrate for BACE

<400> SEQUENCE: 9

Ser Glu Ile Ser Tyr Glu Val Glu Phe Arg Trp Lys Lys
1               5                   10

<210> SEQ ID NO 10
<211> LENGTH: 23
<212> TYPE: PRT
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Synthetic Peptide Substrate for BACE

<400> SEQUENCE: 10

Gly Leu Thr Asn Ile Lys Thr Glu Glu Ile Ser Glu Ile Ser Tyr Glu
1               5                   10                  15

Val Glu Phe Arg Trp Lys Lys
            20

<210> SEQ ID NO 11
<211> LENGTH: 13
<212> TYPE: PRT
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Synthetic Substrate for BACE

<400> SEQUENCE: 11

Ser Glu Val Asn Leu Asp Ala Glu Phe Arg Trp Lys Lys
1               5                   10

<210> SEQ ID NO 12
<211> LENGTH: 23
<212> TYPE: PRT
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Synthetic Peptide Substrate for BACE

<400> SEQUENCE: 12

Gly Leu Thr Asn Ile Lys Thr Glu Glu Ile Ser Glu Val Asn Leu Asp
1               5                   10                  15

Ala Glu Phe Arg Trp Lys Lys
            20

<210> SEQ ID NO 13
<211> LENGTH: 12
<212> TYPE: PRT
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Synthetic Peptide Substrate for BACE

<400> SEQUENCE: 13

Glu Ile Asp Leu Met Val Leu Asp Trp His Asp Arg
1               5                   10
```

<210> SEQ ID NO 14
<211> LENGTH: 33
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE N-terminal forward primer
      for recombinant pET11a-BACE

<400> SEQUENCE: 14
ggcaggatcc atggctggtg ttctgccagc tca                           33

<210> SEQ ID NO 15
<211> LENGTH: 20
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE N-terminal reverse primer
      for recombinant pET11a-BACE

<400> SEQUENCE: 15
tgccactgtc cacaatgctc                                          20

<210> SEQ ID NO 16
<211> LENGTH: 33
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE C-terminal reverse primer for
      recombinant pET11a-BACE

<400> SEQUENCE: 16
ggcaggatcc tatgactcat ctgtctgtgg aat                           33

<210> SEQ ID NO 17
<211> LENGTH: 20
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE C-terminal forward primer
      for recombinant pET11a-BACE

<400> SEQUENCE: 17
gagcattgtg gacagtggca                                          20

<210> SEQ ID NO 18
<211> LENGTH: 45
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE primer for recombinant pQE80L-BACE

<400> SEQUENCE: 18
gctaaggatc catcgagacc gacacccaac atggtattcg tctgc              45

<210> SEQ ID NO 19
<211> LENGTH: 20
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE forward primer for recombinant pQE80L-BACE

<400> SEQUENCE: 19
gctaaggatc catcgagacc                                        20

<210> SEQ ID NO 20
<211> LENGTH: 35
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE reverse primer for recombinant pQE80L-BACE

<400> SEQUENCE: 20
ggcaagctta tcatgactca tctgtctgtg gaatg                       35

<210> SEQ ID NO 21
<211> LENGTH: 34
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE forward primer for recombinant pQE70-BACE

<400> SEQUENCE: 21
ggctgcatgc gtggcagctt tgtggagatg gtgg                        34

<210> SEQ ID NO 22
<211> LENGTH: 30
<212> TYPE: DNA
<213> ORGANISM: Artificial
<220> FEATURE:
<223> OTHER INFORMATION: Artificial Sequence
<220> FEATURE:
<221> NAME/KEY: misc_feature
<223> OTHER INFORMATION: Primer: BACE reverse primer for recombinant pQE70-BACE

<400> SEQUENCE: 22
ggctagatct tgactcatct gtctgtggaa                             30

<210> SEQ ID NO 23
<211> LENGTH: 459
<212> TYPE: PRT
<213> ORGANISM: Homo sapiens
<220> FEATURE:
<221> NAME/KEY: MISC_FEATURE
<223> OTHER INFORMATION: Human soluble BACE with 6-His tag

<400> SEQUENCE: 23

Met Ala Gln Ala Leu Pro Trp Leu Leu Leu Trp Met Gly Ala Gly Val
1               5                   10                  15

-continued

```
Leu Pro Ala His Gly Thr Gln His Gly Ile Arg Leu Pro Leu Arg Ser
             20                  25                  30
Gly Leu Gly Gly Ala Pro Leu Gly Leu Arg Leu Pro Arg Glu Thr Asp
             35                  40                  45
Glu Glu Pro Glu Pro Gly Arg Arg Gly Ser Phe Val Glu Met Val
 50                  55                  60
Asp Asn Leu Arg Gly Lys Ser Gly Gln Gly Tyr Tyr Val Glu Met Thr
 65                  70                  75                  80
Val Gly Ser Pro Pro Gln Thr Leu Asn Ile Leu Val Asp Thr Gly Ser
             85                  90                  95
Ser Asn Phe Ala Val Gly Ala Ala Pro His Pro Phe Leu His Arg Tyr
            100                 105                 110
Tyr Gln Arg Gln Leu Ser Ser Thr Tyr Arg Asp Leu Arg Lys Gly Val
            115                 120                 125
Tyr Val Pro Tyr Thr Gln Gly Lys Trp Glu Gly Glu Leu Gly Thr Asp
            130                 135                 140
Leu Val Ser Ile Pro His Gly Pro Asn Val Thr Val Arg Ala Asn Ile
145                 150                 155                 160
Ala Ala Ile Thr Glu Ser Asp Lys Phe Phe Ile Asn Gly Ser Asn Trp
            165                 170                 175
Glu Gly Ile Leu Gly Leu Ala Tyr Ala Glu Ile Ala Arg Pro Asp Asp
            180                 185                 190
Ser Leu Glu Pro Phe Phe Asp Ser Leu Val Lys Gln Thr His Val Pro
            195                 200                 205
Asn Leu Phe Ser Leu Gln Leu Cys Gly Ala Gly Phe Pro Leu Asn Gln
            210                 215                 220
Ser Glu Val Leu Ala Ser Val Gly Gly Ser Met Ile Ile Gly Gly Ile
225                 230                 235                 240
Asp His Ser Leu Tyr Thr Gly Ser Leu Trp Tyr Thr Pro Ile Arg Arg
            245                 250                 255
Glu Trp Tyr Tyr Glu Val Ile Ile Val Arg Val Glu Ile Asn Gly Gln
            260                 265                 270
Asp Leu Lys Met Asp Cys Lys Glu Tyr Asn Tyr Asp Lys Ser Ile Val
            275                 280                 285
Asp Ser Gly Thr Thr Asn Leu Arg Leu Pro Lys Lys Val Phe Glu Ala
            290                 295                 300
Ala Val Lys Ser Ile Lys Ala Ala Ser Ser Thr Glu Lys Phe Pro Asp
305                 310                 315                 320
Gly Phe Trp Leu Gly Glu Gln Leu Val Cys Trp Gln Ala Gly Thr Thr
            325                 330                 335
Pro Trp Asn Ile Phe Pro Val Ile Ser Leu Tyr Leu Met Gly Glu Val
            340                 345                 350
Thr Asn Gln Ser Phe Arg Ile Thr Ile Leu Pro Gln Gln Tyr Leu Arg
            355                 360                 365
Pro Val Glu Asp Val Ala Thr Ser Gln Asp Asp Cys Tyr Lys Phe Ala
            370                 375                 380
Ile Ser Gln Ser Ser Thr Gly Thr Val Met Gly Ala Val Ile Met Glu
385                 390                 395                 400
Gly Phe Tyr Val Val Phe Asp Arg Ala Arg Lys Arg Ile Gly Phe Ala
            405                 410                 415
Val Ser Ala Cys His Val His Asp Glu Phe Arg Thr Ala Ala Val Glu
            420                 425                 430
Gly Pro Phe Val Thr Leu Asp Met Glu Asp Cys Gly Tyr Asn Ile Pro
```

```
                    435                 440                 445
Gln Thr Asp Glu Ser His His His His His
        450                 455

<210> SEQ ID NO 24
<211> LENGTH: 1293
<212> TYPE: DNA
<213> ORGANISM: Homo sapiens
<220> FEATURE:
<221> NAME/KEY: CDS
<222> LOCATION: (1)..(1293)

<400> SEQUENCE: 24 atg gct agc atg act ggt gga cag caa atg ggt cgc gga tcc atg gct      48
Met Ala Ser Met Thr Gly Gly Gln Gln Met Gly Arg Gly Ser Met Ala
1               5                   10                  15 ggt gtt ctg cca gct cac ggt acc caa cat ggt att cgt ctg cca ctg      96
Gly Val Leu Pro Ala His Gly Thr Gln His Gly Ile Arg Leu Pro Leu
            20                  25                  30 cgt agc ggt ctg ggt ggt gct cca ctg ggt ctg cgt ctg ccc cgg gag     144
Arg Ser Gly Leu Gly Gly Ala Pro Leu Gly Leu Arg Leu Pro Arg Glu
        35                  40                  45 acc gac gaa gag ccc gag gag ccc ggc cgg agg ggc agc ttt gtg gag     192
Thr Asp Glu Glu Pro Glu Glu Pro Gly Arg Arg Gly Ser Phe Val Glu
    50                  55                  60 atg gtg gac aac ctg agg ggc aag tcg ggg cag ggc tac tac gtg gag     240
Met Val Asp Asn Leu Arg Gly Lys Ser Gly Gln Gly Tyr Tyr Val Glu
65                  70                  75                  80 atg acc gtg ggc agc ccc ccg cag acg ctc aac atc ctg gtg gat aca     288
Met Thr Val Gly Ser Pro Pro Gln Thr Leu Asn Ile Leu Val Asp Thr
                85                  90                  95 ggc agc agt aac ttt gca gtg ggt gct gcc ccc cac ccc ttc ctg cat     336
Gly Ser Ser Asn Phe Ala Val Gly Ala Ala Pro His Pro Phe Leu His
            100                 105                 110 cgc tac tac cag agg cag ctg tcc agc aca tac cgg gac ctc cgg aag     384
Arg Tyr Tyr Gln Arg Gln Leu Ser Ser Thr Tyr Arg Asp Leu Arg Lys
        115                 120                 125 ggc gtg tat gtg ccc tac acc cag ggc aag tgg gaa ggg gag ctg ggc     432
Gly Val Tyr Val Pro Tyr Thr Gln Gly Lys Trp Glu Gly Glu Leu Gly
    130                 135                 140 acc gac ctg gta agc atc ccc cat ggc ccc aac gtc act gtg cgt gcc     480
Thr Asp Leu Val Ser Ile Pro His Gly Pro Asn Val Thr Val Arg Ala
145                 150                 155                 160 aac att gct gcc atc act gaa tca gac aag ttc ttc atc aac ggc tcc     528
Asn Ile Ala Ala Ile Thr Glu Ser Asp Lys Phe Phe Ile Asn Gly Ser
                165                 170                 175 aac tgg gaa ggc atc ctg ggg ctg gcc tat gct gag att gcc agg ctt     576
Asn Trp Glu Gly Ile Leu Gly Leu Ala Tyr Ala Glu Ile Ala Arg Leu
            180                 185                 190 tgt ggt gct ggc ttc ccc ctc aac cag tct gaa gtg ctg gcc tct gtc     624
Cys Gly Ala Gly Phe Pro Leu Asn Gln Ser Glu Val Leu Ala Ser Val
        195                 200                 205 gga ggg agc atg atc att gga ggt atc gac cac tcg ctg tac aca ggc     672
Gly Gly Ser Met Ile Ile Gly Gly Ile Asp His Ser Leu Tyr Thr Gly
    210                 215                 220 agt ctc tgg tat aca ccc atc cgg cgg gag tgg tat tat gag gtc atc     720
Ser Leu Trp Tyr Thr Pro Ile Arg Arg Glu Trp Tyr Tyr Glu Val Ile
225                 230                 235                 240 att gtg cgg gtg gag atc aat gga cag gat ctg aaa atg gac tgc aag     768
Ile Val Arg Val Glu Ile Asn Gly Gln Asp Leu Lys Met Asp Cys Lys
                245                 250                 255
```

```
gag tac aac tat gac aag agc att gtg gac agt ggc acc acc aac ctt      816
Glu Tyr Asn Tyr Asp Lys Ser Ile Val Asp Ser Gly Thr Thr Asn Leu
            260                 265                 270 cgt ttg ccc aag aaa gtg ttt gaa gct gca gtc aaa tcc atc aag gca      864
Arg Leu Pro Lys Lys Val Phe Glu Ala Ala Val Lys Ser Ile Lys Ala
            275                 280                 285 gcc tcc tcc acg gag aag ttc cct gat ggt ttc tgg cta gga gag cag      912
Ala Ser Ser Thr Glu Lys Phe Pro Asp Gly Phe Trp Leu Gly Glu Gln
        290                 295                 300 ctg gtg tgc tgg caa gca ggc acc acc cct tgg aac att ttc cca gtc      960
Leu Val Cys Trp Gln Ala Gly Thr Thr Pro Trp Asn Ile Phe Pro Val
305                 310                 315                 320 atc tca ctc tac cta atg ggt gag gtt acc aac cag tcc ttc cgc atc     1008
Ile Ser Leu Tyr Leu Met Gly Glu Val Thr Asn Gln Ser Phe Arg Ile
                325                 330                 335 acc atc ctt ccg cag caa tac ctg cgg cca gtg gaa gat gtg gcc acg     1056
Thr Ile Leu Pro Gln Gln Tyr Leu Arg Pro Val Glu Asp Val Ala Thr
            340                 345                 350 tcc caa gac gac tgt tac aag ttt gcc atc tca cag tca tcc acg ggc     1104
Ser Gln Asp Asp Cys Tyr Lys Phe Ala Ile Ser Gln Ser Ser Thr Gly
        355                 360                 365 act gtt atg gga gct gtt atc atg gag ggc ttc tac gtt gtc ttt gat     1152
Thr Val Met Gly Ala Val Ile Met Glu Gly Phe Tyr Val Val Phe Asp
370                 375                 380 cgg gcc cga aaa cga att ggc ttt gct gtc agc gct tgc cat gtg cac     1200
Arg Ala Arg Lys Arg Ile Gly Phe Ala Val Ser Ala Cys His Val His
385                 390                 395                 400 gat gag ttc agg acg gca gcg gtg gaa ggc cct ttt gtc acc ttg gac     1248
Asp Glu Phe Arg Thr Ala Ala Val Glu Gly Pro Phe Val Thr Leu Asp
                405                 410                 415 atg gaa gac tgt ggc tac aac att cca cag aca gat gag tca tag         1293
Met Glu Asp Cys Gly Tyr Asn Ile Pro Gln Thr Asp Glu Ser
            420                 425                 430

<210> SEQ ID NO 25
<211> LENGTH: 430
<212> TYPE: PRT
<213> ORGANISM: Homo sapiens

<400> SEQUENCE: 25

Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Pro Gly Arg Arg Gly Ser Phe Val Glu
    50                  55                  60

Met Val Asp Asn Leu Arg Gly Lys Ser Gly Gln Gly Tyr Tyr Val Glu
65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His
            100                 105                 110

Arg Tyr Tyr Gln Arg Gln Leu Ser Ser Thr Tyr Arg Asp Leu Arg Lys
        115                 120                 125

Gly Val Tyr Val Pro Tyr Thr Gln Gly Lys Trp Glu Gly Glu Leu Gly
    130                 135                 140
```

```
Thr Asp Leu Val Ser Ile Pro His Gly Pro Asn Val Thr Val Arg Ala
145                 150                 155                 160

Asn Ile Ala Ala Ile Thr Glu Ser Asp Lys Phe Phe Ile Asn Gly Ser
            165                 170                 175

Asn Trp Glu Gly Ile Leu Gly Leu Ala Tyr Ala Glu Ile Ala Arg Leu
        180                 185                 190

Cys Gly Ala Gly Phe Pro Leu Asn Gln Ser Glu Val Leu Ala Ser Val
    195                 200                 205

Gly Gly Ser Met Ile Ile Gly Gly Ile Asp His Ser Leu Tyr Thr Gly
    210                 215                 220

Ser Leu Trp Tyr Thr Pro Ile Arg Arg Glu Trp Tyr Tyr Glu Val Ile
225                 230                 235                 240

Ile Val Arg Val Glu Ile Asn Gly Gln Asp Leu Lys Met Asp Cys Lys
                245                 250                 255

Glu Tyr Asn Tyr Asp Lys Ser Ile Val Asp Ser Gly Thr Thr Asn Leu
            260                 265                 270

Arg Leu Pro Lys Lys Val Phe Glu Ala Ala Val Lys Ser Ile Lys Ala
        275                 280                 285

Ala Ser Ser Thr Glu Lys Phe Pro Asp Gly Phe Trp Leu Gly Glu Gln
    290                 295                 300

Leu Val Cys Trp Gln Ala Gly Thr Thr Pro Trp Asn Ile Phe Pro Val
305                 310                 315                 320

Ile Ser Leu Tyr Leu Met Gly Glu Val Thr Asn Gln Ser Phe Arg Ile
                325                 330                 335

Thr Ile Leu Pro Gln Gln Tyr Leu Arg Pro Val Glu Asp Val Ala Thr
            340                 345                 350

Ser Gln Asp Asp Cys Tyr Lys Phe Ala Ile Ser Gln Ser Ser Thr Gly
        355                 360                 365

Thr Val Met Gly Ala Val Ile Met Glu Gly Phe Tyr Val Val Phe Asp
    370                 375                 380

Arg Ala Arg Lys Arg Ile Gly Phe Ala Val Ser Ala Cys His Val His
385                 390                 395                 400

Asp Glu Phe Arg Thr Ala Ala Val Glu Gly Pro Phe Val Thr Leu Asp
                405                 410                 415

Met Glu Asp Cys Gly Tyr Asn Ile Pro Gln Thr Asp Glu Ser
            420                 425                 430

<210> SEQ ID NO 26
<211> LENGTH: 1236
<212> TYPE: DNA
<213> ORGANISM: Homo sapiens
<220> FEATURE:
<221> NAME/KEY: CDS
<222> LOCATION: (1)..(1236)

<400> SEQUENCE: 26 atg gct agc atg act ggt gga cag caa atg ggt cgc gga tcc atg gct    48
Met Ala Ser Met Thr Gly Gly Gln Gln Met Gly Arg Gly Ser Met Ala
1               5                   10                  15 ggt gtt ctg cca gct cac ggt acc caa cat ggt att cgt ctg cca ctg    96
Gly Val Leu Pro Ala His Gly Thr Gln His Gly Ile Arg Leu Pro Leu
            20                  25                  30 cgt agc ggt ctg ggt ggt gct cca ctg ggt ctg cgt ctg ccc cgg gag   144
Arg Ser Gly Leu Gly Gly Ala Pro Leu Gly Leu Arg Leu Pro Arg Glu
        35                  40                  45 acc gac gaa gag ccc gag gag ccc ggc cgg agg ggc agc ttt gtg gag   192
Thr Asp Glu Glu Pro Glu Glu Pro Gly Arg Arg Gly Ser Phe Val Glu
```

|     |     |     |     |     |     |     |     |     |     |     |     |     |
| --- | --- | --- | --- | --- | --- | --- | --- | --- | --- | --- | --- | --- |
| Thr | Asp | Glu | Glu | Pro | Glu | Pro | Gly | Arg | Arg | Gly | Ser | Phe | Val | Glu |
|  | 50 |  |  |  | 55 |  |  |  | 60 |  |  |  |  |

```
atg gtg gac aac ctg agg ggc aag tcg ggg cag ggc tac tac gtg gag       240
Met Val Asp Asn Leu Arg Gly Lys Ser Gly Gln Gly Tyr Tyr Val Glu
 65          70                  75                  80 atg acc gtg ggc agc ccc ccg cag acg ctc aac atc ctg gtg gat aca       288
Met Thr Val Gly Ser Pro Pro Gln Thr Leu Asn Ile Leu Val Asp Thr
                 85                  90                  95 ggc agc agt aac ttt gca gtg ggt gct gcc ccc cac ccc ttc ctg cat       336
Gly Ser Ser Asn Phe Ala Val Gly Ala Ala Pro His Pro Phe Leu His
            100                 105                 110 cgc tac tac cag agg cag ctg tcc agc aca tac cgg gac ctc cgg aag       384
Arg Tyr Tyr Gln Arg Gln Leu Ser Ser Thr Tyr Arg Asp Leu Arg Lys
        115                 120                 125 ggc gtg tat gtg ccc tac acc cag ggc aag tgg gaa ggg gag ctg ggc       432
Gly Val Tyr Val Pro Tyr Thr Gln Gly Lys Trp Glu Gly Glu Leu Gly
    130                 135                 140 acc gac ctg cct gac gac tcc ctg gag cct ttc ttt gac tct ctg gta       480
Thr Asp Leu Pro Asp Asp Ser Leu Glu Pro Phe Phe Asp Ser Leu Val
145                 150                 155                 160 aag cag acc cac gtt ccc aac ctc ttc tcc ctg cag ctt tgt ggt gct       528
Lys Gln Thr His Val Pro Asn Leu Phe Ser Leu Gln Leu Cys Gly Ala
                165                 170                 175 ggc ttc ccc ctc aac cag tct gaa gtg ctg gcc tct gtc gga ggg agc       576
Gly Phe Pro Leu Asn Gln Ser Glu Val Leu Ala Ser Val Gly Gly Ser
            180                 185                 190 atg atc att gga ggt atc gac cac tcg ctg tac aca ggc agt ctc tgg       624
Met Ile Ile Gly Gly Ile Asp His Ser Leu Tyr Thr Gly Ser Leu Trp
        195                 200                 205 tat aca ccc atc cgg cgg gag tgg tat tat gag gtc atc att gtg cgg       672
Tyr Thr Pro Ile Arg Arg Glu Trp Tyr Tyr Glu Val Ile Ile Val Arg
    210                 215                 220 gtg gag atc aat gga cag gat ctg aaa atg gac tgc aag gag tac aac       720
Val Glu Ile Asn Gly Gln Asp Leu Lys Met Asp Cys Lys Glu Tyr Asn
225                 230                 235                 240 tat gac aag agc att gtg gac agt ggc acc acc aac ctt cgt ttg ccc       768
Tyr Asp Lys Ser Ile Val Asp Ser Gly Thr Thr Asn Leu Arg Leu Pro
                245                 250                 255 aag aaa gtg ttt gaa gct gca gtc aaa tcc atc aag gca gcc tcc tcc       816
Lys Lys Val Phe Glu Ala Ala Val Lys Ser Ile Lys Ala Ala Ser Ser
            260                 265                 270 acg gag aag ttc cct gat ggt ttc tgg cta gga gag cag ctg gtg tgc       864
Thr Glu Lys Phe Pro Asp Gly Phe Trp Leu Gly Glu Gln Leu Val Cys
        275                 280                 285 tgg caa gca ggc acc acc cct tgg aac att ttc cca gtc atc tca ctc       912
Trp Gln Ala Gly Thr Thr Pro Trp Asn Ile Phe Pro Val Ile Ser Leu
    290                 295                 300 tac cta atg ggt gag gtt acc aac cag tcc ttc cgc atc acc atc ctt       960
Tyr Leu Met Gly Glu Val Thr Asn Gln Ser Phe Arg Ile Thr Ile Leu
305                 310                 315                 320 ccg cag caa tac ctg cgg cca gtg gaa gat gtg gcc acg tcc caa gac      1008
Pro Gln Gln Tyr Leu Arg Pro Val Glu Asp Val Ala Thr Ser Gln Asp
                325                 330                 335 gac tgt tac aag ttt gcc atc tca cag tca tcc acg ggc act gtt atg      1056
Asp Cys Tyr Lys Phe Ala Ile Ser Gln Ser Ser Thr Gly Thr Val Met
            340                 345                 350 gga gct gtt atc atg gag ggc ttc tac gtt gtc ttt gat cgg gcc cga      1104
Gly Ala Val Ile Met Glu Gly Phe Tyr Val Val Phe Asp Arg Ala Arg
        355                 360                 365
```

```
aaa cga att ggc ttt gct gtc agc gct tgc cat gtg cac gat gag ttc    1152
Lys Arg Ile Gly Phe Ala Val Ser Ala Cys His Val His Asp Glu Phe
370             375                 380 agg acg gca gcg gtg gaa ggc cct ttt gtc acc ttg gac atg gaa gac    1200
Arg Thr Ala Ala Val Glu Gly Pro Phe Val Thr Leu Asp Met Glu Asp
385             390                 395                 400 tgt ggc tac aac att cca cag aca gat gag tca tag                    1236
Cys Gly Tyr Asn Ile Pro Gln Thr Asp Glu Ser
                405                 410
```

<210> SEQ ID NO 27
<211> LENGTH: 411
<212> TYPE: PRT
<213> ORGANISM: Homo sapiens

<400> SEQUENCE: 27

```
Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
                20                  25                  30

Arg Ser Gly Leu Gly Gly Ala Pro Leu Gly Leu Arg Leu Pro Arg Glu
            35                  40                  45

Thr Asp Glu Glu Pro Glu Pro Gly Arg Arg Gly Ser Phe Val Glu
    50                  55                  60

Met Val Asp Asn Leu Arg Gly Lys Ser Gly Gln Gly Tyr Tyr Val Glu
65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His
            100                 105                 110

Arg Tyr Tyr Gln Arg Gln Leu Ser Ser Thr Tyr Arg Asp Leu Arg Lys
        115                 120                 125

Gly Val Tyr Val Pro Tyr Thr Gln Gly Lys Trp Glu Gly Glu Leu Gly
    130                 135                 140

Thr Asp Leu Pro Asp Asp Ser Leu Glu Pro Phe Phe Asp Ser Leu Val
145                 150                 155                 160

Lys Gln Thr His Val Pro Asn Leu Phe Ser Leu Gln Leu Cys Gly Ala
                165                 170                 175

Gly Phe Pro Leu Asn Gln Ser Glu Val Leu Ala Ser Val Gly Gly Ser
            180                 185                 190

Met Ile Ile Gly Gly Ile Asp His Ser Leu Tyr Thr Gly Ser Leu Trp
        195                 200                 205

Tyr Thr Pro Ile Arg Arg Glu Trp Tyr Tyr Glu Val Ile Ile Val Arg
    210                 215                 220

Val Glu Ile Asn Gly Gln Asp Leu Lys Met Asp Cys Lys Glu Tyr Asn
225                 230                 235                 240

Tyr Asp Lys Ser Ile Val Asp Ser Gly Thr Thr Asn Leu Arg Leu Pro
                245                 250                 255

Lys Lys Val Phe Glu Ala Ala Val Lys Ser Ile Lys Ala Ala Ser Ser
            260                 265                 270

Thr Glu Lys Phe Pro Asp Gly Phe Trp Leu Gly Glu Gln Leu Val Cys
        275                 280                 285

Trp Gln Ala Gly Thr Thr Pro Trp Asn Ile Phe Pro Val Ile Ser Leu
    290                 295                 300

Tyr Leu Met Gly Glu Val Thr Asn Gln Ser Phe Arg Ile Thr Ile Leu
305                 310                 315                 320
```

```
Pro Gln Gln Tyr Leu Arg Pro Val Glu Asp Val Ala Thr Ser Gln Asp
                325                 330                 335

Asp Cys Tyr Lys Phe Ala Ile Ser Gln Ser Ser Thr Gly Thr Val Met
            340                 345                 350

Gly Ala Val Ile Met Glu Gly Phe Tyr Val Val Phe Asp Arg Ala Arg
        355                 360                 365

Lys Arg Ile Gly Phe Ala Val Ser Ala Cys His Val His Asp Glu Phe
370                 375                 380

Arg Thr Ala Ala Val Glu Gly Pro Phe Val Thr Leu Asp Met Glu Asp
385                 390                 395                 400

Cys Gly Tyr Asn Ile Pro Gln Thr Asp Glu Ser
                405                 410

<210> SEQ ID NO 28
<211> LENGTH: 13
<212> TYPE: PRT
<213> ORGANISM: Artificial
<220> FEATURE:
<223> OTHER INFORMATION: Artificial Sequence
<220> FEATURE:
<221> NAME/KEY: MISC_FEATURE
<222> LOCATION: (5)..(5)
<223> OTHER INFORMATION: Xaa is 4-amino-3-hydroxy-6-methylheptanoic acid

<400> SEQUENCE: 28

Ser Glu Val Asn Xaa Val Ala Glu Phe Arg Gly Gly Cys
1               5                   10

<210> SEQ ID NO 29
<211> LENGTH: 8
<212> TYPE: PRT
<213> ORGANISM: Artificial
<220> FEATURE:
<223> OTHER INFORMATION: Artificial Sequence
<220> FEATURE:
<221> NAME/KEY: MISC_FEATURE
<223> OTHER INFORMATION: Cleavage Product from Peptide Substrate

<400> SEQUENCE: 29

Glu Val Glu Phe Arg Trp Lys Lys
1               5

<210> SEQ ID NO 30
<211> LENGTH: 4
<212> TYPE: PRT
<213> ORGANISM: Artificial
<220> FEATURE:
<223> OTHER INFORMATION: Artificial Sequence
<220> FEATURE:
<221> NAME/KEY: MISC_FEATURE
<223> OTHER INFORMATION: Caspase 8 Cleavage Site

<400> SEQUENCE: 30

Ile Glu Thr Asp
1

<210> SEQ ID NO 31
<211> LENGTH: 393
<212> TYPE: PRT
<213> ORGANISM: Homo sapiens
<220> FEATURE:
<221> NAME/KEY: MISC_FEATURE
<223> OTHER INFORMATION: BACE V40- S432 fragment

<400> SEQUENCE: 31
```

-continued

```
Val Glu Met Val Asp Asn Leu Arg Gly Lys Ser Gly Gln Gly Tyr Tyr
1               5                   10                  15

Val Glu Met Thr Val Gly Ser Pro Pro Gln Thr Leu Asn Ile Leu Val
            20                  25                  30

Asp Thr Gly Ser Ser Asn Phe Ala Val Gly Ala Ala Pro His Pro Phe
        35                  40                  45

Leu His Arg Tyr Tyr Gln Arg Gln Leu Ser Ser Thr Tyr Arg Asp Leu
    50                  55                  60

Arg Lys Gly Val Tyr Val Pro Tyr Thr Gln Gly Lys Trp Glu Gly Glu
65                  70                  75                  80

Leu Gly Thr Asp Leu Val Ser Ile Pro His Gly Pro Asn Val Thr Val
            85                  90                  95

Arg Ala Asn Ile Ala Ala Ile Thr Glu Ser Asp Lys Phe Phe Ile Asn
            100                 105                 110

Gly Ser Asn Trp Glu Gly Ile Leu Gly Leu Ala Tyr Ala Glu Ile Ala
        115                 120                 125

Arg Pro Asp Asp Ser Leu Glu Pro Phe Phe Asp Ser Leu Val Lys Gln
    130                 135                 140

Thr His Val Pro Asn Leu Phe Ser Leu Gln Leu Cys Gly Ala Gly Phe
145                 150                 155                 160

Pro Leu Asn Gln Ser Glu Val Leu Ala Ser Val Gly Gly Ser Met Ile
                165                 170                 175

Ile Gly Gly Ile Asp His Ser Leu Tyr Thr Gly Ser Leu Trp Tyr Thr
            180                 185                 190

Pro Ile Arg Arg Glu Trp Tyr Tyr Glu Val Ile Ile Val Arg Val Glu
        195                 200                 205

Ile Asn Gly Gln Asp Leu Lys Met Asp Cys Lys Glu Tyr Asn Tyr Asp
210                 215                 220

Lys Ser Ile Val Asp Ser Gly Thr Thr Asn Leu Arg Leu Pro Lys Lys
225                 230                 235                 240

Val Phe Glu Ala Ala Val Lys Ser Ile Lys Ala Ala Ser Ser Thr Glu
                245                 250                 255

Lys Phe Pro Asp Gly Phe Trp Leu Gly Glu Gln Leu Val Cys Trp Gln
            260                 265                 270

Ala Gly Thr Thr Pro Trp Asn Ile Phe Pro Val Ile Ser Leu Tyr Leu
        275                 280                 285

Met Gly Glu Val Thr Asn Gln Ser Phe Arg Ile Thr Ile Leu Pro Gln
290                 295                 300

Gln Tyr Leu Arg Pro Val Glu Asp Val Ala Thr Ser Gln Asp Asp Cys
305                 310                 315                 320

Tyr Lys Phe Ala Ile Ser Gln Ser Ser Thr Gly Thr Val Met Gly Ala
                325                 330                 335

Val Ile Met Glu Gly Phe Tyr Val Val Phe Asp Arg Ala Arg Lys Arg
            340                 345                 350

Ile Gly Phe Ala Val Ser Ala Cys His Val His Asp Glu Phe Arg Thr
        355                 360                 365

Ala Ala Val Glu Gly Pro Phe Val Thr Leu Asp Met Glu Asp Cys Gly
    370                 375                 380

Tyr Asn Ile Pro Gln Thr Asp Glu Ser
385                 390
```

<210> SEQ ID NO 32
<211> LENGTH: 399
<212> TYPE: PRT

<213> ORGANISM: Homo sapiens
<220> FEATURE:
<221> NAME/KEY: MISC_FEATURE
<223> OTHER INFORMATION: HIV Protease treated BACE Asp2-2L-TM-His6

<400> SEQUENCE: 32

```
Val Glu Met Val Asp Asn Leu Arg Gly Lys Ser Gln Gly Tyr Tyr
 1               5                  10                  15

Val Glu Met Thr Val Gly Ser Pro Pro Gln Thr Leu Asn Ile Leu Val
                20                  25                  30

Asp Thr Gly Ser Ser Asn Phe Ala Val Gly Ala Ala Pro His Pro Phe
                35                  40                  45

Leu His Arg Tyr Tyr Gln Arg Gln Leu Ser Ser Thr Tyr Arg Asp Leu
        50                  55                  60

Arg Lys Gly Val Tyr Val Pro Tyr Thr Gln Gly Lys Trp Glu Gly Glu
 65                  70                  75                  80

Leu Gly Thr Asp Leu Val Ser Ile Pro His Gly Pro Asn Val Thr Val
                85                  90                  95

Arg Ala Asn Ile Ala Ala Ile Thr Glu Ser Asp Lys Phe Phe Ile Asn
                100                 105                 110

Gly Ser Asn Trp Glu Gly Ile Leu Gly Leu Ala Tyr Ala Glu Ile Ala
            115                 120                 125

Arg Pro Asp Asp Ser Leu Glu Pro Phe Phe Asp Ser Leu Val Lys Gln
    130                 135                 140

Thr His Val Pro Asn Leu Phe Ser Leu Gln Leu Cys Gly Ala Gly Phe
145                 150                 155                 160

Pro Leu Asn Gln Ser Glu Val Leu Ala Ser Val Gly Gly Ser Met Ile
                165                 170                 175

Ile Gly Gly Ile Asp His Ser Leu Tyr Thr Gly Ser Leu Trp Tyr Thr
                180                 185                 190

Pro Ile Arg Arg Glu Trp Tyr Tyr Glu Val Ile Ile Val Arg Val Glu
            195                 200                 205

Ile Asn Gly Gln Asp Leu Lys Met Asp Cys Lys Glu Tyr Asn Tyr Asp
    210                 215                 220

Lys Ser Ile Val Asp Ser Gly Thr Thr Asn Leu Arg Leu Pro Lys Lys
225                 230                 235                 240

Val Phe Glu Ala Ala Val Lys Ser Ile Lys Ala Ala Ser Ser Thr Glu
                245                 250                 255

Lys Phe Pro Asp Gly Phe Trp Leu Gly Glu Gln Leu Val Cys Trp Gln
            260                 265                 270

Ala Gly Thr Thr Pro Trp Asn Ile Phe Pro Val Ile Ser Leu Tyr Leu
    275                 280                 285

Met Gly Glu Val Thr Asn Gln Ser Phe Arg Ile Thr Ile Leu Pro Gln
290                 295                 300

Gln Tyr Leu Arg Pro Val Glu Asp Val Ala Thr Ser Gln Asp Asp Cys
305                 310                 315                 320

Tyr Lys Phe Ala Ile Ser Gln Ser Ser Thr Gly Thr Val Met Gly Ala
                325                 330                 335

Val Ile Met Glu Gly Phe Tyr Val Val Phe Asp Arg Ala Arg Lys Arg
            340                 345                 350

Ile Gly Phe Ala Val Ser Ala Cys His Val His Asp Glu Phe Arg Thr
    355                 360                 365

Ala Ala Val Glu Gly Pro Phe Val Thr Leu Asp Met Glu Asp Cys Gly
370                 375                 380
```

```
Tyr Asn Ile Pro Gln Thr Asp Glu Ser His His His His His
385                 390                 395

<210> SEQ ID NO 33
<211> LENGTH: 269
<212> TYPE: PRT
<213> ORGANISM: Homo sapiens
<220> FEATURE:
<221> NAME/KEY: MISC_FEATURE
<223> OTHER INFORMATION: BACE Ala164 - Ser 432 fragment

<400> SEQUENCE: 33

Ala Glu Ile Ala Arg Pro Asp Asp Ser Leu Glu Pro Phe Phe Asp Ser
1               5                   10                  15

Leu Val Lys Gln Thr His Val Pro Asn Leu Phe Ser Leu Gln Leu Cys
            20                  25                  30

Gly Ala Gly Phe Pro Leu Asn Gln Ser Glu Val Leu Ala Ser Val Gly
                35                  40                  45

Gly Ser Met Ile Ile Gly Ile Asp His Ser Leu Tyr Thr Gly Ser
        50                  55                  60

Leu Trp Tyr Thr Pro Ile Arg Arg Glu Trp Tyr Tyr Glu Val Ile Ile
65                  70                  75                  80

Val Arg Val Glu Ile Asn Gly Gln Asp Leu Lys Met Asp Cys Lys Glu
                85                  90                  95

Tyr Asn Tyr Asp Lys Ser Ile Val Asp Ser Gly Thr Thr Asn Leu Arg
                100                 105                 110

Leu Pro Lys Lys Val Phe Glu Ala Ala Val Lys Ser Ile Lys Ala Ala
            115                 120                 125

Ser Ser Thr Glu Lys Phe Pro Asp Gly Phe Trp Leu Gly Glu Gln Leu
        130                 135                 140

Val Cys Trp Gln Ala Gly Thr Thr Pro Trp Asn Ile Phe Pro Val Ile
145                 150                 155                 160

Ser Leu Tyr Leu Met Gly Glu Val Thr Asn Gln Ser Phe Arg Ile Thr
                165                 170                 175

Ile Leu Pro Gln Gln Tyr Leu Arg Pro Val Glu Asp Val Ala Thr Ser
            180                 185                 190

Gln Asp Asp Cys Tyr Lys Phe Ala Ile Ser Gln Ser Ser Thr Gly Thr
        195                 200                 205

Val Met Gly Ala Val Ile Met Glu Gly Phe Tyr Val Val Phe Asp Arg
210                 215                 220

Ala Arg Lys Arg Ile Gly Phe Ala Val Ser Ala Cys His Val His Asp
225                 230                 235                 240

Glu Phe Arg Thr Ala Ala Val Glu Gly Pro Phe Val Thr Leu Asp Met
                245                 250                 255

Glu Asp Cys Gly Tyr Asn Ile Pro Gln Thr Asp Glu Ser
            260                 265
```

METHOD FOR REFOLDING ENZYMES

CROSS-REFERENCE TO RELATED APPLICATIONS

This application is a continuation of U.S. patent application Ser. No. 10/230,677, filed Aug. 29, 2002, which claims the benefit of U.S. Provisional Patent Application Ser. No. 60/316,934, filed Aug. 31, 2001.

FIELD OF THE INVENTION

The invention relates generally to recombinant expression, refolding, and purification of an enzyme. More particularly, the invention relates to novel methods for preparing purified, active, human BACE expressed in E. coli.

BACKGROUND OF THE INVENTION

Neuritic plaques containing primarily amyloid beta protein (Abeta) are one of the hallmarks of Alzheimer's Disease. Beta-site APP cleaving enzyme (BACE), known also as beta-secretase, Asp2, and Memapsin, has been identified as the enzyme responsible for processing amyloid precursor protein (APP) to produce the N-terminal portion of the Abeta peptide. This enzyme has been suggested as rate limiting in the production of the Abeta peptide. See, for example, Sinha et al., 1999, Nature 402:537-554, and published PCT applications WO 00/17369, WO 01/23533, and WO 98/22597. See also: Hussain, I. et al., 1999, Mol. Cell. Neurosci. 14:419-427; Vassar, R. et al., 1999, Science 286:735-741; Yan, R. et al., 2000, Nature 402:533-537; and Lin, X. et al., 2000, Proc. Natl. Acad. Sci. USA 97:1456-1460 (2000).

BACE is a therapeutic target for the development of inhibitory compounds for the treatment of Alzheimer's Disease. Rational drug design methods require supply of properly expressed, refolded, and active BACE in order to model and design appropriate new drugs. BACE in sufficient amounts has proven difficult to obtain.

BACE is a relatively large and structurally complex enzyme. The primary structure of BACE as it is synthesized in the endoplasmic reticulum is shown in FIG. 1 [SEQ ID NO:1]. The enzyme contains 501 amino acids, including a N-terminal signal (leader) sequence of about 21 amino acids (pre-sequence domain) followed by a pro-sequence domain consisting approximately of residues 22 to 45 (pro-sequence domain) that is proteolytically removed once the enzyme reaches its destination in the Golgi apparatus, to generate a mature enzyme.

Prosequence domains are commonly found in protease precursor polypeptides, where they generally function to prevent catalytic activity and assist in protein folding. The prosequence domain is typically cleaved from the protease precursor to generate a mature active protease. Previous work in a baculovirus expression system, expressing a BACE precursor having BACE pre-sequence and pro-sequence domains but truncated at the junction between the putative protease and transmembrane region, indicated that the pro-sequence domain facilitates proper folding of the BACE protease domain. See Shi, X-P. et al., Mar. 30, 2001, J. of Biol. Chem. 276(13):10366-10373.

BACE contains a transmembrane domain of about 27 amino acids that anchors the protein to the membrane. A short cytosolic C-terminal tail of 21 amino acids follows the transmembrane domain. Attachment to the membrane allows BACE to interact with and cleave APP, the first and prerequisite step in the generation of A-beta.

BACE isolated from human brain is heavily glycosylated. As expressed by a stably transfected 293T cell line, BACE is glycosylated at four asparagines: 132, 151, 202, and 333. Analysis of HEK 293 cells stably overexpressing BACE showed that the enzyme is phosphorylated at Ser477, and that phosphorylation regulates enzyme intracellular trafficking (Walter et. al., 2001, J. Biol. Chem. 276:14634-41). Three disulfide bonds suggested as critical for activity, are formed between the following pairs of cysteine residues: Cys195-Cys399, Cys257-Cys422, and Cys309-Cys359 (Haniu et. al., 2000, J. Biol. Chem. 275:21099-21106).

These structural features of the BACE polypeptide all appear to have specific functions relating to enzymatic activity. Enzymes expressed in insect and CHO cells are properly refolded and show activity. These proteins are glycosylated. For example, insect cells express glycosylated BACE, from the mannose-rich glycans available in the insect cells. Biantennary and triantennary oligosaccharides of the complex type provide glycosylation in the CHO-expressed BACE (Charlwood et. al., 2001 J. Biol. Chem. 276:16739-48). These glycosylated proteins have proven difficult to process, however, due to the heterogeneity conferred by differential glycosylation. BACE production in these cells generally requires expensive culture media and does not yield high amounts of protein.

These negative aspects of mammalian and insect cell expression do not apply to BACE proteins expressed in E. coli. Bacteria are easy to grow, produce high yields of protein, and the cost of culture media is low. However, E. coli do not provide for post-translational modifications of the protein.

Previous attempts to produce and isolate large quantities of active BACE from E. coli were initially unsuccessful. Although the cells grew well and expressed reasonable quantities of protein, refolding and isolating the enzyme using known published methods, including those described in Lin et. al. 2000, PNAS USA 97:1456-60 and Tang, WO 01/00663, failed to produce quantities of active BACE suitable for drug discovery methods.

Accordingly, a simple, efficient, and reliable method for expression of recombinant BACE in E. coli and for refolding and purification of sufficient quantities of BACE necessary for use in drug discovery methods is greatly needed.

SUMMARY OF THE INVENTION

The invention provides for a method of refolding recombinant BACE polypeptide. In one aspect of the invention, the method includes:

a) solubilizing a recombinant BACE polypeptide in a denaturant at a pH of about 10-11 and in the presence of a reducing agent;

b) diluting the solubilized BACE polypeptide in an aqueous solution having a temperature of about 1° C. to 15° C., to obtain a diluted sample; and c) incubating the diluted sample at a temperature of about 4° C. to 15° C. until the recombinant BACE polypeptide folds into an active enzyme.

In various aspects of the invention, the solubilized BACE is diluted to a final concentration of about 1 microgram/ml to about 300 micrograms/ml. Also, prior to dilution, the recombinant BACE has an absorbance at 280 nm of about 0.1 to about 4.0, and the solubilized BACE is diluted from about 10 fold to about 150 fold. Further, the active enzyme has at least about 40% of the activity of recombinant BACE expressed in CHO cells.

In another aspect of the invention, the recombinant BACE is pQE70-BACE [SEQ ID NO:3], pQE80L-BACE [SEQ ID NO:7], or pET11a BACE [SEQ ID NO:5] and the incubation is from about 3 days to about 6 weeks.

In yet another aspect of the invention the recombinant BACE is lacking all or a portion of the BACE prosequence.

An additional aspect of the invention further provides for a method of producing active recombinant BACE polypeptide comprising:
  a) expressing a polynucleotide encoding BACE polypeptide in *E. coli* to produce inclusion bodies of recombinant BACE polypeptide;
  b) solubilizing the inclusion bodies to release the BACE polypeptide;
  c) reducing the released BACE polypeptide with a reducing agent;
  d) diluting the reduced BACE with an aqueous solution having a temperature of about 1° C. to 15° C.; and
  e) incubating the diluted BACE at a temperature of about 4° C. to 15° C. and at a pH of about 10-11, to obtain active BACE polypeptide.

In this aspect of the invention, the BACE may be diluted to a final concentration of about 1 microgram/ml to about 300 micrograms/ml. The solubilized BACE, prior to dilution, may have an absorbance at 280 nm of about 0.1 to about 4.0, and the solubilized BACE may be diluted from about 10 fold to about 150 fold. The active enzyme may have at least about 40% of the activity of recombinant BACE expressed in CHO cells. The diluted sample may be incubated from about 3 days to about 6 weeks. The polynucleotide sequence may encode pQE70-BACE [SEQ ID NO:3], pQE80L-BACE [SEQ ID NO:7], or pET11a-BACE [SEQ ID NO:5]. The polynucleotide may encode a BACE lacking all or a portion of its prosequence.

Another aspect of the invention relates to a method for refolding BACE polypeptide comprising:
  a) diluting solubulized, reduced BACE polypeptide at least 20 fold with a low ionic strength aqueous solution having a temperature of about 1 to 15° C.;
  b) incubating the diluted BACE polypeptide at a starting pH of about 10 to 11, and at a temperature of about 1 to 15° C. from about 2 days to about 6 weeks, and
  c) recovering active, refolded BACE polypeptide.

In this aspect of the invention, the method may include adding a reducing agent to the expressed recombinant BACE polypeptide prior to the diluting step. The reducing agent may be beta-mercaptoethanol.

In another aspect, the invention relates to a method for producing active, recombinant BACE polypeptide. The method includes:
  a) expressing a polynucleotide encoding BACE polypeptide in *E. coli;*
  b) isolating and purifying the expressed BACE polypeptide from the *E. coli;*
  c) refolding the purified BACE polypeptide by a method that comprises diluting the purified BACE polypeptide 20-50 fold with water having a temperature of about 1 to about 15° C. under conditions of reduced protein; and
  d) recovering active recombinant BACE polypeptide.

In another aspect, the invention relates to cleaving the refolded BACE polypeptide in the presence of HIV-protease.

In another aspect, the invention relates to expression construct for the expression of recombinant BACE comprising the structure of any of the constructs B1-B6.

In another aspect, the invention relates to a fusion protein for the expression of recombinant BACE including a polynucleotide encoding a BACE polypeptide and a Caspase8 cleavage site.

DESCRIPTION OF THE FIGURES

FIG. 1 is the polypeptide sequence of human BACE [SEQ ID NO: 1]

FIGS. 2A-2C show the DNA [SEQ ID NO: 4] and predicted amino acid [SEQ ID NO: 5] sequences of pET11a-BACE.

FIGS. 3A-3C show the DNA [SEQ ID NO: 6] and predicted amino acid [SEQ ID NO: 7] sequences of pQE80L-BACE.

FIGS. 4A and 4B show the DNA [SEQ ID NO: 2] and predicted amino acid [SEQ ID NO: 3] sequences of pQE70-BACE.

FIG. 6 shows photographs of gels showing the progression of BACE polypeptide purification from expressed inclusion bodies through chromatographic purification columns. Lane A2 shows isolated inclusion body protein; lane A4 shows the refolded protein purified by Q-sepharose; and lane A7 shows the protein product after I-1 affinity chromatography. Lane B2 shows isolated inclusion body protein; lane B3 shows refolded protein purified through Q-sepharose; lane B4 through Sephacryl-200; and lane B5 shows the protein product after I-1 affinity chromatography.

FIG. 9 shows the amino acid sequence [SEQ ID NO: 23]of recombinant BACE expressed in CHO cells.

DETAILED DESCRIPTION OF THE INVENTION

Figure 5:
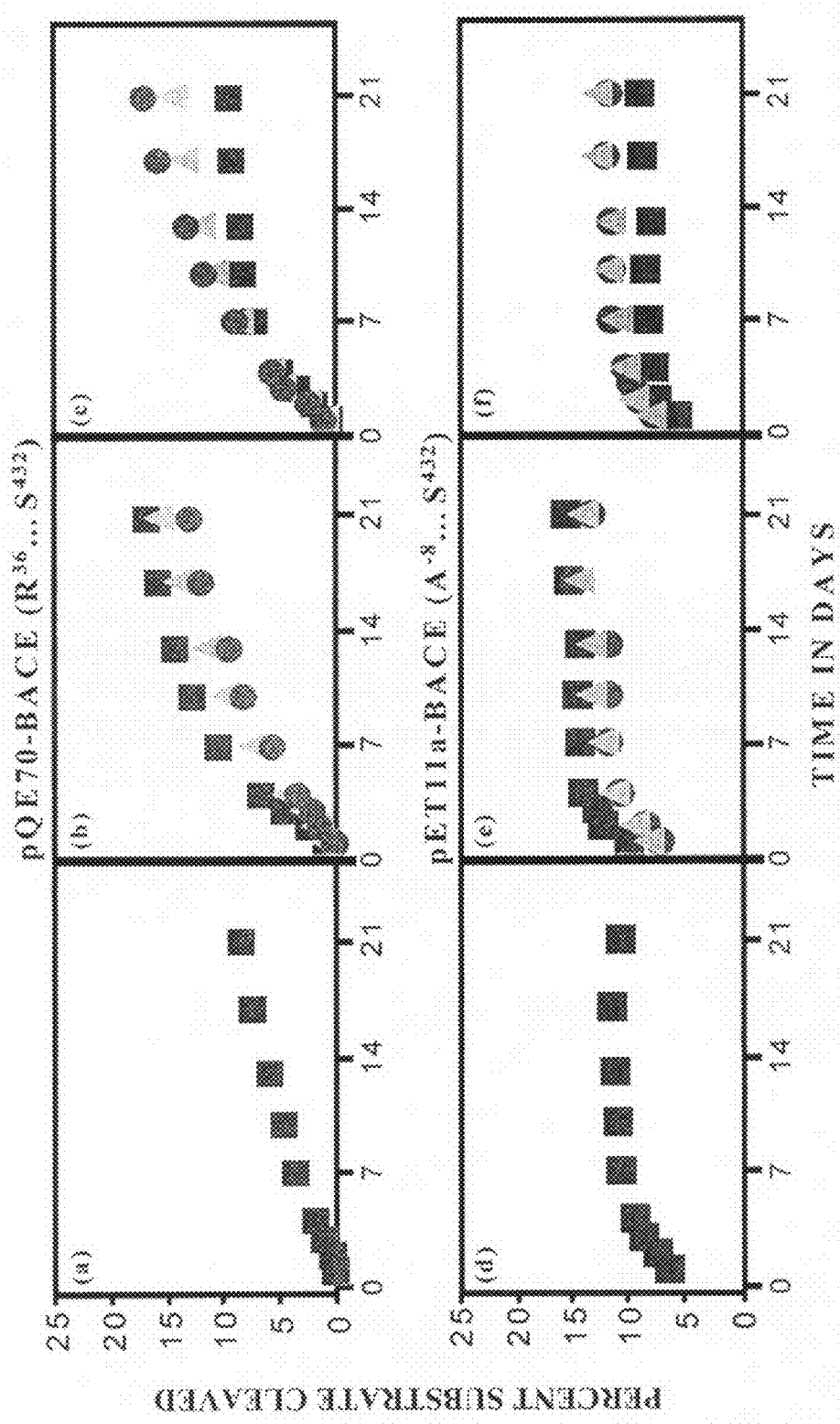
FIG. 5 is a series of graphs showing the activity of recombinant BACE prepared from a series of dilutions and incubated for various times. Initial protein concentrations in 7.5 M urea were measured at 280 nm and adjusted to an absorbance of 0.5 AU (a & d), 1.5 AU (b & e), and 3.0 AU (c & f) prior to dilution with cold water. Dilution factors were 20 (squares), 35 (triangles), and 50 (circles).

"BACE" (beta-site APP-cleaving enzyme), refers to an enzyme that mediates cleavage at the beta-site of APP. This enzyme is also known as beta-secretase, Asp2, and Memapsin 2. BACE has been described, for example, in published PCT patent applications: WO 00/17369, WO 00/47618 and WO 01/23533, each of which is incorporated herein by reference in their entirety. BACE comprises an aspartyl protease and contains the classical consensus aspartyl protease active site motif (DTG/DSG). As used herein, BACE refers to the full length BACE or an active fragment.

Features of the BACE polypeptide shown in FIG. 1 [SEQ ID NO. 1] include a 21 amino acid leader (signal or pre-) sequence shown in italics, and a 24 amino acid pro-sequence, shown in bold type. $T^1$ marks the start of the pro-sequence. A furin cleavage site at amino acid $E^{25}$ is indicated by ↓ suggesting $E^{25}$ as the start of the catalytic or protease domain. F↓V indicates an HIV-1 protease cleavage site discovered at $V^{40}$, as disclosed in the Examples below. Four glycosylated asparagines at amino acid positions 132, 151, 202, and 333 are shown in bold-italics (N). A 27 amino acid transmembrane domain is underlined, and is followed by the cytosolic C-terminal tail. Disulphide bridges are formed by cysteines ($Cys^{195}$-$Cys^{399}$, $Cys^{257}$-$Cys^{422}$; and $Cys^{309}$-$Cys^{359}$)

The 24 amino acid pro-segment shown in FIG. 1 represents the commonly understood prosegment found in BACE purified from human brain tissue. However, as used herein, the prosegment of BACE may include a greater number of amino acids. As shown below, it has been discovered that BACE constructs lacking amino acids up to $Arg^{36}$ or $Val^{40}$ provide for an active enzyme. In addition, a sequence alignment of BACE with other common aspartyl proteases, such as pepsinogen and progastricsin, suggests that the prosegment may be as long as about 45 amino acids. Accordingly, for the purposes herein, the prosegment may include any number of amino acids as long as the amino acid sequence remaining after the deletion can be an active enzyme.

Recombinant BACE can be produced, for example, in E. coli or other suitable host cells, by expressing a construct that contains at least a portion of a cDNA encoding BACE, for example, encoding at least a portion of the amino acid sequence shown in FIG. 1 [SEQ ID NO:1]. The construct can also contain additional nucleotide sequences that may, for example, assist in purification and/or expression of the recombinant polypeptide, as desired.

When expressed in E. coli, recombinant BACE accumulates intracellularly in an insoluble form, resulting in phase-bright inclusions in the cytoplasm (inclusion bodies). The protein in the inclusion bodies can be a mixture of monomeric and multimeric forms of the protein, both reduced and oxidized.

Processes designed to recover biologically active, soluble protein from the insoluble cellular material generally include the steps of: (1) cell lysis, (2) isolation of inclusion bodies, (3) solubilization of protein from inclusion bodies, (4) refolding of solubilized protein, and (5) purification of the active protein. Each of these steps will be described in relation to the invention below.

Cloning and Expression of BACE

Expression constructs and methods have been developed for the efficient production, refolding, and purification of recombinant protein, for example, recombinant human BACE. Production, refolding, and purification of protein can be of protein produced in bacterial hosts, such as E. coli.

Useful constructs for the production of BACE are designed to express a selected portion of the BACE polypeptide, for example, express a portion of the amino acid sequence shown in FIG. 1 [SEQ ID NO:1]. The polynucleotide encoding the BACE polypeptide can be operably linked to suitable transcriptional or translational regulatory sequences in an expression construct. Regulatory sequences include transcriptional promoters, operators, enhancers, mRNA ribosomal binding sites, and other sequences that control transcription or translation. Nucleotide sequences are "operably linked" when the regulatory sequence functionally relates to the polynucleotide encoding BACE. Thus, a promoter nucleotide sequence is operably linked to a polynucleotide encoding BACE if the promoter nucleotide sequence directs the transcription of the BACE sequence.

The polynucleotide is cloned into appropriate expression vectors for expression in the appropriate host. Generally, an expression vector will include a selectable marker and an origin of replication, such as for propagation in E. coli. Expression vectors generally comprise one or more phenotypic selectable marker genes. Such genes generally encode, for example, a protein that confers antibiotic resistance or that supplies an auxotrophic requirement.

A polynucleotide can encode a BACE polypeptide having an N-terminal methionine to facilitate expression of the recombinant polypeptide in a prokaryotic host, for example, for expression in E. coli. The N-terminal methionine can optionally be cleaved from the expressed BACE polypeptide. The polynucleotide can also encode other N-terminal amino acids added to the BACE polypeptide that facilitate expression in E. coli. Such amino acids include, but are not limited to, a T7 leader sequence, a T7-caspase 8 leader sequence, and known tags for purification such as the T7-Tag MASMTG-GQQMGR [SEQ ID NO: 8] that allows binding of antibodies, or a six-histidine tag ($His$)$_6$ that allows purification by binding to nickel. Other useful peptide tags include the thioredoxin tag, hemaglutinin tag, and GST tag. These and other amino acid tags can be encoded by polynucleotides added to either terminus of the polynucleotide encoding BACE. In addition, the wild-type polynucleotide sequence expressing human BACE can be mutated to provide for codons preferred for the expression of BACE in E. coli or other desirable host.

The polynucleotide of the expression construct can encode a BACE polypeptide that is truncated by removal of all or a portion of the cytoplasmic tail, the prosequence, the transmembrane domain, the membrane proximal region, or any combination of these. The expression constructs can also encode cleavage sites for selected enzymes, to improve purification of the expressed protein or to assist in expression of the enzyme, when desired.

It has been found that active recombinant BACE protein can be expressed from constructs encoding protein having an N-terminal amino acid within the protease domain; that is, the amino acid sequence of the BACE protein can begin at positions downstream of $T^1$, for example at $R^{36}$ and $F^{39}$. In addition, as shown in FIG. 1 [SEQ ID NO:1], expressed BACE protein can terminate at $S^{432}$, lacking the transmembrane domain and cytosolic tail region. This provides BACE in a soluble form, that is, a form that is not membrane-bound.

For efficient expression, one or more codons of the polynucleotide sequence encoding BACE can be modified, using such techniques as site directed mutagenesis, to eliminate GC-rich regions of strong secondary structure known to interfere with efficient cloning or expression of the recombinant protein. Codons can also be optimized for expression in E. coli, for example, according to published codon preferences.

Examples of suitable constructs for expression in *E. coli* are presented in Table 1, where $T^1$ denotes the first amino acid of the prosequence, and amino acids are numbered accordingly. It will be understood that modifications to the specific constructs identified herein can be made within the scope of the invention.

TABLE 1

Expression Constructs Encoding BACE, Suitable for Expression in *E. coli* Construct

| Number | (Vector - Encoded polypeptide) |
|---|---|
| B1 | pET11a-T7.Tag-Gly-Ser-Met-($A^{-8}GV \ldots QTDES^{432}$) [SEQ ID NO: 5] |
| B2 | pQE80L-Met-Arg-Gly-Ser-$(His)_6$-Gly-Ser-Ile-Glu-Thr-Asp-($T^1QH \ldots QTDES^{432}$) [SEQ ID NO: 7] |
| B4 | pQE70-(M)$R^{36}$GSFVE $\ldots QTDES^{432}$ $RS(His)_6$ [SEQ ID NO: 3] |
| B5 | pET11a-T7.Tag-Gly-Ser-Met-($A^{-8}GV \ldots R^{168}(\Delta 25)L^{194} \ldots QTDES^{432}$) [SEQ ID NO: 25] |
| B6 | pQET11a-T7.Tag-Gly-Ser-Met-($A^{-8}GV \ldots L^{124}(\Delta 44)P^{169} \ldots QTDES^{432}$) [SEQ ID NO: 27] |

In Table 1, the constructs are numbered (B1, B2, B4, B5, and B6) for convenience. Shown in the table are the vector name, for example, pET23a, pQE70, pQE80L, and PET11a. pET-derived vectors (pET23a and pET11a) are commercially available from Novagen, Inc., Madison, Wis.; pQE70 and pQE80L are commercially available from Qiagen, Inc., Valencia, Calif.

These vectors all contain the inducible lac promoter. Exogenous sequences encoding amino acid tags, leaders, and the like, are inserted upstream of the nucleic acid sequence encoding the BACE polypeptide of the construct. The table illustrates the expression constructs according to the amino acid sequence encoded by the nucleic acids of the construct.

Construct B1 encodes a BACE polypeptide that begins within the leader sequence, at $Ala^{-8}$ [SEQ ID NO:5]. Construct B2 encodes a BACE polypeptide that begins at $T^1$ [SEQ ID NO:7]. Each of B1 and B2 encode a BACE polypeptide lacking a transmembrane domain and cytoplasmic tail. The DNA and predicted amino acid sequences of these constructs is shown in FIGS. 2A-2C [SEQ ID NO:4] [SEQ ID NO:5] and 3A-3C [SEQ ID NO:6] [SEQ ID NO:7].

Construct B4 encodes a BACE polypeptide lacking the BACE prosequence as well as a portion of the N-terminal region of the protease domain [SEQ ID NO:3]. In this construct, the BACE polynucleotide insert encodes amino acids $R^{36}$ through $S^{432}$. This construct does not encode a prosequence, but rather each encodes a protein that begins within the protease domain of BACE. As shown in the Examples below, it has surprisingly been found that the prosequence is not required for proper refolding of expressed recombinant active BACE. The DNA [SEQ ID NO:2] and predicted amino acid sequence [SEQ ID NO:3] of this construct is shown in FIGS. 4A and 4B.

Constructs B5 and B6 each encode a BACE polypeptide having amino acid deletions within the protease domain of BACE. B5 contains a polynucleotide insert of BACE cDNA obtained from brain, encoding a protein that lacks 25 amino acids between $R^{168}$ and $L^{194}$ [SEQ ID NO:25]. B6 contains a polynucleotide insert of BACE cDNA obtained from pancreas, encoding a protein that lacks 44 amino acids between $L^{124}$ and $P^{169}$ [SEQ ID NO:27]. Each of these constructs expresses BACE polypeptide in *E. coli*.

Production of BACE in *E. coli*

An expression construct containing a polynucleotide encoding BACE can be used to transform bacteria, for example *E. coli*, in order to produce BACE protein. Production of the protein can be inducible or constitutive, depending upon the control elements provided in the vectors. For example, expression constructs are transfected into a bacterial host, such as *E. coli* BL21 codon plus (DE3) RP (Stratagene) and grown in suitable media, such as Luria broth supplemented with 100 micrograms/ml ampicillin and 34 micrograms/ml chloromphenicol. When cells have grown to a desired density, in general, when the absorbance of the culture at 550 nm is between 0.5 and 0.6, expression is induced. For example, in the expression vectors listed in Table 1, the T7 or T5 lac promoter promotes expression of the operably linked BACE polynucleotide upon addition of IPTG (for example, to a final concentration of about 1 mM) to the culture media. After induction, for example, about three hours, the cell pellet is collected and can be stored, generally at −70° C., for later inclusion body isolation, enzyme refolding and purification.

The expressed recombinant enzyme accumulates intracellularly in an insoluble form, as inclusion bodies. To recover the enzyme from insoluble cellular material, bacterial cells are pelleted from the bacterial cell culture, lysed, and the inclusion bodies are isolated from the lysed cells. The recombinant enzyme can then be isolated from the isolated inclusion bodies.

Generally, lysing of cells to obtain the protein inclusion bodies can be accomplished using a number of known methods, including mechanical and chemical techniques. Sonication and freeze-thaw techniques are generally not practical for the volume of cells being disrupted. However, any commercially available device that uses a pressure differential to disrupt the cells, such as a French Press or a Rannie apparatus, is acceptable, assuming the overall handling capacity is similar or greater than these instruments. Detergent solubilization is not generally a practical solution, since removal of the detergent can pose a difficult challenge and may influence subsequent refolding efforts. Detergents may solubilize contaminating proteins and nucleic acids together with some or all of the protein of interest from the inclusion bodies, and thus is not a desirable option. Once the cells have been lysed, the inclusion bodies may be washed to remove protein contaminants associated with or entrapped in the inclusion bodies.

For example, to obtain inclusion bodies, bacterial cells can be suspended in a suitable buffer that may contain a salt such as sodium chloride, a chelating agent such as EDTA, or both. Suspended cells are then lysed using, for example, a French Press or a Rannie apparatus. The insoluble cellular material obtained is washed in buffer and can be stored and frozen at −20° C.

Protein aggregates (inclusion bodies) are solubilized and then refolded to obtain active protein. Reagents that can be used to solubilize BACE include denaturants such as urea, guanidine HCl, guanidine thiocyanate, and the like, generally at a concentration of about 6M to 8M. Reducing agents, such as beta-mercaptoethanol (BME), glutathione (gamma-Glu-Cys-Gly; or GSH, Sigma Cat. No. G-6529); or DTT (dithiothreitol, Sigma Cat. No. D-0632), and the like can also be used. These reducing agents can be used separately or in combination to provide the isolated protein in a reduced form (random coil). The reducing agents can reduce the presence of dimers and higher molecular weight multimers, as well as reduce improper folding, for example, as a result of cysteine residues within the protein, or reduce aggregation of the protein.

Solubilization of BACE present in inclusion bodies can be achieved via treatment with a solubilizing agent (denaturant) at a high pH (about pH 10-11), and in the presence of a reducing agent such as BME. For example, insoluble cellular material can be solubilized and the enzyme provided in reduced form by washing in 10 mM Tris HCl buffer (pH 8), 1 mM EDTA (TE). Inclusion bodies are then extracted with 7.5 M urea, 100 mM BME, and 100 mM AMPSO (3-[(1,1-dimethyl-2-hydroxyethyl)amino]-2-hydroxypropanesulfonic acid, Sigma Cat. No. A1911) at pH 10.5-11.0. After centrifugation, the protein concentration of the supernatant can be adjusted by dilution with a solution of the denaturant, e.g. 7.5 M urea, in a suitable buffer 100 mM AMPSO to read approximately 0.1 to 4.0, preferably about 0.5 to 3.0 at $A_{280}$. Other buffer solutions can be substituted for AMPSO, such as Tris HCl or CAPS (3-[cyclohexylamino]-1-propanesulfonic acid, Sigma Cat. No. C-2632).

Refolding of Isolated Recombinant Enzyme

Once the protein has been solubilized, it can be refolded into the correct conformation to provide active enzyme. Typically, refolding of an expressed recombinant enzyme can be accomplished by removing the solubilizing agent and replacing it with an aqueous buffer, for example, by dialysis or dilution. Generally, for proteins with disulfide bridges, oxidation of the reduced protein occurs prior to or concomitant with refolding.

Generally, refolding of recombinant BACE is accomplished by permitting the diluted enzyme solution (at about pH 10-11) to incubate in a cold room (1° C. to abut 15° C.) for about three days to several weeks. The time of the incubation depends upon the construct used to express the recombinant BACE. For example, it has been found that the BACE lacking its prosequence requires from 3 weeks to about 6 weeks of incubation to achieve maximal enzyme activity, while BACE sequences having an intact prosequence require about 2 to 6 days of incubation.

As shown in the Examples below, solubilized, recombinant BACE can be diluted in water (about 10-150 fold), preferably to a final concentration of approximately 5 to 50 micrograms BACE per ml of solution, and generally at a pH of about 10.5-10.8. This mixture is maintained at temperatures of approximately 1° C. to approximately 15° C. for several days or weeks and assayed periodically for enzymatic activity. Activity assays can be performed starting at any time. Generally, activity of the re-folded enzyme will be apparent at about 20 to 24 hours after the initial dilution step.

In one aspect of the invention, the solubilized BACE, prior to dilution, has an absorbance reading of about 0.1 to about 4.0 at 280 nm. Upon dilution of about 10 to about 150 fold, the concentration of the enzyme is expected to be in the range of about 5-50 micrograms/ml. However, it is expected that other higher or lower concentrations will produce an active protein. For example, it is expected that the recombinant BACE enzyme will properly refold in concentrations from about 1 microgram/ml to about 300 micrograms/ml. Thus, the absorbance of the solubilized BACE solution may be higher or lower, and the solution may be diluted to a greater or lesser extent than 10-150 fold, depending upon the starting concentration (as shown by the absorbance or otherwise) of the solubilized BACE. The extent of protein activity of the refolded protein can be readily determined using the activity assay described herein. Accordingly, for the purposes herein, dilution of the solubilized BACE refers to the process of diluting a solution of solubilized BACE to provide a concentration of recombinant BACE capable of refolding to an active enzyme upon incubation in a cold room from a few days to several weeks.

For example, using the method of the present invention, pET11a-BACE [SEQ ID NO:5] and pQE80L-BACE [SEQ ID NO:7] were denatured in the presence of a reducing agent at pH 10.5-10.8 as described in Example 4. This solution was diluted with the reducing agent until the absorbance of the solution was 0.4-0.7 at 280 nm. The solution was then diluted about 20-25 fold with cold water and allowed to incubate in a cold room for 3-4 days. This method produced an enzyme having an activity, compared to BACE expressed in CHO cells, of about 57% for pQE80L-BACE [SEQ ID NO:7] and about 47% for pET11a BACE [SEQ ID NO:5]. Using this method, pQE70-BACE [SEQ ID NO:3] exhibited about 97% activity compared to CHO-BACE [SEQ ID NO:23], but it required 6 weeks of incubation to achieve this activity.

In order to shorten the incubation time for pQE70-BACE [SEQ ID NO:3], a series of experiments was performed as described in Example 5. In a first experiment, the absorbance of the solubilized BACE solution was adjusted to 1.5 at 280 nm before the solution was split into the three samples having their pH adjusted to 10.0, 10.5 and 11.0. Each of these samples was then split into ten portions and diluted from 20 to 150 fold. While activity was observed for every dilution, it was observed that the best activity was achieved with a 20 fold dilution, while 35 and 50 fold dilutions also provided an enzyme having superior activity.

In a second experiment to optimize the refolding procedure for pQE70-BACE [SEQ ID NO:3], protein concentrations reading 0.5, 1.5 and 3.0 at 280 nm were split into three samples and diluted 20, 35 and 50 fold. As shown in FIG. 5, it was observed that the best activity was achieved by starting with an absorbance of 3.0 and diluting 50 fold, while dilutions of 20 and 35 fold also provided an enzyme having superior activity.

Purification of Refolded Enzyme

The refolded enzyme can be purified using standard liquid chromatography techniques, such as, for example, cation or anion exchange chromatography (available, for example, from Amersham Pharmacia Biotech), hydrophobic interaction (available, for example, from Toso Haas), dye interaction (available, for example from Sigma), ceramic hydroxyapatite (available, for example, for Bio-Rad), affinity chromatography (for example, using an inhibitor that binds active enzyme), or size exclusion chromatography (for example, Sephacryl-S100 or S200 column purification as well as resins from BioRad, Toso Haas, Sigma, and Amersham Pharmacia Biotech). One or a combination of these purification techniques can be used according to the invention to provide purified, recombinant BACE. Anion exchange chromatography using, for example, Q-sepharose, Mono-Q, or Resource Q column purification provides useful separation.

Figure 7:
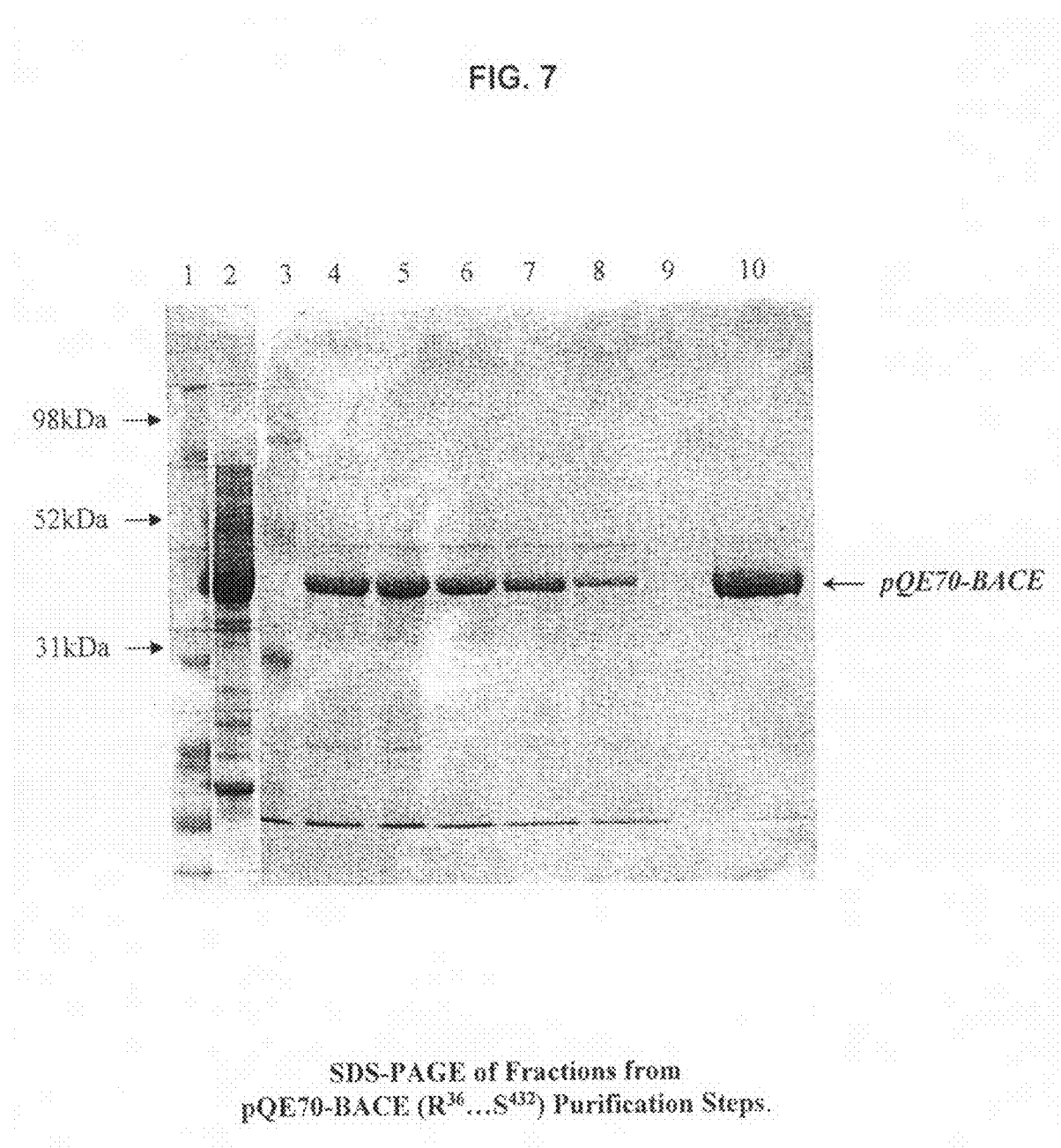
FIG. 7 shows photographs of gels showing the progression of BACE polypeptide purification from expressed inclusion bodies through chromatographic purification columns. Lanes 1 and 3, Standards. Lane 2, insoluble fraction. Lane 4, post Q column. Lane 5, post Q column, after the sample was dialyzed. Lane 6, sample of lane 5 was adjusted to pH 5.7. Lane 7, affinity feed. Lane 8, affinity flow through. Lane 9, wash. Lane 10, affinity elution.

For example, following incubation, the refolded BACE can be loaded onto an ion exchange column, for example a Q-SEPHOSE, optionally followed by a column for size exclusion, for example Sephacryl. As shown in FIGS. 6 and 7, while these procedures remove nucleic acids and afford more than a 100 fold concentration of refolded enzyme, there is no significant reduction in foreign protein. Thus the sample may be further purified with affinity chromatagraphy. In a preferred embodiment, the inhibitor for affinity chromatography is inhibitor I-1 as further described in Example 7.

Optional HIV-1 Protease Treatment of Recombinant Enzyme

The refolded BACE polypeptide can be treated with a cleavage enzyme, for example, HIV-1 protease. It has been found that treatment with HIV-1 protease results in cleavage of BACE at two sites, a major cleavage site and a minor cleavage site. N-terminal amino acid sequencing demonstrated that the major cleavage occurs between amino acids $F^{39}$ and $V^{40}$ of BACE, and the minor cleavage occurs between amino acids $Y^{163}$ and $A^{164}$. Presently it is understood that the minor cleavage concerns only unfolded BACE and, therefore, such cleavage removes inactive enzyme. After treatment with HIV-1 protease, the enzyme BACE polypeptide can be subjected to additional purification steps. As shown in the Examples, treatment with HIV-1 protease can result in a 5-fold to 9-fold increase in enzyme activity versus untreated enzymes expressed from constructs B1 and B2. According to some embodiments of the invention, treatment with HIV-1 protease can produce a homogeneous preparation of BACE with residue $V^{40}$ at its N-terminus [SEQ ID NO:31].

Cleavage with HIV protease can be performed, for example, under the following conditions: pH 4-7, 0.5 M-3 M urea, up to 2 hours incubation with HIV-1 protease, $8.7 \times 10^{-8}$ molar and BACE, $1.705 \times 10^{-6}$ molar, at 37° C. In one example, HIV-1 protease cleavage can be performed at pH 5.7, 0.5 M Urea, 5% molar concentration HIV-1 protease (4.08% w/w), BACE, about 2.5 mg/ml, for one hour at 37° C.

Activity of Refolded BACE

Activity of the refolded, purified recombinant BACE can be determined by incubating the refolded enzyme with a suitable substrate under conditions to allow cleavage of the substrate. The substrate can be labeled with a detectable marker, such as a fluorescent label, to allow detection of cleavage events.

Suitable substrates are peptides that include a BACE cleavage site. For example, the synthetic peptides SEISY-EVEFR-WKK [SEQ ID NO: 9] and GLTNIKTEEISEISY-EVEFR-WKK [SEQ ID NO: 10] can be cleaved by the recombinant BACE (site marked by "-"). Additional substrates suitable for BACE cleavage include SEVNL-DAEFRWKK [SEQ ID NO: 11] and GLTNIKTEEISEVNL-DAEFRWKK [SEQ ID NO: 12], containing the APP Swedish Mutation.

The substrate can be labeled with a suitable detectable marker to permit visualization of cleavage. Assays to detect activity of recombinantly produced BACE can measure retention or liberation of the detectable marker. Suitable detectable markers include, for example, radioactive, enzymatic, chemiluminescent, or fluorescent labels. In some embodiments, the substrate can include internally quenched labels that result in increased detection after cleavage of the substrate. The substrate can be modified to include a paired fluorophore and quencher including, but not limited to, 7-amino-4-methyl coumarin and dinitrophenol, respectively, such that cleavage of the substrate by BACE results in increased fluorescence as a result of physical separation of the fluorophore and quencher. Other paired fluorophores and quenchers include bodipy-tetramethylrhodamine and QSY-5 (Molecular Probes, Inc.).

In a variant of this embodiment, biotin or another suitable tag can be placed on one end of the peptide to anchor the peptide to a substrate assay plate, and a fluorophore can be placed at the other end of the peptide. Useful fluorophores include those listed herein, as well as Europium labels such as W8044 (EG&G Wallac, Inc.). One exemplary label is Oregon green that can be coupled to a cysteine residue. Cleavage of the substrate by BACE will release the fluorophore or other tag from the plate, allowing detection of an increase in retained fluorescence.

Further examples of detectable markers include a reporter protein amino acid sequence coupled to the substrate. Exemplary reporter proteins include a fluorescing protein (for example, green fluorescing proteins, luciferase, and the like) or an enzyme that is used to cleave a substrate to produce a colorimetric cleavage product. Also contemplated are tag sequences that are commonly used as epitopes for quantitative assays. Preferably, the detectable markers do not interfere with binding of BACE to the substrate, or subsequent cleavage of the substrate. For example, detectable markers can be provided in a suitable size that does not interfere with BACE activity. In some embodiments, detectable markers can be coupled to the substrate using spacers.

Table 2 shows a comparison of yields and activities of recombinant BACE expressed in CHO cells and E. coli (referred to 10 liters of cell culture) for the constructs B1 [SEQ ID NO:5], B2 [SEQ ID NO:7] and B4 [SEQ ID NO:3], including enzymes subjected to HIV protease.

TABLE 2

| Expression Source | BACE Construct | Amount Purified (mg) | Activity % |
|---|---|---|---|
| CHO | PcDNA3.1Asp2LΔTM(His)$_6$ [SEQ ID NO: 23] | 19 | 100 |
| CHO | PcDNA3.1Asp2LΔTM(His)$_6$ + HIV Pr [SEQ ID NO: 32] | 13 | 120 |
| E. coli | pET11a-BACE [SEQ ID NO: 5] | 55 | 47 |
| E. coli | pET11a-BACE + HIV Pr [SEQ ID NO: 31] | 28 | 248 |
| E. coli | pQE80L-BACE [SEQ ID NO: 7] | 103 | 57 |
| E. coli | pQE80L-BACE + HIV Pr [SEQ ID NO: 31] | 65 | 222 |
| E. coli | pQE70-BACE [SEQ ID NO: 3] (from Example 4) | 45 | 97 |
| E. coli | pQE70-BACE [SEQ ID NO: 3] (from Example 5 -- "optimized refolding method"): | | |
| | first elution | 54 | 171 |
| | second elution | 19 | 125 |

Table 2 shows a comparison of the yields and activities for pQE70-BACE($R^{36}$...$S^{432}$) [SEQ ID NO:3] to those obtained for pET11a-BACE($A^{-8}$...$S^{432}$) [SEQ ID NO:5] and pQE80L-BACE [SEQ ID NO:7]. Also, the yield of $V^{40}$E ... ES$^{432}$ fragment [SEQ ID NO:31] obtained by HIV protease treatment of pET11a-BACE [SEQ ID NO:5] and pQE80L-BACE [SEQ ID NO:7] is given along with that of the recombinant enzyme from CHO cells (control). The pET11a-BACE [SEQ ID NO:5] and pQE70-BACE [SEQ ID NO:3] constructs expressed in E. coli and purified to homogeneity by the affinity column had 47% and 171% activity, respectively, relative to the CHO cell derived enzyme. The fragment $V^{40}$E ... ES$^{432}$ BACE [SEQ ID NO:31] obtained by treating the pET11a-BACE [SEQ ID NO:5] construct with the HIV-1 protease was about 5 times more active than the starting construct. N-terminal sequencing and compositional analysis confirmed the absence of HIV protease in the sample.

Additional comparisons of pQE70-BACE [SEQ ID NO:3] from E. Coli, and BACE expressed in CHO cells (PcDNA3.1Asp2LΔTM(His)$_6$ as described herein, have been conducted. Specifically, the two enzymes were compared for $V_{max}$, $k_{cat}$, and $K_m$. As shown here, the two forms of BACE exhibited similar kinetic parameters. Assays were carried out in 10 mM of each sodium acetate and MES, pH 5.5, 50 mM NaCl, and substrate concentrations from 1 to 300 μM, at 37° C. for 1 h with enzyme concentrations of 1 nM. The results are shown in Table 3.

TABLE 3

| Source | Substrate Sequence | $V_{max}$ ($\mu$mol min$^{-1}$mg$^{-1}$) | $k_{cat}$ (sec$^{-1}$) | $K_m$ ($\mu$M) | $k_{cat}/K_m$ (sec$^{-1}\mu$M$^{-1}$) |
|---|---|---|---|---|---|
| CHO | GLTNIKTEEISEISY-↓-EVEFRWKK | 0.435 | 0.345 | 4.9 | 0.0704 |
| E.coli | [SEQ ID NO: 10] | 0.400 | 0.317 | 5.4 | 0.0581 |
| CHO | SEISY-↓-EVEFRWKK | 0.294 | 0.233 | 52.0 | 0.0045 |
| E.coli | [SEQ ID NO: 9] | 0.345 | 0.273 | 55.5 | 0.0049 |
| CHO | EIDL-↓-MVLDWHDR | 0.0196 | 0.0155 | 12.0 | 0.0013 |
| E.coli | [SEQ ID NO: 13] | ND | ND | | |

Having generally described the invention, the same can be more readily understood by reference to the following examples, which are provided by way of illustration and are not intended as limiting.

EXAMPLES

Example 1

Preparation of BACE Constructs B1 and B2

Expression constructs for producing recombinant BACE fragments in *E. coli* were prepared using the vector pQE11a from Novagen and vectors pQE80L and pQE70 from Qiagen. The nucleotide sequence encoding for BACE was amplified by PCR from a full length cDNA template as described in WO 00/17369, which is incorporated herein by reference in its entirety. DNA encoding the desired human BACE polypeptide, modified by site-directed mutagenesis to contain preferred codons for expression in *E. coli* were inserted into the vectors. Expression constructs B1 [SEQ ID NO:4], and B2 [SEQ ID NO:6] (See Table 1) were developed using fragments of this modified codon sequence, having codon changes as compared with the unmodified sequence encoding BACE, shown in bold type in FIGS. 2A [SEQ ID NO:4] and 3A [SEQ ID NO:6].

Three specific BACE constructs (B1, B2, and B4) were produced:

B1—T7 tag (MASMTGGQQMGR)-GSM-BACE (A$^{-8}$GVLP . . . TQTDES$^{432}$) [SEQ ID NO. 5], referred to below as pET11a-BACE, and in Table 1 as construct B1. The DNA insert of this construct encodes a BACE fragment that is truncated at both the N-terminal and C-terminal regions as compared with the sequence shown in FIG. 1 [SEQ ID NO:1]. The insert encodes a protein lacking the transmembrane domain and a portion of the pre-sequence (leader sequence) domains of BACE, shown in FIG. 1 [SEQ ID NO:1]. A codon for methionine is inserted adjacent the first BACE codon to facilitate expression in prokaryotic cells. The construct also includes the T7 lac promoter, permitting induced expression on addition of IPTG. The DNA [SEQ ID NO:4] and predicted amino acid sequence [SEQ ID NO:5] of this construct is shown in FIGS. 2A-2C.

B2—pQE80L-M-R-G-S-(H)$_6$-G-S-I-E-T-D-(T$^1$ . . . S$^{432}$) [SEQ ID NO: 7], referred to below as pQE80L-BACE, and in Table 1 as construct B2. The DNA insert of this construct encodes a BACE fragment that is truncated at both the N-terminal and C-terminal regions. The encoded fragment lacks the transmembrane domain as well as the pre-sequence the BACE protein shown in FIG. 1 [SEQ ID NO:1]. This construct further contains nucleotides encoding a Caspase-8 recognition site, IETD (bolded) [SEQ ID NO:30], enabling cleavage of the expressed BACE polypeptide at the T$^1$ position, as well as a His$_6$ purification tag. The construct also includes the T5 lac promoter, permitting induced expression on addition of IPTG. The DNA [SEQ ID NO:6] and predicted amino acid sequence [SEQ ID NO:7] of this construct is shown in FIGS. 3A-3C.

B4—pQE70-(M)R$^{36}$GSFVE . . . QTDES$^{432}$RS(His)$_6$ [SEQ ID NO: 7], referred to below as pQE70-BACE and in Table 1 as construct B4. The DNA insert for this construct encodes a BACE fragment that is truncated at both the N-terminal and C-terminal regions. The encoded fragment lacks the transmembrane domain as well as both the pre-sequence and pro-sequence of BACE shown in FIG. 1 [SEQ ID NO:1]. A codon for methionine is inserted adjacent the first BACE codon to facilitate expression in prokaryotic cells. A C-terminal polyhistidine is provided by the vector. The DNA [SEQ ID NO:2] and predicted amino acid sequence [SEQ ID NO:3] of this construct is shown in FIGS. 4A and 4B.

Production of pET11a-BACE. To produce the B1 construct, pET11a-BACE: T7 tag (MASMTGGQQMGR)-GSM-BACE (A$^{-8}$GVLP . . . TQTDES$^{432}$) [SEQ ID NO:5], the DNA insert was amplified by PCR in a series of steps. BACE-encoding polynucleotides 1 to 580 were amplified from a pET11a-BACE construct [SEQ ID NO:4] that was truncated at the C-terminus and contained only 4 cysteine residues. This template was chosen because it contained nucleic acid sequences upstream from pQE 80L-BACE construct [SEQ ID NO:6] and also included codon changes for preferred expression in *E. coli*. The PCR primers were:

```
PF3 5' ggcaggatcc atg gct ggt gtt ctg cca gct ca 3' (forward),   [SEQ ID NO: 14]
and PR4 5' tgcc act gtc cac aat gct c 3' (reverse).                  [SEQ ID NO: 15]
```

An overlapping segment including the rest of the C-terminal amino acids was amplified in a separate PCR, using primers:

```
PR5 5' ggcaggatccta tga ctc atc tgt ctg tgg aat 3' (reverse)   [SEQ ID NO: 16]
and PF6 5' g agc att gtg gac agt ggc a 3' (forward).               [SEQ ID NO: 17]
```

The products obtained from these two PCR amplifications were joined together in a third PCR amplification using the external primers PF3 and PR5. This final product was gel purified, digested with BamHI and ligated into the corresponding site of vector pQE11a. The complete DNA [SEQ ID NO:4] and amino acid sequence [SEQ ID NO:5] for the pET11a-BACE construct is shown in FIGS. 2A-2C. The first fifteen amino acids (underlined) correspond to the vector's T7 tag and contain a BamHI cloning site as well as an additional methionine. Codon changes as preferred for expression in *E. coli* are shown in bold type. PCR conditions were as follows: one initial cycle of denaturation at 95° C., 30 seconds, 30 cycles of 30 seconds denaturation at 95° C., 30 seconds annealing at 60° C., 2 minutes extension at 72° C., followed by one cycle of 5 minutes at 72° C. The reaction components were: 1×cloned Pfu polymerase buffer (Stratagene), 100 µM each dNTP, 100 ng each primer, 10 ng template DNA, and 2T1 (20 units) of cloned Pfu DNA polymerase.

Production of pQE80L-BACE: Primers used to amplify the BACE DNA insert for pQE80L-BACE: MRGS (His)$_6$-GS-IETD-BACE (T$^1$QH . . . TDES$^{432}$) [SEQ ID NO:7] were:

The PCR reaction contained 100 ng of plasmid DNA template, 100 ng of each primer, 0.25 mM each dNTPs, and 2 units of Pfu DNA Polymerase in the buffer provided by the manufacturer. Cycling parameters included an initial denaturation at 92° C. for 5 min. followed by 25 cycles of 30 sec denaturation at 92° C., 30 sec. annealing at 60° C. and 2 min. extension at 72° C., plus a final cycle with a 5 min. extension at 72° C. The PCR product was fractionated in a 1% agarose gel. The desired band was excised and purified by Geneclean. The purified fragment was digested with SphI I and Bgl II, purified in the same manner and ligated to the corresponding sites of the vector pQE70.

Example 2

Transformation of Host Cells, Cell Incubation and Analysis.

The expression constructs produced BACE polypeptide as inclusion bodies. The inclusion bodies developed after approximately two hours of induction, and, due to their large size, were readily visible by light microscopy.

Expression of constructs B1 and B2 and analysis of cell pellets: For constructs B1 [SEQ ID NO:4] and B2 [SEQ ID

```
PF9  5' gctaaggatcc atc gag acc gac acc caa cat ggt att cgt ctg c  [SEQ ID NO: 18]

PF10 5' gctaaggatcc atc gag acc (forward);                          [SEQ ID NO: 19]
and PR11 5' ggcaagctt atc atg act cat ctg tct gtg gaa tg (reverse).     [SEQ ID NO: 20]
```

PCR reagents and conditions were the same as described above. The PCR product was gel purified, digested with BamHI/HindIII and ligated to the corresponding sites of vector pQE80L. The resulting construct is shown in FIGS. 3A-3C [SEQ ID NO:6]. A caspase-8 cleavage site and nucleotide changes according to *E. coli* codon preference are shown in the nucleotide sequence of FIG. 3A [SEQ ID NO:6] in bold type. The N-terminal vector derived sequence, including the polyhistidine handle and BamHI cloning site is underlined. PCR conditions and reagents were the same as those for the production of pET11a-BACE [SEQ ID NO:4].

Construction of pQE70-BACE

The nucleotide [SEQ ID NO:2] and predicted amino acid sequence [SEQ ID NO:3] of the pQE70-BACE construct is given in FIGS. 4A and 4B. The codon for R$^{36}$ was changed from aag to cgt, in order to conserve the vector's SphI cloning site. Primers specific to the desired BACE sequence were designed as follows:

NO:6], ligated DNA was transformed into *E. coli* DH5α for propagation and DNA isolation, and into *E. coli* BL21 CodonPlus Rp (for construct B2) and CodonPlus (DE3) Rp (for construct B1) for expression. Transformed cells were inoculated into and grown in Luria Broth, pH 7.5 containing 100 µg/ml ampicillin and 34 µg/ml chloromphenicol, at 37° C. and shaken at 200 rpm (2.5 inch throw). A loop of a glycerol stock of the construct was inoculated into the media. When the absorbance of the culture at 550 nm reached approximately 0.5-0.6, cells were collected by centrifugation, resuspended in fresh media, and used as inoculum for a secondary culture at a 1:100 dilution. When cell density reached $A_{550}$=0.5-0.6, cells were harvested by centrifugation at room temperature and then resuspended at the same concentration in fresh LB, again containing ampicillin and chloromphenicol. BACE expression was induced by the addition of IPTG to a final concentration of 1 mM. Expression of the recombinant

```
AMM 510 5'ggctgc atg cgt ggc agc ttt gtg gag atg gtg g (forward), [SEQ ID NO. 21]
and AMM 514 5' ggctagatct tga ctc atc tgt ctg tgg aa (reverse).        [SEQ ID NO. 22]
``` protein was continued for 3 hours after induction ($A_{550}$=1.8-2.0). Cells were collected by centrifugation and stored at −80° C.

When expression was conducted under the same conditions but in *E. coli* BL21 or BL21(DE3) cells that lack the pACYC-based plasmid encoding rare *E. coli* codons for arginine (aga, agg) and proline (ccc), the inclusion bodies produced were smaller and did not refract light. Although successful expression of BACE constructs has been reported in BL21 cells (Tang 2001), increased yield and higher quality inclusion bodies have been observed when using the Codon-Plus cells in these studies (data not shown). The CodonPlus cells used herein perform well when induced at a density of approximately 0.5 ($A_{550}$).

Initially cultures were prepared in 100 ml of media contained in 500 ml flasks. This process was easily adaptable to a larger flask size and was scaled-up as follows. To shorten the overall length of the process, the inoculation rate for the secondary culture was increased 4-fold to a 1:25 dilution of the primary seed culture. Cultures were grown in 1.25 L of media contained in 2.8 L Fernbach flasks and the shaking rate was increased to 225 rpm.

Expression of BACE was also evaluated under conditions where the step of replacing fresh culture medium prior to induction of expression was eliminated. Under these conditions, cells were grown to an absorbance of approximately 0.75-0.85 ($A_{550}$) prior to induction with IPTG, and cells were harvested after approximately 2.5 hours of incubation. Media change before induction resulted in cells having uniform morphology at the end of the induction period, but does not appear to be required.

Figure 8:
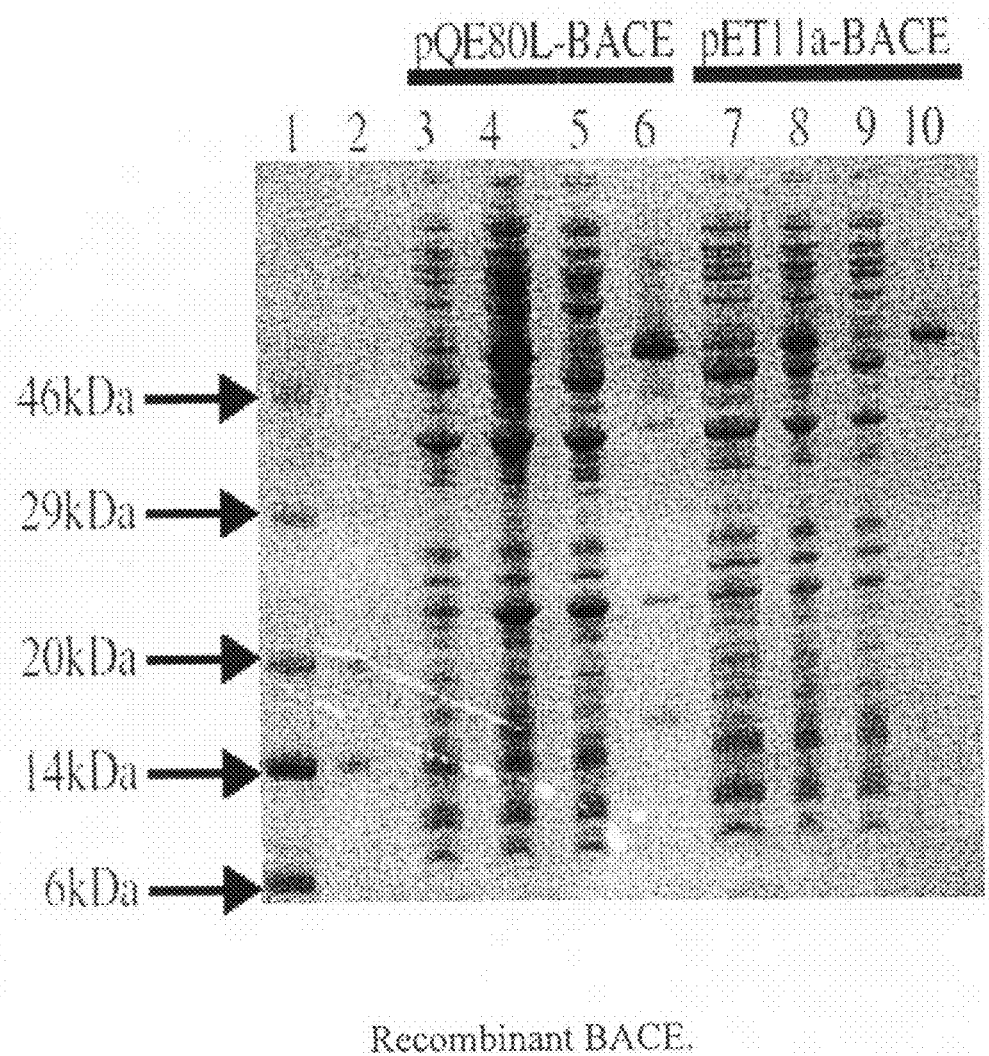
FIG. 8 is a photograph of a gel showing the results of SDS-PAGE analysis of recombinant BACE polypeptide produced in *E. coli*. Lanes 3-6 contained protein expressed from the B2 construct [SEQ ID NO:6], and lanes 7-10 contain protein expressed from B1 [SEQ ID NO:4]. Lanes 3 and 7 show total protein obtained from uninduced cells; lanes 4 and 8 show total protein from induced cells; lanes 5 and 9 show soluble protein fractions; and lanes 6 and 10 show insoluble protein fractions.

Cell pellets were resuspended in TE buffer (10 mM Tris HCl, pH 8.0, 1 mM EDTA) at a 1 in 10 dilution of the original culture volume and sonicated. The soluble protein fraction was separated from the cell debris and insoluble protein fraction by centrifugation at 10,000×g for 15 minutes. The fractions were analyzed by SDS PAGE. Total cells or protein fractions ($A_{600}$=approximately 0.1) were resuspended in SDS denaturing buffer, boiled for five minutes, and fractionated in a 4-20% gradient gel. A representative gel is shown in FIG. 8. Lanes 3-6 contained protein expressed from the B2 construct [SEQ ID NO:6], and lanes 7-10 contain protein expressed from B1 [SEQ ID NO:4]. Lanes 3 and 7 show total protein obtained from uninduced cells; lanes 4 and 8 show total protein from induced cells; lanes 5 and 9 show soluble protein fractions; and lanes 6 and 10 show insoluble protein fractions. A prominent band at about 50 kDa, the expected molecular mass of the encoded BACE fragments, appears in lanes 6 and 10, in the insoluble protein fractions.

The presence and correct orientation of the insert for the pET11a construct was confirmed by PCR, using one of the internal primers (PF6 or PR9) and the corresponding flanking primer from the pET11a vector. DNA was subjected to complete sequencing to confirm sequence inserts.

Expression of construct B4 and analysis of cell pellets: For the transformation and expression of construct B4 [SEQ ID NO:2], pQE70 was transformed into the *E. coli* expression strain BL21(pREP4) and plated on LB agar containing 100 μg/ml ampicillin and 25 μg/ml kanamycin. Selected colonies were amplified, and the isolated plasmid DNA was submitted to DISC for complete sequencing. The BL21 (pREP4) strain is the result of the transformation of transformation of the commercially available B121 (Novagen) with the plasmid pREP4 (Qiagen), which generate high levels of the lac repressor protein to ensure tight control at the transcriptional level.

An overnight culture from a single colony containing the pQE70-BACE [SEQ ID NO:2] plasmid was used to inoculate 100 ml of LB plus antibiotics. The culture was amplified at 30 or 37° C. to a density of $A_{550}$=0.6-0.7, and induced with IPTG to a final concentration of 1 mM. Expression was allowed to proceed for 2-3 hours after induction, and the cells were harvested by centrifugation. The cell pellet was resuspended in TE (10 mM Tris HCl pH 8.0, 1 mM EDTA), cells were disrupted by sonication, and products were analyzed by SDS-PAGE followed by COOMMASSIE® blue staining. The band presumed to contain the BACE protein was blotted to PDVF membrane and submitted for N-terminal sequencing. Large-scale preparations were performed in multiple 4-liter flasks, following the same conditions as for the small-scale experiments, at 37° C.

Example 3

Inclusion Body Harvest

The collected centrifuged cells (cell paste) was resuspended in TE (10 mM Tris HCl pH8.0, 1 mM EDTA) at 1/10 of the original culture volume and sonicated. The soluble protein fraction was separated from cell debris and insoluble proteins by centrifugation at 10,000×g for 15 minutes. Protein in each of the fractions was analyzed by SDS-PAGE.

To obtain inclusion bodies, cultured cells expressing constructs B1 [SEQ ID NO:5] and B2 [SEQ ID NO:7] were centrifuged to pellet the cells. Cell pellets were weighed from 10 liters of cell culture. The wet weight of the cell pellet corresponding to 10 liters of cell culture was 23.5 g. The cell pellet was resuspended in 4.0-5.0 ml of 10 mM Tris HCl, 1 mM EDTA, pH 8.1 (TE) buffer per gram of cell pellet. The re-suspended cell pellet was subjected to 16,000 psi in a French press, or to 12,000 psi in a Rannie apparatus. The resulting solution was centrifuged at 8600 rpm (8840×g) for 30 minutes in a SS34 rotor. The pellet, including insoluble material, was washed one time in 10 mM Tris HCl buffer, pH 8.1, 1 mM EDTA (TE) and centrifuged at 2900 rpm (1000×g) for 30 minutes in the SS34 rotor. The wet weight of the inclusion bodies was 2.67 g. The inclusion bodies were either frozen at −20° C. for use at a later time or immediately extracted as described in the further Examples.

For construct B4 [SEQ ID NO:3], the wet weight of the cell pellet corresponding to 10 liters of cell culture was about 23 g. The cell pellet was resuspended in 5.0 ml of 10 mM Tris HCl, 1 mM EDTA, pH 8.1 (TE) buffer per gram of cell pellet and subjected to 12,000 psi in a Rannie apparatus. The resulting solution was centrifuged at 7400 rpm (8907×g) for one hour in GSA rotor. The pellet was washed one time in TE buffer and centrifuged at 2900 rpm (1368×g) for one hour in the GSA rotor. The inclusion bodies were either frozen at −20° C. for use at a later time or immediately extracted.

Example 4

Refolding of Recombinant BACE.

Protein from the inclusion bodies was solubilized with 15-20 ml 7.5 M urea, 100 mM AMPSO, and 100 mM BME, at pH 10.5-10.8. After centrifugation at 11,900 rpm in the GSA rotor for one hour, the protein concentration of the supernatant was adjusted by dilution with the above buffer to read approximately 4.0 to 7.0 at $A_{280}$. The protein was then diluted with 8 M urea, 100 mM AMPSO, at pH=10.5-10.8 to read about 0.4 to 0.7 at $A_{280}$. Extraction has also been carried out substituting AMPSO with CAPS or Tris HCl, with similar results.

Analysis of the sample in 7.5 M urea by SDS-PAGE revealed BACE as the major component of the solubilized inclusion bodies. BACE migrated as a band of Mr=50,000.

Refolding was carried out by a 20-25 fold dilution with cold water having a temperature of approximately 4° C.-15° C. Upon dilution, the pH of the sample dropped automatically to 9.5-10.2. The sample was then allowed to rest in the cold room for several days. Activity assays were performed daily to monitor protein refolding, generally starting about 18-20 hours after the 20-25 fold dilution with water. Final pH readings were in the range of 9.5-10.2. Results from various activity assays (described below) indicated that maximal activity was usually reached at day 3 or 4 of incubation (data not shown) for enzyme expressed from constructs B1 [SEQ ID NO:4] and B2 [SEQ ID NO:6]. For enzyme expressed from construct B4 [SEQ ID NO:2], maximal activity was not reached until about 6 weeks of incubation.

Example 5

Optimization of Refolding of pQE70-BACE

In order to improve the refolding protocol for the enzyme from construct B4 [SEQ ID NO:3], a series of experiments was performed. In the first optimization step, inclusion bodies from 3L of cell culture from expression of pQE70-BACE [SEQ ID NO:3] and pET11a-BACE [SEQ ID NO:5] (as a control) were extracted with a solution composed of 7.5 M urea, 100 mM β-mercaptoethanol (BME), and 100 mM AMPSO and split in three portions. Each portion was adjusted to a different pH; specifically, pH 10.0, 10.5, and 11.0, respectively. The portions were centrifuged and their absorbances at $A_{280}$ determined. The three samples were diluted with 7.5 M urea and 100 mM AMPSO to read 1.5 at $A_{280}$ nm while their pH's were kept at 10.0, 10.5, and 11.0, respectively. Each of the three solutions was then split in ten different portions. Each portion was diluted with water at 4-15° C. to obtain ten different dilutions for each of the three samples. Specifically, 20-, 30-, 40-, 50-, 60-, 70-, 80-, 90-, 120-, and 150-fold dilutions were performed. The solutions were set-aside in the cold room. Temperature and pH of the diluted protein solutions were monitored at day 0 and day 7. BACE activity assays (described below) with substrate SEISYEVEFRWKK [SEQ ID NO. 9] were carried out at day 7 for each of the dilutions.

In the second optimization step for the expression product of construct B4 [SEQ ID NO:2], inclusion bodies from 2L of cell culture were extracted with 7.5 M urea, 100 mM BME and 100 mM AMPSO, pH 11.0 and centrifuged. Protein concentrations reading 0.5, 1.5, and 3.0 at 280 nm were selected. Each solution was split in three portions that were diluted 20-, 35-, and 50-fold respectively, with water at 4-15° C. Progress of refolding was monitored over a period of three weeks by assaying the samples daily. As a control the same experimental procedure was completed for pET11a-BACE (construct B1 [SEQ ID NO:5]). The results are reported in FIG. 5.

For large scale refolding, inclusion bodies from the expression of construct B4 [SEQ ID NO:2] were obtained from 60 L of cell culture and washed one time in 935 ml of 10 mM Tris HCl buffer, pH 8.1, 1 mM EDTA (TE). The inclusion bodies were extracted with 600 ml 7.5 M urea, 100 mM AMPSO, and 100 mM BME, pH 10.8. The extract was stirred at room temperature for 1 hour before centrifugation. After centrifugation, the protein concentration of the supernatant was adjusted by dilution with 7.5 M urea and 100 mM AMPSO, pH 10.8 to read 1.5 at $A_{280}$ Refolding was carried out by a 20 fold dilution with cold water (4-15° C.). Upon dilution, the pH dropped automatically to 10.0-10.3. The sample was then allowed to stand in the cold room. Activity assays were performed regularly to monitor protein refolding.

Example 6

Expression of BACE in CHO Cells (Control):

As a control, a BACE construct (Asp2-2LΔTM-His$_6$), referred to herein as CHO-BACE, encoding the amino acid sequence shown in FIG. 9 [SEQ ID NO: 23], was expressed in CHO cells was purified from about 75 liters of conditioned media. The purification process consisted of successive steps of tangential flow concentration, ammonium sulfate precipitation, Nickel affinity column, and affinity chromatography (I-1 affinity). The purified enzyme contained an approximately 50:50 mixture of the isoforms starting at $T^1$QHGIRL ... and $E^{25}$TDEEPEEPG ..., numbered as in FIG. 1. [SEQ ID NO:1] The two isoforms are generated by post-translational cleavage by yet unknown proteases. Activity of the CHO-BACE [SEQ ID NO:23] served as a control in the activity analysis of the recombinant BACE from constructs B1 [SEQ ID NO:5], B2 [SEQ ID NO:7] and B4 [SEQ ID NO:3] as described below.

Example 7

Purification of Recombinant BACE

To purify the refolded protein, the pH of the refolded protein was lowered from approximately 10 to 8.5 with dilute HCl and loaded onto a Q-Sepharose column (5.0×2.8 cm). BACE was eluted with 0.75 M NaCl in 0.4 M urea, 10 mM Tris HCl buffer, pH8.2. Active BACE was collected. The sample was dialysed against 20 mM Hepes, pH 8.0. After dialysis, the pH of the sample was brought to 5.7 using 1 M sodium MES, pH 5.7 (0.1 M final concentration), and centrifuged at 20,000×g for 30 minutes. The pH of the supernatant was then lowered to 5.0 with 1 M sodium acetate, 1 M sodium MES, pH 5.0 (0.2 M sodium acetate, 0.28 M sodium MES, final concentration). The sample was then centrifuged, but no pellet was observed.

The supernatant was applied to a 10 ml affinity column (SULFOLINK™ Coupling Gel, Pierce Cat. No. 204011) in an Econo column (BioRad) in an amount of 1 mg/ml of the gel, according to the manufacturer's instructions cross-linked with the Inhibitor I-1 [SEQ ID NO:28] (described below) and equilibrated at the same pH as the sample. The column was washed with 6 column volumes of 0.1 M sodium acetate, 0.1 M sodium MES, pH 5.0. BACE was eluted at pH 8.5 in 0.1 M borate buffer.

Results showed that this purification method provided a yield, from 10 liters of E. coli cell culture, of 58 mg of highly purified B1 construct [SEQ ID NO:5]. An equivalent of 1.8 liters of E. coli cell culture was affinity purified yielding 16.5 mg of highly purified B2 construct [SEQ ID NO:7]. By extrapolating, 10 liters of E. coli would be expected to yield about 92 mg enzyme. The three batches of E. coli expressing construct B4 [SEQ ID NO:3], (3.3L, 19L, and 40L, making a total of 62.3L), and refolded using the procedure described above requiring six weeks incubation for optimal activity, produced about 285 mg of pQE70-BACE($R^{36}$ ... $S^{432}$). [SEQ ID NO:3]

This method was used to purify BACE from 33 liters of E. coli cell culture from construct B1 [SEQ ID NO:5]. This yielded 147 mg of highly purified BACE. 17 mg of this preparation was passed over a Sephacryl-S200 column (2.5× 130 cm) (Amersham Pharmacia Biotech AB) to assess the aggregation state of the enzyme. It was observed that BACE migrated as a monomer, demonstrating that the affinity purification step separated monomeric from aggregated forms. A single peak of active BACE, migrating in the monomer position, was observed (data not shown).

In the first purification step (above) involving the Q-SEPHAROSE™ Fast Flow column, the sample was concentrated to remove nucleic acids present in abundance at this stage. An 8 liter enzyme sample was loaded onto a 50 column pre-equilibrated with 10 mM Tris HCl (pH 8.2), 0.4 M urea and NaCl to bring the conductivity to 0.9 mMhos (to match the ionic strength of the BACE protein solution). A linear gradient of 0-1.0 M NaCl was applied in the same buffer used to equilibrate the column. Fractions of 5.5 ml were collected. Every fifth fraction was assayed for enzymatic activity as described in Example 8. The data are shown here in Table 4. Fractions were also analyzed by SDS-PAGE (5 μl samples).

TABLE 4

Q-Sepharose Purification of Recombinant BACE

| Q-sepharose | Fluorescence peak area |
| --- | --- |
| Fraction 5 | 0 |
| Fraction 10 | 0 |
| Fraction 15 | 13 |
| Fraction 20 | 20 |
| Fraction 25 | 541 |
| Fraction 30 | ≧700 |
| Fraction 35 | 690 |
| Fraction 40 | 699 |
| Fraction 45 | 222 |
| Fraction 50 | 222 |
| Fraction 55 | 143 |
| Fraction 60 | 78 |
| Fraction 65 | 70 |
| Fraction 67 | 51 |
| Fraction 70 | 33 |
| Fraction 75 | 21 |
| Fraction 78 | 17 |

For affinity purification, affinity column was generated by coupling 1 mg of Inhibitor I-1 (shown below) per ml of SulfoLink™ Coupling Gel.

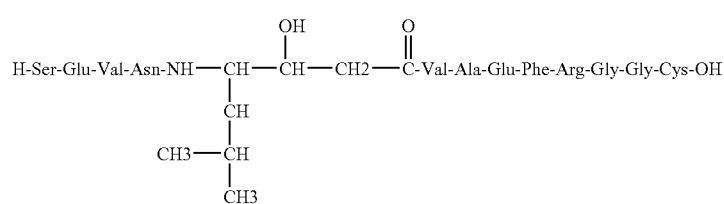

(I-1)[SEQ ID NO:28]

A summary of the activity/protein recovery at each purification step for construct B1 [SEQ ID NO:5] is shown in Table 5.

TABLE 5

Purification of Recombinant BACE Expressed in E. Coli

| Fraction | Volume (ml) | Total Protein (mg) | Total Activity (Fluorescence peak area) | % Yield |
| --- | --- | --- | --- | --- |
| 20-fold dilution (pH 8.0) step | 8,000 | Sample too diluted | $8.0 \times 10^7$ | 100 |
| Q-Sepharose | 280 | 45.3 | $3.2 \times 10^7$ | 40 |

TABLE 5-continued

Purification of Recombinant BACE Expressed in E. Coli

| Fraction | Volume (ml) | Total Protein (mg) | Total Activity (Fluorescence peak area) | % Yield |
| --- | --- | --- | --- | --- |
| Sephacryl-200 | 36 | 14.4 | $2.3 \times 10^7$ | 29 |
| Affinity | 30 | 13.8 | $2.2 \times 10^7$ | 28 |

Purification of BACE from 60 L E. coli cell culture was refolded with the optimized method. Prior to purification, the pH of the refolded protein was lowered from about 10 to 8.5 with HCl. The solution was loaded onto 200 ml Q-Sepharose in an INdEX 70 mm column (Amersham Biosciences). The column was pre-equilibrated in 0.4 M urea, 10 mM AMPSO, pH 8.5. After the refolded protein was loaded onto the column, it was washed with 2L of 0.4 M urea, 10 mM Tris HCl, pH 8.2. The column was eluted with 600 ml of 0.75 M NaCl in 0.4 M urea 10mM Tris HCl buffer, pH 8.2. The eluate was dialyzed overnight versus 10 L 20 mM HEPES, pH 8.0. The sample, 620 ml, was then removed from dialysis and dropped into 69 ml of 1 M NaMES, pH 5.7 (0.1 M NaMES was the final concentration). After centrifugation (20K×g) the supernatant was added to 172 ml of 1 M Na-acetate, 1 M NaMES, pH 5.0 (0.2 M sodium acetate, 0.28 M NaMES was the final concentration). While no precipitation was observed at this step, a slight opaqueness was observed while waiting to go over the subsequent affinity column. Consequently, this solution was applied rapidly (by gravity) to a 50 ml affinity column (SULFOLINK® gel cross-linked with inhibitor I-1 [SEQ ID NO:28]) equilibrated at the same pH. No opaqueness was observed in the resultant flow-through. After recycling the flow through over the affinity column two more times at a slower rate, the column was washed with 300 ml of 10 mM sodium acetate, 10 mM NaMES, pH 5.0. Recombinant BACE was eluted with 167 ml of 0.1 M sodium borate buffer, pH 8.5. Following the initial elution, the affinity column's wash and flow through from the first elution were re-applied to the same affinity column, recycled 3 more times, washed, and eluted as before.

The optimized method of refolding produced a total of 438 mg of highly active and purified pQE70-BACE($R^{36}$ ... $S^{432}$) [SEQ ID NO:3] from the 60 L of E. coli cell culture. Specifically, 322 mg and 116 mg were obtained from the first and second affinity column elutions, respectively. FIG. 7 shows the SDS-PAGE of fractions from pQE70-BACE (R36 ... S432) [SEQ ID NO:3] purification steps. Lanes 1 and 3, Standards. Lane 2, insoluble fraction. Lane 4, post Q column. Lane 5, post Q column, after the sample was dialyzed. Lane 6, sample of lane 5 was adjusted to pH 5.7. Lane 7, affinity feed. Lane 8, affinity flow through. Lane 9, wash. Lane 10, affinity elution

Example 8

BACE Activity Assays

Peptide substrates SEISY↓EVEFRWKK [SEQ ID NO: 9] and GLTNIKTEEISEISY↓EVEFRWKK [SEQ ID NO: 10] were synthesized by solid-phase technology (arrows indicating cleavage site). The assay mixture contained in a volume of 200 µl, 0.1 M Sodium acetate, pH 5.0, 0.5-20 nM BACE and 25 µM substrate SEISY↓EVEFRWKK [SEQ ID NO:9] or GLTNIKTEEISEISY↓EVEFRWKK [SEQ ID NO:10]. The reaction mixture was incubated for 2 hours at 37° C.; reactions were stopped with 100 µl of 4% TFA in H$_2$O. A 50 µl portion was injected into an Agilent 1100 Series HPLC equipped with an Alltech Rocket™ column (7 mm i.d.×53 mm length, C$_{18}$, 3 µm) pre-equilibrated with 88% reagent A (0.1% TFA in water), 12% reagent B (0.1% TFA in acetonitrile). The flow rate over this column was 3 ml per minute. The products (including uncleaved substrate) were eluted from the column with the following linear gradients:

| | |
|---|---|
| 0-4.0 minutes | 12-30% B |
| 4.0-6.0 minutes | 30-50% B |
| 6.0-6.5 minutes | 50-90% B |
| 6.5-7.0 minutes | 90-12% B |
| 7.0-8.0 minutes | 12% B |

The Agilent 1100 Series HPLC is equipped with a fluorescence detector that allows detection of the substrate disappearance and EVEFRWKK [SEQ ID NO:29] product formation. Activity was expressed as Fluorescence peak area generated by the liberation of a fluorescent (Tryptophan fluorescence) product upon cleavage of substrate. Fluorescence detection is monitored at 348 nM upon excitation at 280 nM.

Example 9

Amino Acid Analysis

Microwave hydrolyses using CEM Corporation's MDS 2000 microwave oven were conducted in triplicate. Hewlett Packard 300 µl microvials containing approximately 2 µg protein were placed inside a Teflon® PFA digestion vessel (CEM Corporation) containing 4 ml of 6 N HCl (Pierce Constant Boiling) with 0.5% (volume to volume) phenol (Mallinckrodt). The samples were then alternately evacuated and flushed with N$_2$ five times. The protein was hydrolyzed using a two-stage process. During the first stage 50% of full power (about 650 W) increased the temperature to 100° C. and held at that temperature for 1 min. Immediately following, 75% power increased the temperature to 150° C. and held that temperature for 25 min. After cooling, the samples were dried (Savant SpeedVac). Amino acid analyses were performed on samples derivatized using 6-aminoquinolyl-N-hydroxysuccinimidyl carbamate to yield stable ureas that fluoresce at 395 nm (Waters AccQ•Tag Chemistry Package). The samples were analyzed by reverse phase HPLC on a Hewlett Packard 1100 system and quantification was performed using Hewlett Packard's ChemStation enhanced integrator.

Automated protein and peptide sequencing was performed on an Applied Biosystems Procise 494 sequencer. Model 610A version 2.1 software was employed for data acquisition and processing.

Electrospray mass spectrometry data were collected and processed on a Micromass Quattro II quadrupole mass spectrometer. Data were transformed to a mass scale using the micromass MaxEnt deconvolution algorithm.

Example 10

Cleavage of (CHO) Pro-BACE with HIV-1 Protease

It has been found that HIV-1 protease is capable of cleaving BACE between residues $F^{39}$-$V^{40}$. This cleavage site is within the protease domain of the BACE enzyme. In this Example, HIV-1 protease was used to produce a homogeneous preparation of BACE with $V^{40}$ as an N-terminus. Optimal conditions for cleavage were determined by examining the N-terminal sequence of BACE after incubation with HIV-1 protease in various conditions (data not shown).

Recombinant BACE expressed in CHO cells was obtained as described above for Example 6. HIV cleavage was accomplished in the following manner. 4.65 ml of BACE was added to 1.163 ml of 1 M MES, pH 5.7 (no precipitate was observed). While stirring, 0.55 ml of 6 M urea was added to the above solution (some precipitate was observed). HIV-1 protease was added in an amount of 0.222 ml. The mixture was incubated for 2 hours at 37° C.

After incubation, the mixture was dialyzed versus 0.5 M urea, 0.2 M MES (pH 5.7), 4° C. using a Sepcta/Por 6™ Membrane, MWCO: 50,000 (Spectrum Laboratories, part number 132-544) overnight. After overnight incubation, the sample was changed into a solution containing 10 mM MES (pH 5.7), and 50 mM NaCl, 4° C., and allowed to continue dialyzing for an additional 8 hours. At this point, the solution was spun to remove the precipitate, and the OD of the supernatant was analyzed by absorbance at 280 nm. It was estimated, using a conversion factor of 0.685 mg/mg AU, that approximately 20.4 mg of enzyme was present at this stage.

The prepared BACE sample obtained from the preceding steps was added to 2.325 ml of 1 M sodium acetate, pH 4.5. The sample was then applied to a 2 ml affinity column that had been pre-equilibrated with 0.2 M sodium acetate, pH 4.5. The affinity column was prepared by coupling Inhibitor I-1 (1 mg/ml of resin) to 2 ml Sulfo-Link™. The flow through material was recirculated 2 times before washing the column with 20 mM sodium acetate (pH 4.5), 150 mM NaCl. The BACE was eluted into 6 ml of 0.1 M sodium borate, pH 8.5. Absorbance at 280 nm indicated a total of 13.6 mg of BACE. The affinity column was re-equilibrated, and the process repeated using the flow through. An additional 6 ml containing a total of 5.1 mg was recovered, as determined at absorbance measurement at 280 nm. Thus, a combined total of 18.7 mg of BACE was obtained after treatment of the CHO cell derived BACE with HIV-1 protease, and subsequent purification.

Purified HIV-1 protease treated BACE was assayed for activity as described above. A control included untreated BACE. Purified HIV-1 protease treated BACE expressed and purified from CHO cells, demonstrated 10-20% more enzymatic activity than untreated BACE.

Example 11

Cleavage of Recombinant BACE Expressed in *E. coli* with HIV-1 Protease

BACE was expressed from the construct B1 [SEQ ID NO:4], isolated, and refolded as described above for Example 1. The refolded protein was passed over a 50 ml Q-SEPHAROSE™ Fast Flow (Amersham Pharmacia Biotech) column. The column was pre-equilibrated with 0.4 M urea, 10 mM Tris HCl (pH 8.2), with a conductivity that was adjusted to 0.9 mMhos with sodium chloride.

After loading the material, it was washed with five column volumes of the same buffer used to pre-equilibrate the column. The bound protein was then eluted from the column in a single step using four column volumes of 0.4 M urea, 10 mM Tris HCl (pH 8.20), 0.75 M sodium chloride. A protein content of 137 mg was estimated based on absorbance at 280 nm. This material was then concentrated to 15 ml, and divided into two aliquots for the following experiments.

For the first aliquot, the BACE sample prepared (post Q-Sepharose) was treated directly with HIV-1 protease as follows. 7.5 ml of the BACE sample was dropped into 1.875 ml of 1 M MES (pH 5.7), then spun for 15 minutes at 40,000× g. To 68.5 mg ($1.365 \times 10^{-6}$ moles) of BACE, 2.6 mg ($1.3 \times 10^{-7}$ moles) of HIV-1 protease was added. A significant precipitate formed. Notwithstanding, the sample was stirred and set in a water bath at 37° C.

A sample was taken at 1 hour, 10 minutes for SDS-PAGE analysis. At 1 hour, 50 minutes, the sample was removed from the water bath and spun for 5 minutes at 40,000×g. The supernatant was then transferred to a new tube, and placed on ice while samples were analyzed by SDS-PAGE. It appeared that approximately two-thirds of the material had been cleaved by the HIV-1 protease. Ninety minutes later, 0.65 mg HIV-1 protease ($33 \times 10^{-9}$ moles) was added, and returned to the 37° C. water bath for an additional 1 hour, 40 minutes. After this latter addition, the starting BACE material was almost fully processed. SDS-PAGE demonstrated that a major (and a minor, but significant) cleavage occurred. N-terminal amino acid sequencing confirmed that the major cleavage occurred between residues $F^{39}$-$V^{40}$, and minor cleavage occurs between residues $Y^{163}$-$A^{164}$. Without intending to be bound by a particular theory, it is believed that the latter cleavage can be desirable to eliminate unfolded BACE. In addition, timed studies show near complete cleavage by 3 hours, 30 minutes.

After the final incubation with HIV-1 protease, the material was then adjusted to pH 8.0 with 3 M Tris base, and applied to a 130 cm Sephacryl S-100HR (Amersham Pharmacia Biotech) column (Spectrum, 2.5×130 cm) equilibrated in 20 mM Hepes (pH 8.0), and 50 mM NaCl, and the protein was eluted in the same buffer. The molecular sieving step was able to separate unprocessed BACE (contained in fractions 55 and 56) from the bulk of cleaved BACE (fractions 57-60).

Fractions 57-60 were pooled (approximately 28 ml), and dropped into 7 ml of 1 M sodium acetate, pH 4.50 (0.2 M final concentration). The sample was then applied to a 10 ml affinity column, and affinity purified. The resin had been cross-linked with the Inhibitor I-1, as described above. More specifically, the sample was cycled three times over the 10 ml affinity column before washing with 60 ml of 20 mM sodium acetate (pH 4.5), and 0.15 M sodium chloride. The enzyme was eluted with 30 ml of 0.1 M sodium borate, pH 8.5. SDS-PAGE shows that the affinity column separated the $V^{40}$ ... $S^{432}$ [SEQ ID NO:31] fragment from the $A^{164}$ ... $S^{432}$ [SEQ ID NO:33] fragment. The latter fragment was found in the flow through.

The sample was characterized by amino acid analysis (5.85 mg), N-terminal sequencing ($^{40}$VEMVDNL . . . ), electrospray mass spectral determination (ESMS) (43,753.6 theoretical, 43,753.9 observed), and activity assay. The activity assay showed 248% activity relative to a human BACE construct expressed in CHO cells.

Results indicated that removal of the fragment preceding $V^{40}$ and of unfolded protein results in an approximate 8- to 9-fold increase in activity of the recombinant BACE (28% to 248%).

For the second aliquot, 7.5 ml of BACE sample (post Q-Sepharose) was applied to a Sephacryl S-200 (Amersham Pharmacia Biotech) column (Spectrum, 2.5×100 cm) equilibrated with 20 mM Hepes (pH 8.0), and 50 mM NaCl, and the protein was allowed to elute in the same buffer. Fractions 42-48 of the elution (where the monomeric form would be expected to be present) were pooled and concentrated to approximately 7.5 ml. According to absorbance at 280 nm, approximately 23.3 mg ($4.64 \times 10^{-7}$ moles) of BACE was present in the sample.

The pH of the sample was adjusted to 5.7 with 1 M MES (pH 5.7) by dropping the sample into the concentrated buffer. The final concentration of MES was 0.2 M. The sample was spun at 40,000×g for 5 minutes, and the supernatant was transferred to a new tube. HIV-1 protease ($4.64 \times 10^{-7}$ moles, 0.933 mg) was added to the sample, then incubated at 37° C. for 3 hours, 45 minutes.

After incubation, the sample was removed from the 37° C. bath, and spun to remove any precipitate formed. The supernatant was transferred to a new tube at 4° C., and set aside while SDS-PAGE analysis was performed. At this point, the SDS-PAGE analysis indicated that the cleavage of BACE was approximately two-thirds complete. Therefore, 0.933 mg of HIV-1 protease was added, and the sample was returned to the 37° C. water bath for an additional 1.5 hours.

At this point, the sample was removed from the 37° C. water bath, and the pH was adjusted to 8.0 with 3 M Tris base. The sample was then spun to remove any further precipitation. The sample was then applied to a 200 cm Sephacryl S-100HR (Amersham Pharmacia Biotech) column (Spectrum, 2.5×200 cm) equilibrated with 20 mM Hepes pH 8.0, 50 mM NaCl, and the protein was allowed to elute in the same buffer. This molecular sieving step resolved the active monomeric BACE from its aggregated forms.

Fractions containing monomeric BACE were pooled, and affinity purified with a resin that had been cross-linked with the Inhibitor I-1 [SEQ ID NO:28], as described above. More specifically, fractions were pooled (approximately 35 ml) and dropped into 8.75 ml of 1 M sodium acetate (pH 4.5), in order to adjust the pH into a range that allows BACE to recognize and bind the inhibitor. The sample was cycled three times over the 10 ml affinity column before washing with 60 ml of 20 mM sodium acetate, pH 4.5, 0.15 M sodium chloride. The enzyme was eluted with 30 ml of 0.1 M sodium borate, pH 8.5.

The sample was dialyzed against 20 mM HEPES, pH 8.0, 50 mM NaCl with one change of the buffer. According to absorbance at 280 nm, the final amount of BACE was 7.59 mg. This was analyzed by amino acid analysis (8.01 mg), as well as N-terminal sequencing ($^{40}$VEMVDNL . . . ). Enzymatic activity of this preparation was also higher than that of the CHO cells derived enzyme, 222% of the CHO control.

Figure 10:
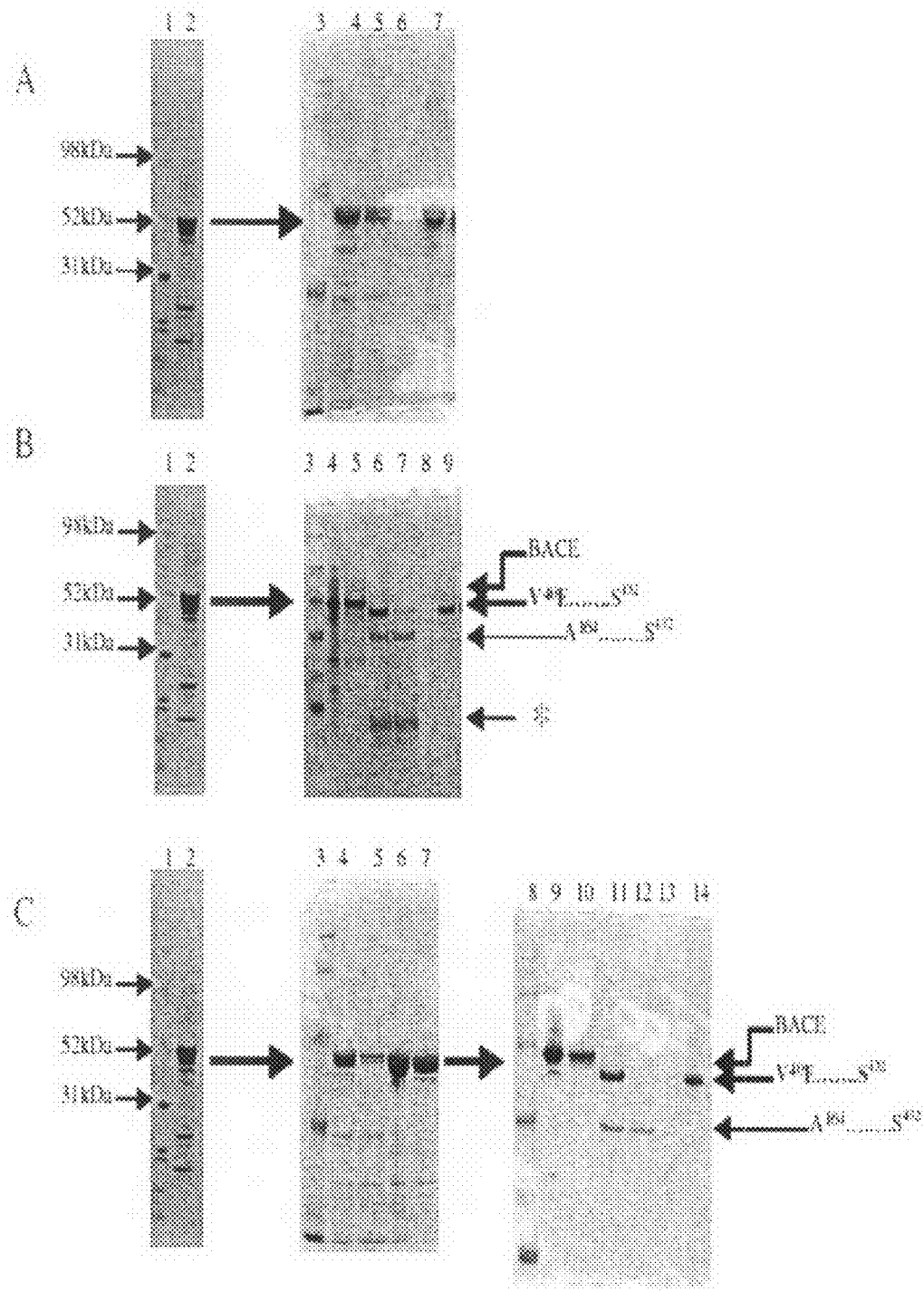
FIG. 10 is shows photographs of gels showing the progression of BACE polypeptide purification from inclusion bodies through various chromatographic columns, and also showing treatment of purified polypeptide with HIV-1 protease. Lane A2 shows inclusion bodies; lane A4 shows post Q-sepharose protein; lane A5 shows protein pre affinity chromatography; lane A6 shows the affinity column flow through; and lane A7 shows the protein product after I-1 affinity chromatography. Lane B2 shows inclusion bodies; lane B4 shows protein post-Q-sepharose; lane B6 shows protein treated with HIV-protease; lane B9 shows protein product after I-1 affinity chromatography. Lane C2 shows inclusion bodies; lane C4 shows protein post-Q-sepharose and Sepacryl-200 purification; lane C6 shows post first I-1 affinity chromatography; lanes C7 and C9 shows post-dialysis; lane C10 shows after adjustment to pH 5.7; lane C11 shows protein after HIV protease treatment; lane C14 shows the protein product after second I-1 affinity chromatography.

The sequential processing and purification of the expressed BACE polypeptides is demonstrated by polyacrylamide gel electrophoresis in FIGS. 6 and 10. FIG. 6 shows the processing of polypeptides expressed from the construct B1, PET11a-BACE [SEQ ID NO:4] following two methods of purification. Lane A2 shows isolated inclusion body protein; lane A4 shows the refolded protein purified by Q-sepharose; and lane A7 shows the protein product after I-1 affinity chromatography. Lane B2 shows isolated inclusion body protein; lane B3 shows refolded protein purified through Q-sepharose; lane B4 through Sephacryl-200; and lane B5 shows the protein product after I-1 affinity chromatography.

FIG. 10 shows the processing of polypeptides expressed from the construct B2, including treatments with HIV-protease. Lane A2 shows inclusion bodies; lane A4 shows post Q-sepharose protein; lane A5 shows protein pre affinity chromatography; lane A6 shows the affinity column flow through; and lane A7 shows the protein product after I-1 affinity chromatography. Lane B2 shows inclusion bodies; lane B4 shows protein post-Q-sepharose; lane B6 shows protein treated with HIV-protease; lane B9 shows protein product after I-1 affinity chromatography. Lane C2 shows inclusion bodies; lane C4 shows protein post-Q-sepharose and Sepacryl-200 purification; lane C6 shows post first I-1 affinity chromatography; lanes C7 and C9 shows post-dialysis; lane C10 shows after adjustment to pH 5.7; lane C11 shows protein after HIV protease treatment; lane C14 shows the protein product after second I-1 affinity chromatography.

While preferred embodiments of the present invention have been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the extent they are not inconsistent with the teachings herein.

We claim:

1. A method for producing an active recombinant human Beta-site APP cleaving enzyme (BACE) polypeptide comprising:
   a) expressing a polynucleotide sequence encoding a BACE polypeptide lacking all or a portion of the sequence corresponding to residues 1-66 of SEQ ID NO: 1,
   b) solubilizing the BACE polypeptide in a denaturant at a pH from about 10 to about 11 and in the presence of a reducing agent;
   c) diluting the solubilized BACE polypeptide in an aqueous solution having a temperature of about 1° C. to about 15° C., to obtain a diluted sample; and
   d) incubating the diluted sample at a temperature of about 4° C. to about 15° C. until the BACE polypeptide folds into an active enzyme.

2. The method of claim 1, wherein the BACE polypeptide lacks a leader sequence and at least a first 24 amino acids of a prosequence.

3. The method of claim 1 wherein the polynucleotide sequence encodes a polypeptide that is at least 95% identical to the sequence comprising amino acids 66-432 of SEQ ID NO: 1.

4. The method of claim 1 wherein the BACE polypeptide has at least 40% of the activity of recombinant BACE expressed in CHO cells.

5. The method of claim 3 wherein the BACE polypeptide has at least 100% of the activity of recombinant BACE expressed in CHO cells.

6. The method of claim 1, wherein the denaturant is selected from the group consisting of urea, guanidine HCI, and guanidine thiocyanate, at a concentration from about 6M to about 8M.

7. The method of claim 1, wherein the reducing agents is selected from the group consisting of beta-mercaptoethanol (BME), glutathione, and dithiothreitol (DTT), or a combination thereof.

8. A method for producing an active recombinant human BACE polypeptide comprising:
   a) expressing a polynucleotide encoding the BACE polypeptide in a host cell to produce a BACE polypeptide inclusion bodies;
   b) solubilizing the BACE polypeptide inclusion bodies to release the recombinant human BACE polypeptide;
   c) reducing the released BACE polypeptide with a reducing agent;
   d) diluting the reduced BACE polypeptide with an aqueous solution having a temperature of about 1° C. to about 15° C.; and
   e) incubating the diluted BACE polypeptide at a temperature from about 4° C. to about 15° C. and at a pH from about 10 to about 11, to obtain the active recombinant human BACE polypeptide.

9. The method of claim 8, wherein the polynucleotide encodes the BACE polypeptide having N-terminal amino acids that facilitate expression in a host cell.

10. The method of claim 9 wherein the amino acids comprise a tag selected from the group consisting of:
   (i) a T7 leader sequence or a T7-caspase 8 leader sequence;
   (ii) a purification tag; and
   (iii) the T7 leader sequence or the T7-caspase 8 leader sequence and a purification tag.

11. The method of claim 10, wherein the nucleotides encoding the tag are located at either an N-terminus or C-terminus of the polynucleotide encoding the BACE polypeptide.

12. The method of claim 10, wherein the purification tag is the T7-Tag MASMTGGQQMGR [SEQ ID NO: 8], the six-histidine tag, the thioredoxin tag, the hemaglutinin tag, or the GST tag.

13. The method of claim 8, wherein the polynucleotide sequence expressing the BACE polypeptide is mutated to provide for codons suitable for expression of the BACE polypeptide in a host cell.

14. The method of claim 8, wherein the polynucleotide encodes the BACE polypeptide that is truncated by deletion of all or a portion of a cytoplasmic tail, a prosequence, a transmembrane domain, or any combination thereof.

15. The method of claim 9, wherein the polynucleotide encodes enzymatic cleavage sites to between the coding sequence for BACE polypeptide and the coding sequence for the N-terminal amino acids.

16. The method of claim 8, wherein the polynucleotide encodes the BACE polypeptide having an N-terminal amino acid within the protease domain.

17. The method of claim 16, wherein the BACE polypeptide begins at a position downstream of $T^1$ of SEQ ID NO: 1.

18. The method of claim 17, wherein the BACE polypeptide begins at either $R^{36}$ or $F^{39}$ of SEQ ID NO: 1.

19. The method of claim 10, wherein the polynucleotide encodes a soluble BACE polypeptide having an N-terminus at a position selected from one of residues 24-66 and a C-terminus at residue $S^{432}$ of SEQ ID NO: 1.

20. A method for refolding an active recombinant human BACE polypeptide comprising:
   a) diluting a solubilized and a reduced BACE polypeptide with a low ionic strength aqueous solution having a temperature of about 1° C. to about 15° C.;
   b) incubating the diluted BACE polypeptide at a starting pH of about 10 to about 11, and at a temperature of about 1° C. to about 15° C. for about 2 days to about 6 weeks to allow the BACE polypeptide to fold into an active enzyme; and
   c) recovering the active refolded BACE polypeptide.

21. The method of claim 20, further comprising applying the BACE polypeptide of step c) onto an ion exchange column and eluting the BACE polypeptide.

22. The method of claim 21, further comprising applying the eluted BACE polypeptide onto a size exclusion column and eluting the BACE polypeptide.

23. The method of claim 22, further comprising applying the eluted BACE polypeptide onto an affinity chromatography column comprising an inhibitor, and eluting the active recombinant human BACE polypeptide.

24. The method of claim 23 wherein the inhibitor is l-1 of SEQ ID NO:28 .

* * * * *